(12) United States Patent
Joung et al.

(10) Patent No.: US 11,326,157 B2
(45) Date of Patent: May 10, 2022

(54) BASE EDITORS WITH IMPROVED PRECISION AND SPECIFICITY

(71) Applicant: The General Hospital Corporation, Boston, MA (US)

(72) Inventors: J. Keith Joung, Winchester, MA (US); Jason Michael Gehrke, Cambridge, MA (US)

(73) Assignee: The General Hospital Corporation, Boston, MA (US)

(*) Notice: Subject to any disclaimer, the term of this patent is extended or adjusted under 35 U.S.C. 154(b) by 0 days.

(21) Appl. No.: 16/615,559

(22) PCT Filed: May 25, 2018

(86) PCT No.: PCT/US2018/034719
§ 371 (c)(1),
(2) Date: Nov. 21, 2019

(87) PCT Pub. No.: WO2018/218188
PCT Pub. Date: Nov. 29, 2018

(65) Prior Publication Data
US 2020/0172885 A1 Jun. 4, 2020

Related U.S. Application Data

(60) Provisional application No. 62/622,676, filed on Jan. 26, 2018, provisional application No. 62/541,544, filed on Aug. 4, 2017, provisional application No. 62/511,296, filed on May 25, 2017.

(51) Int. Cl.
| | |
|---|---|
| *C12N 9/78* | (2006.01) |
| *C12N 9/22* | (2006.01) |
| *C12N 15/10* | (2006.01) |
| *C12N 15/63* | (2006.01) |
| *C12N 15/90* | (2006.01) |
| *C07K 14/435* | (2006.01) |
| *C07K 14/47* | (2006.01) |
| *C12N 5/0789* | (2010.01) |
| *A61K 38/00* | (2006.01) |

(52) U.S. Cl.
CPC ............ *C12N 9/78* (2013.01); *C07K 14/435* (2013.01); *C07K 14/4703* (2013.01); *C12N 5/0647* (2013.01); *C12N 9/22* (2013.01); *C12N 15/102* (2013.01); *C12N 15/63* (2013.01); *C12N 15/90* (2013.01); *C07K 2319/70* (2013.01); *C07K 2319/80* (2013.01); *C07K 2319/81* (2013.01); *C12N 2310/20* (2017.05); *C12Y 305/04001* (2013.01)

(58) Field of Classification Search
CPC .................... C12Y 305/04005; C07K 2319/00
See application file for complete search history.

(56) References Cited

U.S. PATENT DOCUMENTS

| | | |
|---|---|---|
| 6,294,330 B1 | 9/2001 | Michnick et al. |
| 2011/0104787 A1 | 5/2011 | Church et al. |
| 2015/0174169 A1 | 6/2015 | Genovese et al. |
| 2016/0177278 A1 | 6/2016 | Wolfe et al. |
| 2017/0058271 A1 | 3/2017 | Joung et al. |
| 2017/0121693 A1* | 5/2017 | Liu .................... A61P 35/00 |
| 2018/0073012 A1 | 3/2018 | Liu et al. |
| 2018/0312828 A1 | 11/2018 | Liu et al. |
| 2019/0010481 A1 | 1/2019 | Joung et al. |
| 2019/0093128 A1* | 3/2019 | Chen .................... C12N 9/22 |
| 2019/0106687 A1 | 4/2019 | Joung et al. |
| 2020/0140842 A1 | 5/2020 | Joung et al. |
| 2020/0172895 A1 | 6/2020 | Joung et al. |
| 2020/0308571 A1 | 10/2020 | Joung et al. |
| 2021/0395730 A1 | 12/2021 | Grunewald et al. |

FOREIGN PATENT DOCUMENTS

| | | |
|---|---|---|
| CA | 2915837 A1 | 12/2014 |
| WO | WO 2008/027899 | 3/2008 |
| WO | WO 2014/152432 | 9/2014 |
| WO | WO 2016/028682 | 2/2016 |
| WO | WO 2016/112242 | 7/2016 |
| WO | WO 2016/141224 | 9/2016 |
| WO | WO 2017/011721 | 1/2017 |
| WO | WO 2017/040348 | 3/2017 |
| WO | WO 2017/189308 | 11/2017 |
| WO | WO 2018/035387 | 2/2018 |
| WO | WO 2018/165629 | 9/2018 |
| WO | WO 2018/176009 | 9/2018 |
| WO | WO 2018/218206 | 11/2018 |
| WO | WO 2020/077138 | 5/2020 |
| WO | WO 2021/042047 | 3/2021 |
| WO | WO 2021/042062 | 3/2021 |
| WO | WO 2021/113611 | 6/2021 |

OTHER PUBLICATIONS

Bulliard et al. (2011) Structure-Function Analyses Point to a Polynucleotide-Accommodating Groove Essential for APOBEC3A Restriction Activities, J. Virol., vol. 85, No. 4, pp. 1765-1776.*
Mitra et al. (2014) Structural determinants of human APOBEC3A enzymatic and nucleic acid binding properties,, Nucleic Acids Res., vol. 42, pp. 1095-1110.*
Kouno et al. (2017) Crystal structure of APOBEC3A bound to single-stranded DNA reveals structural basis for cytidine deamination and specificityNature comm., vol. 8, No. 15024, pp. 1-8.*
Henry et al. (2012) Evolution of the Primate APOBEC3A Cytidine Deaminase Gene and Identification of Related Coding Regions.; PLoS ONE , vol. 7: E30036-E30036.*
Aynaud et al., "Human Tribbles 3 protects nuclear DNA from cytidine deamination by APOBEC3A." Journal of Biological Chemistry, Nov. 2012, 287(46):39182-39192.
Boissel et al., "MegaTALs: A Rare-cleaving Nuclease Architecture for Therapeutic Genome Engineering," Nucleic Acids Research, Feb. 2014, 42(4):2591-2601.

(Continued)

*Primary Examiner* — Scarlett Y Goon
*Assistant Examiner* — Samuel W Liu
(74) *Attorney, Agent, or Firm* — Fish & Richardson P.C.

(57) ABSTRACT

Methods and compositions for improving the genome-wide specificities of targeted base editing technologies.

21 Claims, 22 Drawing Sheets

Specification includes a Sequence Listing.

(56) References Cited

OTHER PUBLICATIONS

Bolukbasi et al., "DNA-binding-domain Fusions Enhance the Targeting Range and Precision of Cas9," Nature Methods, Dec. 2015, 12(12):1150-1156.

Bransteitter et al., "The Current Structural and Functional Understanding of APOBEC Deaminases," Cellular and Molecular Life Sciences, Oct. 2009, 66(19):3137-3147.

Byeon et al., "NMR Structure of Human Restriction Factor APOBEC3 A Reveals Substrate Binding and Enzyme Specificity." Nature Communication, May 2013, 4(1):1890, 11 pages.

Chen et al., "Structure of the DNA Deaminase Domain of the HIV-1 Restriction Factor APOBEC3G," Nature, Mar. 2008, 452(7183):116-119.

Chen et al., "Targeted activation of diverse CRIPSR-Cas systems for mammalian genome editing via proximal CRISPR targeting," Nature Communications, Apr. 2017, 8(1):1-12.

Cho et al., "Targeted genome engineering in human cells with the Cas9 RNA-guided endonuclease," Nat. Biotechnol., Mar. 2013, 31(3):230-232.

Cone et al., "Inhibitor of uracil-DNA glycosylase induced by bacteriophage PBS2. Purification and preliminary characterization," Journal of Biological Chemistry, Nov. 1980, 255(21):10354-10358.

Cong et al., "Multiplex genome engineering using CRISPR/Cas systems," Science, Feb. 2013, 339(6121):819-823.

Dahlman et al., "Orthogonal Gene Knockout and Activation with a Catalytically Active Cas9 Nuclease." Nature Biotechnology, Nov. 2015, 33(11):1159-1161.

Dicarlo et al., "Genome engineering in *Saccharomyces cerevisiae* using CRISPR-Cas systems," Nucleic Acids Res., Mar. 2013, 41(7):4336-4343.

Ear & Michnick, "A General Life-death Selection Strategy for Dissecting Protein Functions." Nature Methods, Nov. 2009, 6(11):813-816.

Fagerlund et al., "The Cpf1 CRISPR-Cas protein expands genome-editing tools," Genome Biol., Dec. 2015, 16(1):251, 3 pages.

Friedland et al., "Characterization of *Staphylococcus aureus* Cas9: a Smaller Cas9 for All-in-One Adeno-Associated Virus Delivery and Paired Nickase Applications," Genome Biology, Dec. 2015, 16(1):257, 10 pages.

Fu et al., "Improving CRISPR-Cas nuclease specificity using truncated guide RNAs." Nature biotechnology, Mar. 2014, 32(3):279-284.

Fu et al., "Targeted genome editing in human cells using CRISPR/Cas nucleases and truncated guide RNAs," Methods Enzymol, Jan. 2014, 546:21-45.

Gasiunas et al., "Cas9-CrRNA Ribonucleoprotein Complex Mediates Specific DNA Cleavage for Adaptive Immunity in Bacteria." Proceedings of the National Academy of Sciences, Sep. 2012, 109(39):E2579-E2586.

Gaudelli et al., "Programmable base editing of A•T to G•C in genomic DNA without DNA cleavage," Nature, Nov. 2017, 551(7681):464-471.

Gehrke et al., "High-precision CRISPR-Cas9 base editors with minimized bystander and off-target mutations," bioRxiv, Jan. 2008, 1:273938, 22 pages.

Harris et al., "RNA Editing Enzyme APOBEC1 and Some of Its Homologs Can Act as DNA Mutators," Molecular Cell, Nov. 2002, 10(5):1247-1253.

Hess et al., "Directed Evolution Using DCas9-targeted Somatic Hypermutation in Mammalian Cells," Nature Methods, Dec. 2016, 13(12):1036-1042.

Hess et al., "Methods and Applications of CRISPR-Mediated Base Editing in Eukaryotic Genomes," Mol. Cell., Oct. 2017, 68(1):26-43.

Hirano et al. "Crystal Structure of Francisella Novicida Cas9," Cell, Feb. 2016, 164(5):950-961.

Holden et al., "Crystal structure of the anti-viral APOBEC3G catalytic domain and functional implications," Nature, Nov. 2008, 456(7218):121-124.

Holtz et al., "APOBEC3G cytosine deamination hotspots are defined by both sequence context and single-stranded DNA secondary structure," Nucleic Acids Research, Jul. 2013, 41(12):6139-6148.

Hwang et al., "Efficient genome editing in zebrafish using a CRISPR-Cas system," Nat. Biotechnol., Jan. 2013, 31(3):227-229.

Hwang et al., "Targeted mutagenesis in zebrafish using CRISPR RNA-guided nucleases," Methods Mol. Biol., 2015, 1311:317-34.

Jasin & Rothstein., "Repair of strand breaks by homologous recombination." Cold Spring Harbor Perspectives in Biology, Nov. 2013, 5(11):a012740, 18 pages.

Jiang et al., "RNA-guided editing of bacterial genomes using CRISPR-Cas systems," Nat. Biotechnol., Mar. 2013, 31(3):233-239.

Jinek et al., "A Programmable Dual-RNA-Guided DNA Endonuclease in Adaptive Bacterial Immunity," Science, Aug. 2012, 337(6096):816-821.

Jinek et al., "RNA-programmed genome editing in human cells," Elife 2, Jan. 2013, 2:e00471, 9 pages.

Kim et al. "Increasing the Genome-Targeting Scope and Precision of Base Editing with Engineered Cas9-Cytosine Deaminase Fusions," Nature Biotechnology, Apr. 2017, 35(4):371-376.

Kim et al., "Genome-wide Target Specificities of CRISPR RNA-guided Programmable Deaminases," Nature Biotechnology, May 2017, 34(5):475-480.

Kleinstiver et al., "Broadening the targeting range of *Staphylococcus aureus* CRISPR-Cas9 by modifying PAM recognition," Nat. Biotechnol., Dec. 2015, 33(12):1293-1298.

Kleinstiver et al., "Engineered CRISPR-Cas9 nucleases with altered PAM specificities," Nature, Jul. 2015; 523(7561):481-485.

Kleinstiver et al., "Genome-wide specificities of CRISPR-Cas Cpf1 nucleases in human cells," Nat. Biotechnol., Aug. 2016, 34(8):869-874.

Kleinstiver et al., "High-fidelity CRISPR-Cas9 nucleases with no detectable genome-wide off-target effects," Nature, Jan. 2016, 529(7587):490-495.

Kohli et al., "A Portable Hot Spot Recognition Loop Transfers Sequence Preferences from APOBEC Family Members to Activation-induced Cytidine Deaminase," Journal of Biological Chemistry, Aug. 2009, 284(34):22898-22904.

Komor et al., "Improved base excision repair inhibition and bacteriophage Mu Gam protein yields C : G-to-T : A base editors with higher efficiency and product purity," Sci. Adv., Aug. 2017, 3(8):eaao4774, 9 pages.

Komor et al., "Programmable editing of a target base in genomic DNA without double-stranded DNA cleavage," Nature, 2016, 533(7603):420-424.

Konermann et al., "Genome-scale transcriptional activation by an engineered CRISPR-Cas9 complex," Nature, Jan. 2015, 517(7536):583-588.

Kuscu & Adli., "CRISPR-Cas9-AID Base Editor Is a Powerful Gain-of-function Screening Tool," Nature Methods, Dec. 2016, 13(12):983-984.

Langlois et al., "Mutational comparison of the single-domained APOBEC3C and double-domained APOBEC3F/G anti-retroviral cytidine deaminases provides insight into their DNA target site specificities," Nucleic Acids Research, Jan. 2005, 33(6):1913-1923.

Logue et al., "A DNA sequence recognition loop on APOBEC3A controls substrate specificity," PloS One, (5):e97062, 10 pages.

Luscombe et al., "Amino acid-base interactions: a three-dimensional analysis of protein-DNA interactions at an atomic level," Nucleic Acids Research, Jul. 2001, 29(13):2860-2874.

Ma et al., "Single-stranded DNA cleavage by divergent CRISPR-Cas9 enzymes," Molecular Cell, Nov. 2015, 60(3):398-407.

Maeder et al., "Rapid 'Open-Source' Engineering of Customized Zinc-Finger Nucleases for Highly Efficient Gene Modification," Molecular Cell, 31(2):294-301.

Makarova et al., "An updated evolutionary classification of CRISPR-Cas systems," Nat. Rev. Microbiol, Nov. 2015, 13(11):722-736.

Mali et al., "RNA-Guided Human Genome Engineering via Cas9," Science, Feb. 2013, 339(6121):823-826.

(56) References Cited

OTHER PUBLICATIONS

Michnick et al., Chapter 25: Protein-Fragment Complementation Assays for Large-Scale Analysis, Functional Dissection and Dynamic Studies of Protein-Protein Interactions in Living Cells, Signal Transduction Protocols, Methods in Molecular Biology, Jul. 2011, 395-425.
Mitra et al., "Sequence and Structural Determinants of Human APOBEC3H Deaminase and Anti-HIV-1 Activities," Retrovirology, Dec. 2015, 12(1):3, 15 pages.
Nair et al., "Biochemical and Biological Studies of Mouse APOBEC3," Journal of Virology, Apr. 2014, 88(7):3850-3860.
Nishida et al., "Targeted Nucleotide Editing Using Hybrid Prokaryotic and Vertebrate Adaptive Immune Systems," Science, Sep. 2016, 353(6305):aaf8729.
Nishimasu al., "Crystal structure of Cas9 in complex with guide RNA and target DNA," Cell, Feb. 2014, 156(5):935-949.
Osborn et al., "Fanconi anemia gene editing by the CRISPR/Cas9 system," Hum. Gene. Ther., Feb. 2015, 26(2):114-126.
Pattanayak et al., "Revealing off-Target Cleavage Specificities of Zinc-Finger Nucleases by in Vitro Selection," Nature Methods, Sep. 2011, 8(9):765.
PCT International Preliminary Report on Patentability in PCT Appln. No. PCT/US2018/034687, dated Nov. 26, 2019, 9 pages.
PCT International Preliminary Report on Patentability in PCT Appln. No. PCT/US2018/034719, dated Nov. 26, 2019.
PCT International Preliminary Report on Patentability in PCT Appln. No. PCT/US2018/034742, dated Nov. 26, 2019.
PCT International Search Report and Written Opinion in PCT Appln. No. PCT/US2018/034687, dated Sep. 24, 2018, 13 pages.
PCT International Search Report and Written Opinion in PCT Appln. No. PCT/US2018/034719, dated Sep. 20, 2018, 13 pages.
PCT International Search Report and Written Opinion in PCT Appln. No. PCT/US2018/034742, dated Sep. 24, 2018, 13 pages.
Pham et al., "Structural Analysis of the Activation-induced Deoxycytidine Deaminase Required in Immunoglobulin Diversification," DNA Repair, Jul. 2016, 43:48-56.
Rathore et al., "The local dinucleotide preference of APOBEC3G can be altered from 5'-CC to 5'-TC by a single amino acid substitution," J. Mol. Biol., Nov. 2013, 425(22):4442-4454.
Rebhandl et al., "AID/APOBEC Deaminases and Cancer," Oncoscience 2, Apr. 2015, 2(4):320-333.
Rees et al., "Improving the DNA specificity and applicability of base editing through protein engineering and protein delivery," Nature Communications, Jun. 2017, 8(1):1-10.
Salter et al., "The APOBEC Protein Family: United by Structure, Divergent in Function," Trends in Biochemical Sciences, Jul. 2016, 41(7):578-594.
Sanjana et al., "A transcription activator-like effector toolbox for genome engineering," Nature Protocols, Jan. 2012, 7(1):171-192.
Santos-Pereira et al., "R Loops: New Modulators of Genome Dynamics and Function." Nature Reviews Genetics, Oct. 2015, 16(10):583-597.
Schunder et al., "First indication for a functional CRISPR/Cas system in Francisella tularensis," Int. J. Med. Microbiol., Mar. 2013, 303(2):51-60.
Shandilya et al., "Crystal Structure of the APOBEC3G Catalytic Domain Reveals Potential Oligomerization Interfaces," Structure, Jan. 2010, 18(1):28-38.
Shen et al., "Generation of gene-modified mice via Cas9/RNA-mediated gene targeting," Cell Res., Apr. 2013, 23(5):720-723.
Shi et al., "Crystal Structure of the DNA Deaminase APOBEC3B Catalytic Domain," Journal of Biological Chemistiy, Nov. 2015, 290(47):28120-28130.
Shi et al., "Structural Basis for Targeted DNA Cytosine Deamination and Mutagenesis by APOBEC3A and APOBEC3B," Nature Structural & Molecular Biology, Feb. 2017, 24(2):131-139.
Shinohara et al., "APOBEC3B can impair genomic stability by inducing base substitutions in genomic DNA in human cells," Scientific Reports, 2012, 2:806.

Shmakov et al., "Discovery and functional characterization of diverse class 2 CRISPR-Cas systems," Mol. Cell., Nov. 2015, 60(3):385-397.
Slaymaker et al., "Rationally Engineered Cas9 Nucleases with Improved Specificity." Science, Jan. 2016, 351(6268):84-88.
Suspene et al., "Recovery of APOBEC3-edited human immunodeficiency virus G→ A hypermutants by differential DNA denaturation PCR," Journal of General Virology, Jan. 2005, 86(1):125-129.
Tang et al., "A CRISPR-Cpf1 System for Efficient Genome Editing and Transcriptional Repression inPlants." Nature Plants, Feb. 2017, 3:17108, 5 pages.
Tsai & Joung., "Defining and improving the genome-wide specificities of CRISPR-Cas9 nucleases," Nat. Rev. Genet., May 2016, 17(5):300-312.
Tsai et al., "Dimeric CRISPR RNA-guided FokI nucleases for highly specific genome editing," Nat. Biotechnol., Jun. 2014, 2(6):569-576.
Tsai et al., "GUIDE-seq Enables Genome-wide Profiling of Off-target Cleavage by CRISPR-Cas Nucleases," Nature Biotechnology, Feb. 2015, 33(2):187-197.
Wu et al., "Genome-wide Binding of the CRISPR Endonuclease Cas9 in Mammalian Cells," Nature Biotechnology, Jul. 2014, 32(7):670-676.
Wyvekens et al., "Dimeric CRISPR RNA-Guided FokI-dCas9 Nucleases Directed by Truncated gRNAs for Highly Specific Genome Editing," Hum. Gene. Ther., Jul. 2015, 26(7):425-431.
Yamada et al., "Crystal Structure of the Minimal Cas9 from Campylobacter Jejuni Reveals the Molecular Diversity in the CRISPR-Cas9 Systems," Molecular Cell, Mar. 2017, 65(6):1109-1121.
Yamano et al., "Crystal Structure of *Acidaminococcus* Sp. Cpf1 in Complex with CrRNA and Target DNA," May 2016, 165(4):949-962.
Yang et al., "APOBEC: from mutator to editor," J. Genet. Genomics., Sep. 2017, 20;44(9):423-437.
Yang et al., "Engineering and optimising deaminase fusions for genome editing," Nature Communications, 2016, 7:1-12.
Zetsche et al., "Cpf1 is a single RNA-guided endonuclease of a class 2 CRISPR-Cas system," Cell, 2015, 163(3):759-771.
Extended European Search Report in European Appln. No. 18806041.2, dated Dec. 10, 2020, 8 pages.
Extended European Search Report in European Appln. No. 18806459.6, dated Dec. 2, 2020, 9 pages.
Gehrke et al., "An APOBEC3A-Cas9 base editor with minimized bystander and off-target activities," Nature Biotechnology, Jul. 2018, 36(10):977-982.
Woolf et al., "To cleave or not to cleave: therapeutic gene editing with and without programmable nucleases," Nat. Rev. Drug Discov., Mar. 2017, 16(4):296, 3 pages.
Zhang et al., "Annual Review of Biochemistry Synthetic Genomes," Annu. Rev. Biochem., Jun. 2020, 89:77-101.
Chen et al., "Hypermutation induced by APOBEC-1 overexpression can be eliminated," RNA, May 2010, 16(5):1040-1052.
Chester et al., "The apolipoprotein B mRNA editing complex performs a multifunctional cycle and suppresses nonsense-mediated decay," EMBO J. Aug. 2003, (15):3971-3982.
EP Extended European Search Report in European Appln. No. 18805050.4, dated Mar. 18, 2021, 9 pages.
Kim et al., "Structural and kinetic characterization of *Escherichia coli* TadA, the wobble-Specific tRNA deaminase," Biochemistry, May 2006, 45(20):6407-6416.
Mok et al., "A bacterial cytidine deaminase toxin enables CRISPR-free mitochondrial base editing," Nature, Jul. 2020, 583(7817):631-637.
Park et al., "Off-target Editing by CRISPR-guided DNA base editors," Biochemistry, 2019, 58(36):3727-3734.
Porto et al., "Base editing: advances and therapeutic opportunities," Nature Reviews Drug Discovery, Dec. 2020, 19(12):839-859.
Sharma et al., "Transient overexpression of exogenous APOBEC3A causes C-to-U RNA editing of thousands of genes," RNA Biol., May 2017, 14(5):603-610.

(56) References Cited

OTHER PUBLICATIONS

Teng et al., "Mutational Analysis of Apolipoprotein B mRNA Editing Enzyme (APOBEC1). Structure-Function Relationships of RNA Editing and Dimerization," J. Lipid Res., Apr. 1999, 40(4):623-635.

Yamanaka et al., "Cloning and mutagenesis of the rabbit ApoB mRNA editing protein. A zinc motif is essential for catalytic activity, and noncatalytic auxiliary factor(s) of the editing complex are widely distributed," J Biol Chem., Aug. 1994, 269(34):21725-21734.

Blanc et al., "Genome-wide identification and functional analysis of Apobec-1-mediated C-to-U RNA editing in mouse small intestine and liver," Genome Biol., 2014, 15:R79, 17 pages.

Chadwick et al., "Reduced Blood Lipid Levels With In Vivo CRISPR-Cas9 Base Editing of ANGPTL3," Circulation, 2018, 137:975-977.

Chen et al., "Apolipoprotein B-48 is the product of a messenger RNA with an organ-specific in-frame stop codon," Science, 1987, 238:363-366.

Komor et al., "CRISPR-Based Technologies for the Manipulation of Eukaryotic Genomes," Cell, 2017, 168:20-36.

Rosenberg et al., "Transcriptome-wide sequencing reveals numerous APOBEC1 mRNA-editing targets in transcript 3' UTRs," Nat Struct Mol Biol., 2011, 18:230-236.

Shimatani et al., "Targeted base editing in rice and tomato using a CRISPR-Cas9 cytidine deaminase fusion," Nat Biotechnol., 2017, 35:441-443.

Skuse et al., "The neurofibromatosis type I messenger RNA undergoes base-modification RNA editing," Nucleic Acids Res., 1996, 24:478-485.

Sowden et al., "Overexpression of APOBEC-1 results in mooring sequence-dependent promiscuous RNA editing," J Biol Chem., 1996, 271:3011-3017.

Teng et al., "Molecular cloning of an apolipoprotein B messenger RNA editing protein," Science, 1993, 260:1816-1819.

Thuronyi et al., "Continuous evolution of base editors with expanded target compatibility and improved activity," Nat Biotechnol., 2019, 37:1070-1079.

Yamanaka et al., "A novel translational repressor mRNA is edited extensively in livers containing tumors caused by the transgene expression of the apoB mRNA-editing enzyme," Genes Dev., 1997, 11:321-333.

Yamanaka et al., "Hyperediting of multiple cytidines of apolipoprotein B mRNA by APOBEC-1 requires auxiliary protein(s) but not a mooring sequence motif," J Biol Chem., 1996, 271:11506-11510.

Yeh et al., "In vivo base editing of post-mitotic sensory cells," Nat Commun., 2018, 9:2184, 10 pages.

Zafra et al., "Optimized base editors enable efficient editing in cells, organoids and mice," Nat Biotechnol., 2018, 36:888-893.

Zhang et al., "Programmable base editing of zebrafish genome using a modified CRISPR-Cas9 system," Nat Commun., 2017, 8:118, 5 pages.

Zong et al., "Precise base editing in rice, wheat and maize with a Cas9-cytidine deaminase fusion," Nat Biotechnol., 2017, 35:438-440.

* cited by examiner

FIG. 3A
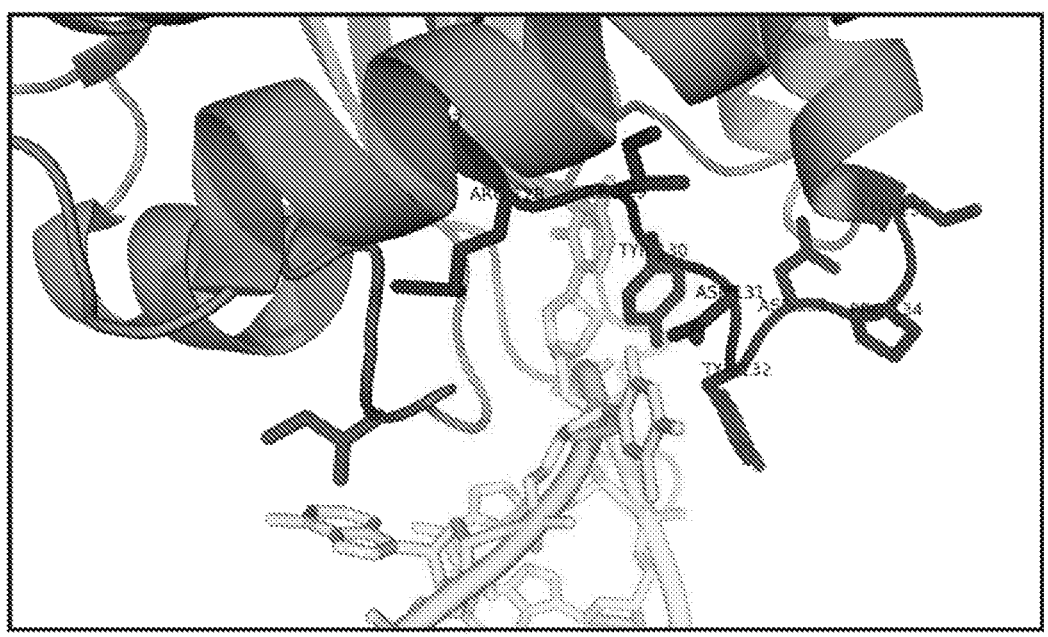
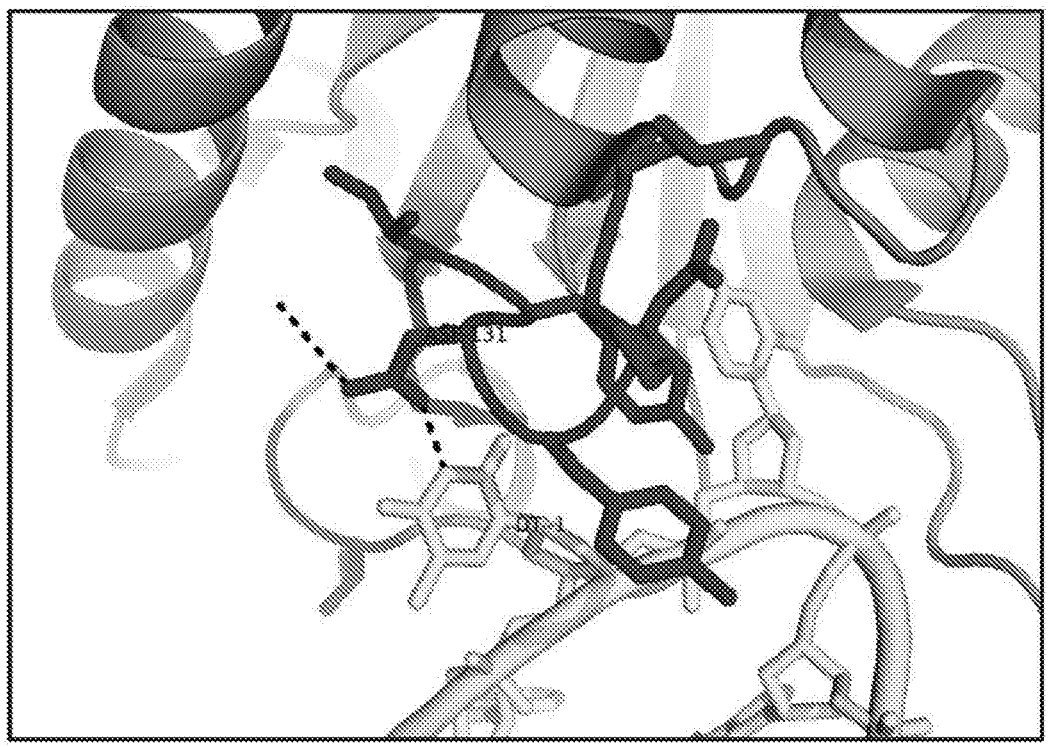
FIG. 3B

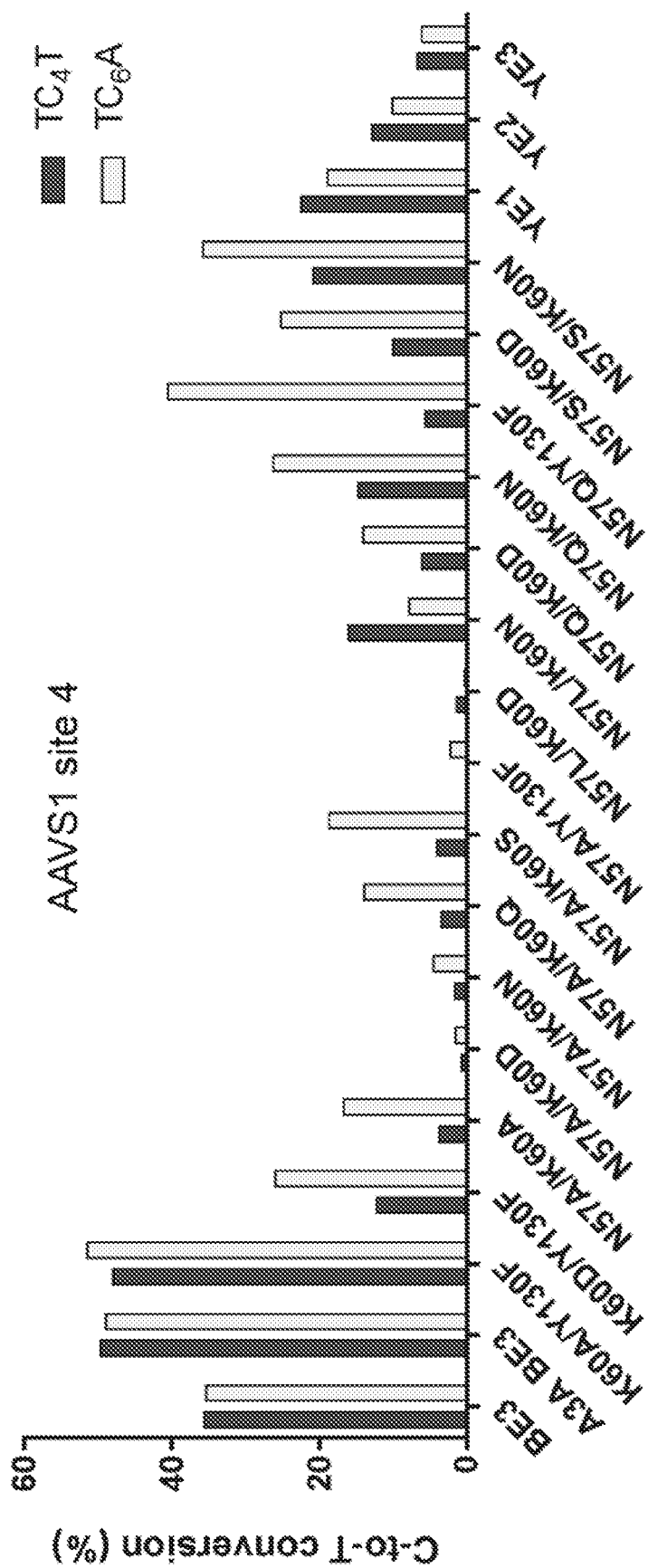
FIG. 10, continued

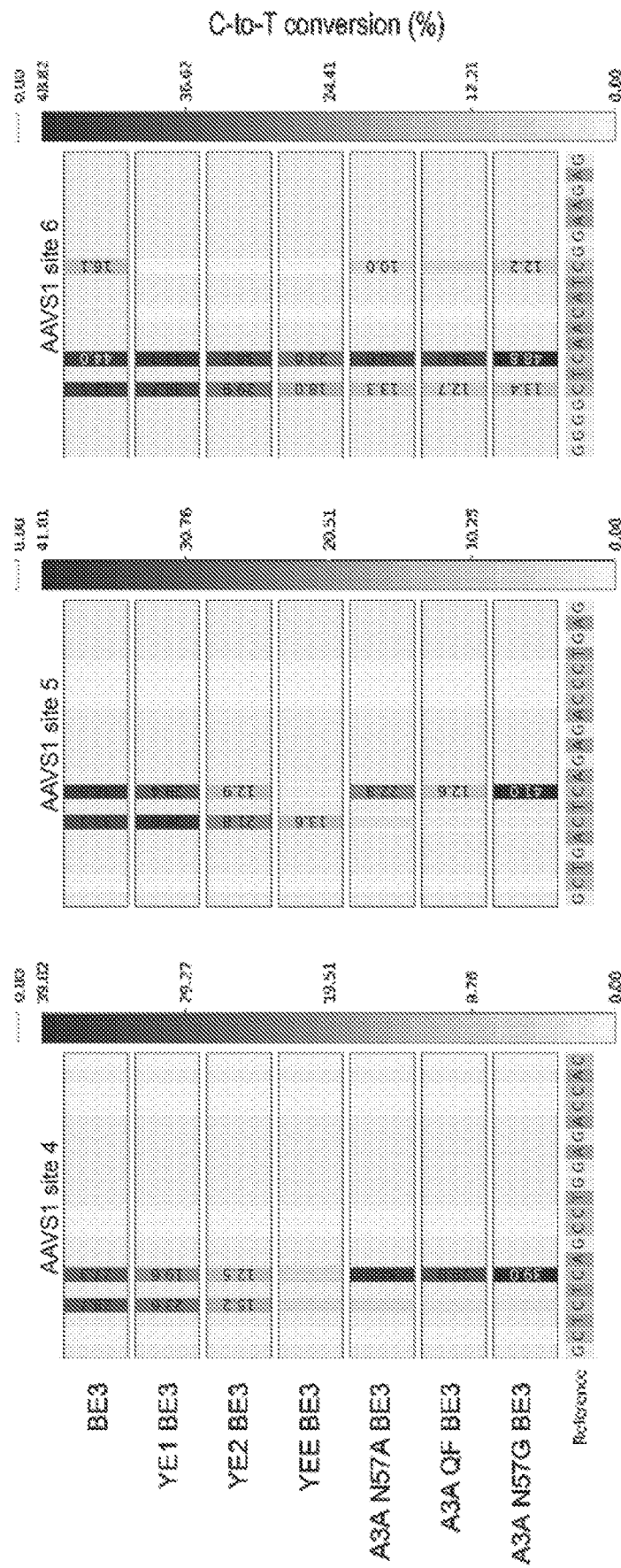
FIG. 11, continued

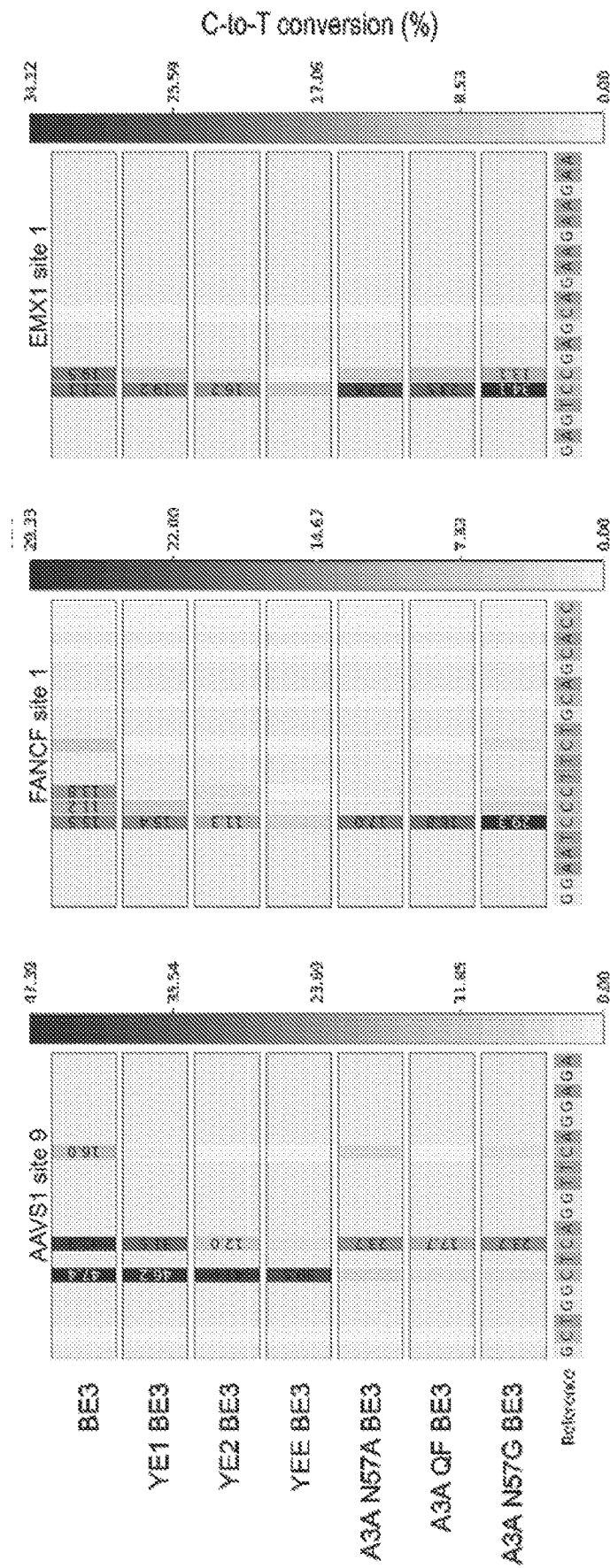
FIG. 12, continued

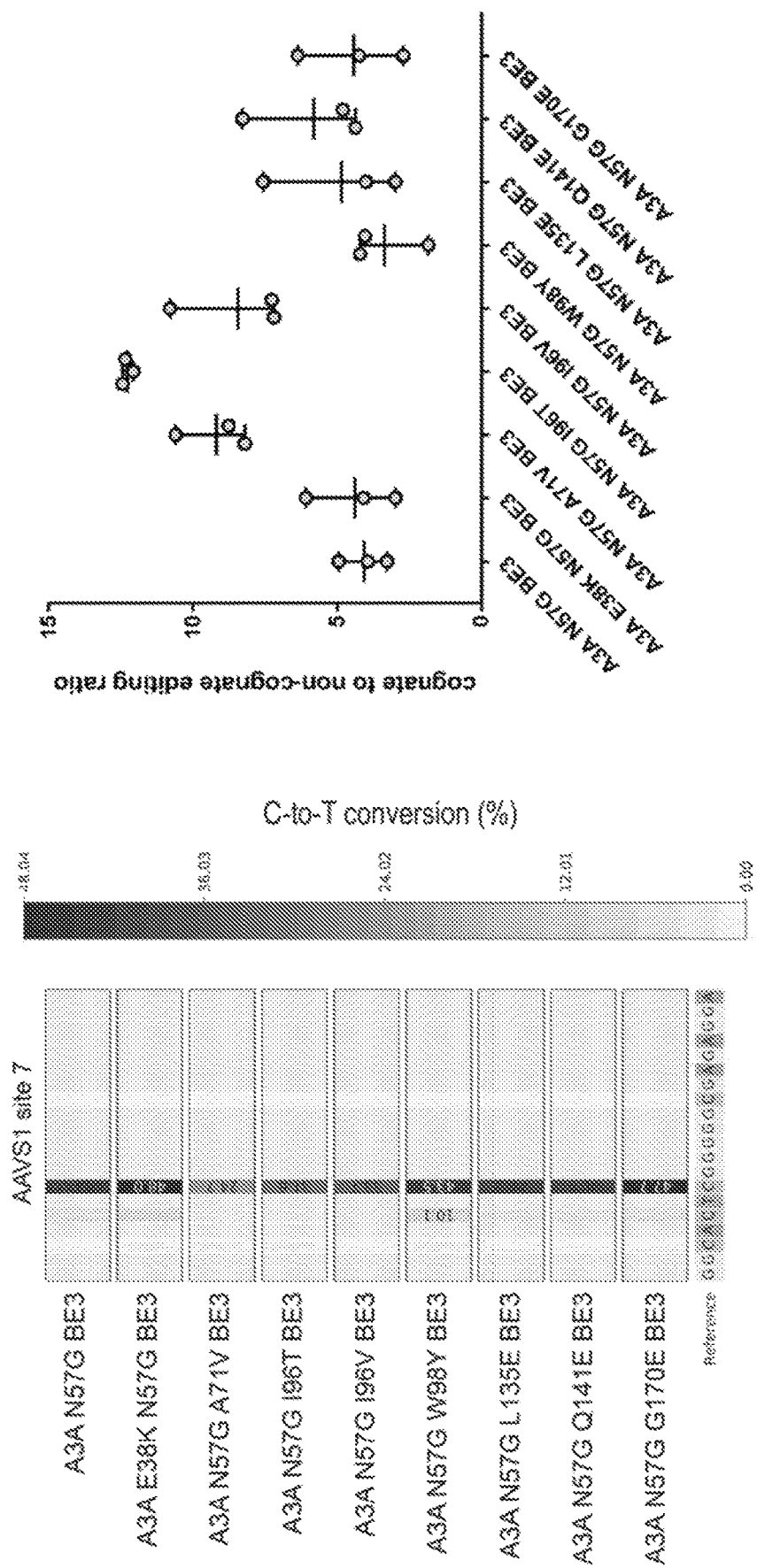
FIG. 13, continued

SEQUENCE LISTING

```
<160> NUMBER OF SEQ ID NOS: 67

<210> SEQ ID NO 1
<211> LENGTH: 12
<212> TYPE: PRT
<213> ORGANISM: Artificial
<220> FEATURE:
<223> OTHER INFORMATION: fragment of hAID

<400> SEQUENCE: 1

Gln Phe Lys Asn Val Arg Trp Ala Lys Gly Arg Arg
1               5                   10

<210> SEQ ID NO 2
<211> LENGTH: 9
<212> TYPE: PRT
<213> ORGANISM: Artificial
<220> FEATURE:
<223> OTHER INFORMATION: fragment of hAID solubility variant (hAIDv)

<400> SEQUENCE: 2

Asn Phe Asn Asn Gly Ile Gly Arg His
1               5

<210> SEQ ID NO 3
<211> LENGTH: 9
<212> TYPE: PRT
<213> ORGANISM: Artificial
<220> FEATURE:
<223> OTHER INFORMATION: fragment of hAPOBEC3A

<400> SEQUENCE: 3

Asn Phe Asn Asn Gly Ile Gly Arg His
1               5

<210> SEQ ID NO 4
<211> LENGTH: 12
<212> TYPE: PRT
<213> ORGANISM: Artificial
<220> FEATURE:
<223> OTHER INFORMATION: fragment of hAPOBEC3C

<400> SEQUENCE: 4

Gln Phe Lys Asn Leu Trp Glu Ala Asn Asp Arg Asn
1               5                   10

<210> SEQ ID NO 5
<211> LENGTH: 12
<212> TYPE: PRT
<213> ORGANISM: Artificial
<220> FEATURE:
<223> OTHER INFORMATION: fragment of hAPOBEC3F - catalytic domain
```

```
<400> SEQUENCE: 5

His Phe Lys Asn Leu Arg Lys Ala Tyr Gly Arg Asn
1               5                   10

<210> SEQ ID NO 6
<211> LENGTH: 12
<212> TYPE: PRT
<213> ORGANISM: Artificial
<220> FEATURE:
<223> OTHER INFORMATION: fragment of hAPOBEC3G - catalytic domain

<400> SEQUENCE: 6

Asn Phe Asn Asn Glu Pro Trp Val Arg Gly Arg His
1               5                   10

<210> SEQ ID NO 7
<211> LENGTH: 12
<212> TYPE: PRT
<213> ORGANISM: Artificial
<220> FEATURE:
<223> OTHER INFORMATION: fragment of mAPOBEC3 - catalytic domain

<400> SEQUENCE: 7

His Phe Lys Asn Leu Gly Tyr Ala Lys Gly Arg Lys
1               5                   10

<210> SEQ ID NO 8
<211> LENGTH: 15
<212> TYPE: PRT
<213> ORGANISM: Artificial
<220> FEATURE:
<223> OTHER INFORMATION: fragment of hAPOBEC3H

<400> SEQUENCE: 8

Gln Phe Asn Asn Lys Arg Arg Leu Arg Arg Pro Tyr Tyr Pro Arg
1               5                   10                  15

<210> SEQ ID NO 9
<211> LENGTH: 9
<212> TYPE: PRT
<213> ORGANISM: Artificial
<220> FEATURE:
<223> OTHER INFORMATION: fragment of rAPOBEC1

<400> SEQUENCE: 9

Phe Phe Asp Pro Arg Glu Leu Arg Lys
1               5

<210> SEQ ID NO 10
<211> LENGTH: 17
<212> TYPE: PRT
<213> ORGANISM: Artificial
<220> FEATURE:
<223> OTHER INFORMATION: fragment of hAID

<400> SEQUENCE: 10

Phe Thr Ala Arg Leu Tyr Phe Cys Glu Asp Arg Lys Ala Glu Pro Glu
1               5                   10                  15

Gly

<210> SEQ ID NO 11
<211> LENGTH: 17
<212> TYPE: PRT
<213> ORGANISM: Artificial
<220> FEATURE:
<223> OTHER INFORMATION: fragment of hAID solubility variant (hAIDv)
```

<400> SEQUENCE: 11

Phe Thr Ala Arg Leu Tyr Phe Cys Glu Asp Arg Lys Ala Glu Pro Glu
1               5                   10                  15

Gly

<210> SEQ ID NO 12
<211> LENGTH: 15
<212> TYPE: PRT
<213> ORGANISM: Artificial
<220> FEATURE:
<223> OTHER INFORMATION: fragment of hAPOBEC3A

<400> SEQUENCE: 12

Phe Ala Ala Arg Ile Tyr Asp Tyr Asp Pro Leu Tyr Lys Glu Ala
1               5                   10                  15

<210> SEQ ID NO 13
<211> LENGTH: 16
<212> TYPE: PRT
<213> ORGANISM: Artificial
<220> FEATURE:
<223> OTHER INFORMATION: fragment of hAPOBEC3C

<400> SEQUENCE: 13

Phe Thr Ala Arg Leu Tyr Tyr Phe Gln Tyr Pro Cys Tyr Gln Glu Gly
1               5                   10                  15

<210> SEQ ID NO 14
<211> LENGTH: 16
<212> TYPE: PRT
<213> ORGANISM: Artificial
<220> FEATURE:
<223> OTHER INFORMATION: fragment of hAPOBEC3F - catalytic domain

<400> SEQUENCE: 14

Phe Thr Ala Arg Leu Tyr Tyr Phe Trp Asp Thr Asp Tyr Gln Glu Gly
1               5                   10                  15

<210> SEQ ID NO 15
<211> LENGTH: 15
<212> TYPE: PRT
<213> ORGANISM: Artificial
<220> FEATURE:
<223> OTHER INFORMATION: fragment of hAPOBEC3G - catalytic domain

<400> SEQUENCE: 15

Phe Thr Ala Arg Ile Tyr Asp Asp Gln Gly Arg Cys Gln Glu Gly
1               5                   10                  15

<210> SEQ ID NO 16
<211> LENGTH: 16
<212> TYPE: PRT
<213> ORGANISM: Artificial
<220> FEATURE:
<223> OTHER INFORMATION: fragment of mAPOBEC3 - catalytic domain

<400> SEQUENCE: 16

Phe Ser Ser Arg Leu Tyr Asn Val Gln Asp Pro Glu Thr Gln Gln Asn
1               5                   10                  15

<210> SEQ ID NO 17
<211> LENGTH: 16
<212> TYPE: PRT
<213> ORGANISM: Artificial
<220> FEATURE:
<223> OTHER INFORMATION: fragment of hAPOBEC3H

```
<400> SEQUENCE: 17

Phe Ala Ser Arg Leu Tyr Tyr His Trp Cys Lys Pro Gln Gln Lys Gly
1               5                   10                  15

<210> SEQ ID NO 18
<211> LENGTH: 16
<212> TYPE: PRT
<213> ORGANISM: Artificial
<220> FEATURE:
<223> OTHER INFORMATION: fragment of rAPOBEC1

<400> SEQUENCE: 18

Tyr Ile Ala Arg Leu Tyr His His Ala Asp Pro Arg Asn Arg Gln Gly
1               5                   10                  15

<210> SEQ ID NO 19
<211> LENGTH: 21
<212> TYPE: DNA
<213> ORGANISM: Artificial
<220> FEATURE:
<223> OTHER INFORMATION: EGFP gRNA target sequence

<400> SEQUENCE: 19
tcagctcgat gcggttcacc a                                            21

<210> SEQ ID NO 20
<211> LENGTH: 21
<212> TYPE: DNA
<213> ORGANISM: Artificial
<220> FEATURE:
<223> OTHER INFORMATION: EGFP gRNA target sequence

<400> SEQUENCE: 20
gcagaacacc cccatcggcg a                                            21

<210> SEQ ID NO 21

<400> SEQUENCE: 21

000

<210> SEQ ID NO 22
<211> LENGTH: 24
<212> TYPE: DNA
<213> ORGANISM: Artificial
<220> FEATURE:
<223> OTHER INFORMATION: EGFP gRNA target sequence

<400> SEQUENCE: 22
tcagctcgat gcggttcacc aggg                                         24

<210> SEQ ID NO 23
<211> LENGTH: 20
<212> TYPE: DNA
<213> ORGANISM: Artificial
<220> FEATURE:
<223> OTHER INFORMATION: AAVS1 target site 1 reference sequence

<400> SEQUENCE: 23
gactcaccca ggagtgcgtt                                              20

<210> SEQ ID NO 24
<211> LENGTH: 20
<212> TYPE: DNA
<213> ORGANISM: Artificial
```

```
<220> FEATURE:
<223> OTHER INFORMATION: AAVS1 target site 2 reference sequence

<400> SEQUENCE: 24
gtccgactcg gccaggtcca                                            20

<210> SEQ ID NO 25
<211> LENGTH: 20
<212> TYPE: DNA
<213> ORGANISM: Artificial
<220> FEATURE:
<223> OTHER INFORMATION: AAVS1 target site 3 reference sequence

<400> SEQUENCE: 25
gaccctcagc cgtgctgctc                                            20

<210> SEQ ID NO 26
<211> LENGTH: 20
<212> TYPE: DNA
<213> ORGANISM: Artificial
<220> FEATURE:
<223> OTHER INFORMATION: AAVS1 target site 4 reference sequence

<400> SEQUENCE: 26
gctctcagcc tggagaccac                                            20

<210> SEQ ID NO 27
<211> LENGTH: 20
<212> TYPE: DNA
<213> ORGANISM: Artificial
<220> FEATURE:
<223> OTHER INFORMATION: AAVS1 target site 5 reference sequence

<400> SEQUENCE: 27
gctgactcag agaccctgag                                            20

<210> SEQ ID NO 28
<211> LENGTH: 20
<212> TYPE: DNA
<213> ORGANISM: Artificial
<220> FEATURE:
<223> OTHER INFORMATION: AAVS1 target site 6 reference sequence

<400> SEQUENCE: 28
ggggctcaac atcggaagag                                            20

<210> SEQ ID NO 29
<211> LENGTH: 20
<212> TYPE: DNA
<213> ORGANISM: Artificial
<220> FEATURE:
<223> OTHER INFORMATION: AAVS1 target site 7 reference sequence

<400> SEQUENCE: 29
ggcactcggg ggcgagagga                                            20

<210> SEQ ID NO 30
<211> LENGTH: 20
<212> TYPE: DNA
<213> ORGANISM: Artificial
<220> FEATURE:
<223> OTHER INFORMATION: EMX1 target site 2 reference sequence

<400> SEQUENCE: 30
gtattcacct gaaagtgtgc                                            20
```

```
<210> SEQ ID NO 31
<211> LENGTH: 20
<212> TYPE: DNA
<213> ORGANISM: Artificial
<220> FEATURE:
<223> OTHER INFORMATION: AAVS1 target site 8 reference sequence

<400> SEQUENCE: 31
gagctcactg aacgctggca                                              20

<210> SEQ ID NO 32
<211> LENGTH: 20
<212> TYPE: DNA
<213> ORGANISM: Artificial
<220> FEATURE:
<223> OTHER INFORMATION: AAVS1 target site 9 reference sequence

<400> SEQUENCE: 32
gctggctcag gttcaggaga                                              20

<210> SEQ ID NO 33
<211> LENGTH: 20
<212> TYPE: DNA
<213> ORGANISM: Artificial
<220> FEATURE:
<223> OTHER INFORMATION: FANCF target site 1 reference sequence

<400> SEQUENCE: 33
ggaatccctt ctgcagcacc                                              20

<210> SEQ ID NO 34
<211> LENGTH: 20
<212> TYPE: DNA
<213> ORGANISM: Artificial
<220> FEATURE:
<223> OTHER INFORMATION: EMX1 target site 1 reference sequence

<400> SEQUENCE: 34
gagtccgagc agaagaagaa                                              20

<210> SEQ ID NO 35
<211> LENGTH: 20
<212> TYPE: DNA
<213> ORGANISM: Artificial Sequence
<220> FEATURE:
<223> OTHER INFORMATION: AAVS1 target site 6 reference sequence

<400> SEQUENCE: 35
ggggctcaac atcggaagag                                              20

<210> SEQ ID NO 36
<211> LENGTH: 20
<212> TYPE: DNA
<213> ORGANISM: Artificial
<220> FEATURE:
<223> OTHER INFORMATION: AAVS1 target site 3 reference sequence

<400> SEQUENCE: 36
gaccctcagc cgtgctgctc                                              20

<210> SEQ ID NO 37
<211> LENGTH: 20
<212> TYPE: DNA
<213> ORGANISM: Artificial
<220> FEATURE:
<223> OTHER INFORMATION: AAVS1 target site 7 reference sequence
```

```
<400> SEQUENCE: 37
ggcactcggg ggcgagagga                                              20

<210> SEQ ID NO 38
<211> LENGTH: 20
<212> TYPE: DNA
<213> ORGANISM: Artificial
<220> FEATURE:
<223> OTHER INFORMATION: potential HBB allele products

<400> SEQUENCE: 38
ctgaatttta tgcccagccc                                              20

<210> SEQ ID NO 39
<211> LENGTH: 20
<212> TYPE: DNA
<213> ORGANISM: Artificial
<220> FEATURE:
<223> OTHER INFORMATION: potential HBB allele products

<400> SEQUENCE: 39
ctgagtttta tgcccagccc                                              20

<210> SEQ ID NO 40
<211> LENGTH: 20
<212> TYPE: DNA
<213> ORGANISM: Artificial
<220> FEATURE:
<223> OTHER INFORMATION: potential HBB allele products

<400> SEQUENCE: 40
ctgattttta tgcccagccc                                              20

<210> SEQ ID NO 41
<211> LENGTH: 20
<212> TYPE: DNA
<213> ORGANISM: Artificial
<220> FEATURE:
<223> OTHER INFORMATION: potential HBB allele products

<400> SEQUENCE: 41
ctgacttgta tgcccagccc                                              20

<210> SEQ ID NO 42
<211> LENGTH: 20
<212> TYPE: DNA
<213> ORGANISM: Artificial
<220> FEATURE:
<223> OTHER INFORMATION: potential HBB allele products

<400> SEQUENCE: 42
ctgactttta tgcccagccc                                              20

<210> SEQ ID NO 43
<211> LENGTH: 20
<212> TYPE: DNA
<213> ORGANISM: Artificial
<220> FEATURE:
<223> OTHER INFORMATION: HBB target site reference sequence

<400> SEQUENCE: 43
ctgacttcta tgcccagccc                                              20
```

<210> SEQ ID NO 44
<211> LENGTH: 23
<212> TYPE: DNA
<213> ORGANISM: Artificial
<220> FEATURE:
<223> OTHER INFORMATION: HBB target site reference sequence
<220> FEATURE:
<221> NAME/KEY: misc_feature
<222> LOCATION: (21)..(21)
<223> OTHER INFORMATION: n is a, c, g, or t

<400> SEQUENCE: 44
ctgacttcta tgcccagccc ngg                                           23

<210> SEQ ID NO 45
<211> LENGTH: 83
<212> TYPE: PRT
<213> ORGANISM: Artificial
<220> FEATURE:
<223> OTHER INFORMATION: Uracil glycosylase inhibitor (UGI)

<400> SEQUENCE: 45

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu

<210> SEQ ID NO 46
<211> LENGTH: 4
<212> TYPE: PRT
<213> ORGANISM: Artificial
<220> FEATURE:
<223> OTHER INFORMATION: linker sequence

<400> SEQUENCE: 46

Gly Gly Gly Ser
1

<210> SEQ ID NO 47
<211> LENGTH: 5
<212> TYPE: PRT
<213> ORGANISM: Artificial
<220> FEATURE:
<223> OTHER INFORMATION: linker sequence

<400> SEQUENCE: 47

Gly Gly Gly Gly Ser
1               5

<210> SEQ ID NO 48
<211> LENGTH: 7
<212> TYPE: PRT
<213> ORGANISM: Artificial
<220> FEATURE:
<223> OTHER INFORMATION: SV40 large T antigen NLS -continued

<400> SEQUENCE: 48

Pro Lys Lys Lys Arg Arg Val
1               5

<210> SEQ ID NO 49
<211> LENGTH: 15
<212> TYPE: PRT
<213> ORGANISM: Artificial
<220> FEATURE:
<223> OTHER INFORMATION: nucleoplasmin NLS

<400> SEQUENCE: 49

Lys Arg Pro Ala Ala Thr Lys Lys Ala Gly Gln Ala Lys Lys Lys
1               5                   10                  15

<210> SEQ ID NO 50
<211> LENGTH: 1710
<212> TYPE: PRT
<213> ORGANISM: Artificial
<220> FEATURE:
<223> OTHER INFORMATION: rAPOBEC1-XTEN L8-nCas9-UGI-SV40 NLS

<400> SEQUENCE: 50

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
                20                  25                  30

Arg Lys Glu Thr Cys Leu Leu Tyr Glu Ile Asn Trp Gly Gly Arg His
            35                  40                  45

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
    210                 215                 220

Ala Thr Gly Leu Lys Ser Gly Ser Glu Thr Pro Gly Thr Ser Glu Ser
225                 230                 235                 240

Ala Thr Pro Glu Ser Asp Lys Lys Tyr Ser Ile Gly Leu Ala Ile Gly
                245                 250                 255

Thr Asn Ser Val Gly Trp Ala Val Ile Thr Asp Glu Tyr Lys Val Pro
            260                 265                 270

-continued

```
Ser Lys Lys Phe Lys Val Leu Gly Asn Thr Asp Arg His Ser Ile Lys
            275                 280                 285
Lys Asn Leu Ile Gly Ala Leu Leu Phe Asp Ser Gly Glu Thr Ala Glu
290                 295                 300
Ala Thr Arg Leu Lys Arg Thr Ala Arg Arg Tyr Thr Arg Arg Lys
305                 310                 315                 320
Asn Arg Ile Cys Tyr Leu Gln Glu Ile Phe Ser Asn Glu Met Ala Lys
                325                 330                 335
Val Asp Asp Ser Phe Phe His Arg Leu Glu Glu Ser Phe Leu Val Glu
            340                 345                 350
Glu Asp Lys Lys His Glu Arg His Pro Ile Phe Gly Asn Ile Val Asp
            355                 360                 365
Glu Val Ala Tyr His Glu Lys Tyr Pro Thr Ile Tyr His Leu Arg Lys
370                 375                 380
Lys Leu Val Asp Ser Thr Asp Lys Ala Asp Leu Arg Leu Ile Tyr Leu
385                 390                 395                 400
Ala Leu Ala His Met Ile Lys Phe Arg Gly His Phe Leu Ile Glu Gly
                405                 410                 415
Asp Leu Asn Pro Asp Asn Ser Asp Val Asp Lys Leu Phe Ile Gln Leu
            420                 425                 430
Val Gln Thr Tyr Asn Gln Leu Phe Glu Glu Asn Pro Ile Asn Ala Ser
            435                 440                 445
Gly Val Asp Ala Lys Ala Ile Leu Ser Ala Arg Leu Ser Lys Ser Arg
450                 455                 460
Arg Leu Glu Asn Leu Ile Ala Gln Leu Pro Gly Glu Lys Lys Asn Gly
465                 470                 475                 480
Leu Phe Gly Asn Leu Ile Ala Leu Ser Leu Gly Leu Thr Pro Asn Phe
                485                 490                 495
Lys Ser Asn Phe Asp Leu Ala Glu Asp Ala Lys Leu Gln Leu Ser Lys
            500                 505                 510
Asp Thr Tyr Asp Asp Asp Leu Asp Asn Leu Leu Ala Gln Ile Gly Asp
            515                 520                 525
Gln Tyr Ala Asp Leu Phe Leu Ala Ala Lys Asn Leu Ser Asp Ala Ile
530                 535                 540
Leu Leu Ser Asp Ile Leu Arg Val Asn Thr Glu Ile Thr Lys Ala Pro
545                 550                 555                 560
Leu Ser Ala Ser Met Ile Lys Arg Tyr Asp Glu His His Gln Asp Leu
                565                 570                 575
Thr Leu Leu Lys Ala Leu Val Arg Gln Gln Leu Pro Glu Lys Tyr Lys
            580                 585                 590
Glu Ile Phe Phe Asp Gln Ser Lys Asn Gly Tyr Ala Gly Tyr Ile Asp
            595                 600                 605
Gly Gly Ala Ser Gln Glu Glu Phe Tyr Lys Phe Ile Lys Pro Ile Leu
610                 615                 620
Glu Lys Met Asp Gly Thr Glu Glu Leu Leu Val Lys Leu Asn Arg Glu
625                 630                 635                 640
Asp Leu Leu Arg Lys Gln Arg Thr Phe Asp Asn Gly Ser Ile Pro His
                645                 650                 655
Gln Ile His Leu Gly Glu Leu His Ala Ile Leu Arg Arg Gln Glu Asp
            660                 665                 670
Phe Tyr Pro Phe Leu Lys Asp Asn Arg Glu Lys Ile Glu Lys Ile Leu
            675                 680                 685
```

```
Thr Phe Arg Ile Pro Tyr Tyr Val Gly Pro Leu Ala Arg Gly Asn Ser
690                 695                 700

Arg Phe Ala Trp Met Thr Arg Lys Ser Glu Glu Thr Ile Thr Pro Trp
705                 710                 715                 720

Asn Phe Glu Glu Val Val Asp Lys Gly Ala Ser Ala Gln Ser Phe Ile
            725                 730                 735

Glu Arg Met Thr Asn Phe Asp Lys Asn Leu Pro Asn Glu Lys Val Leu
            740                 745                 750

Pro Lys His Ser Leu Leu Tyr Glu Tyr Phe Thr Val Tyr Asn Glu Leu
            755                 760                 765

Thr Lys Val Lys Tyr Val Thr Glu Gly Met Arg Lys Pro Ala Phe Leu
770                 775                 780

Ser Gly Glu Gln Lys Lys Ala Ile Val Asp Leu Leu Phe Lys Thr Asn
785                 790                 795                 800

Arg Lys Val Thr Val Lys Gln Leu Lys Glu Asp Tyr Phe Lys Lys Ile
            805                 810                 815

Glu Cys Phe Asp Ser Val Glu Ile Ser Gly Val Glu Asp Arg Phe Asn
            820                 825                 830

Ala Ser Leu Gly Thr Tyr His Asp Leu Leu Lys Ile Ile Lys Asp Lys
            835                 840                 845

Asp Phe Leu Asp Asn Glu Glu Asn Glu Asp Ile Leu Glu Asp Ile Val
850                 855                 860

Leu Thr Leu Thr Leu Phe Glu Asp Arg Glu Met Ile Glu Glu Arg Leu
865                 870                 875                 880

Lys Thr Tyr Ala His Leu Phe Asp Asp Lys Val Met Lys Gln Leu Lys
            885                 890                 895

Arg Arg Arg Tyr Thr Gly Trp Gly Arg Leu Ser Arg Lys Leu Ile Asn
            900                 905                 910

Gly Ile Arg Asp Lys Gln Ser Gly Lys Thr Ile Leu Asp Phe Leu Lys
            915                 920                 925

Ser Asp Gly Phe Ala Asn Arg Asn Phe Met Gln Leu Ile His Asp Asp
930                 935                 940

Ser Leu Thr Phe Lys Glu Asp Ile Gln Lys Ala Gln Val Ser Gly Gln
945                 950                 955                 960

Gly Asp Ser Leu His Glu His Ile Ala Asn Leu Ala Gly Ser Pro Ala
            965                 970                 975

Ile Lys Lys Gly Ile Leu Gln Thr Val Lys Val Val Asp Glu Leu Val
            980                 985                 990

Lys Val Met Gly Arg His Lys Pro Glu Asn Ile Val Ile Glu Met Ala
995                 1000                1005

Arg Glu Asn Gln Thr Thr Gln Lys Gly Gln Lys Asn Ser Arg Glu
    1010                1015                1020

Arg Met Lys Arg Ile Glu Glu Gly Ile Lys Glu Leu Gly Ser Gln
    1025                1030                1035

Ile Leu Lys Glu His Pro Val Glu Asn Thr Gln Leu Gln Asn Glu
    1040                1045                1050

Lys Leu Tyr Leu Tyr Tyr Leu Gln Asn Gly Arg Asp Met Tyr Val
    1055                1060                1065

Asp Gln Glu Leu Asp Ile Asn Arg Leu Ser Asp Tyr Asp Val Asp
    1070                1075                1080

His Ile Val Pro Gln Ser Phe Leu Lys Asp Asp Ser Ile Asp Asn
    1085                1090                1095
```

-continued

```
Lys Val Leu Thr Arg Ser Asp Lys Asn Arg Gly Lys Ser Asp Asn
    1100                1105                1110
Val Pro Ser Glu Glu Val Val Lys Lys Met Lys Asn Tyr Trp Arg
    1115                1120                1125
Gln Leu Leu Asn Ala Lys Leu Ile Thr Gln Arg Lys Phe Asp Asn
    1130                1135                1140
Leu Thr Lys Ala Glu Arg Gly Gly Leu Ser Glu Leu Asp Lys Ala
    1145                1150                1155
Gly Phe Ile Lys Arg Gln Leu Val Glu Thr Arg Gln Ile Thr Lys
    1160                1165                1170
His Val Ala Gln Ile Leu Asp Ser Arg Met Asn Thr Lys Tyr Asp
    1175                1180                1185
Glu Asn Asp Lys Leu Ile Arg Glu Val Lys Val Ile Thr Leu Lys
    1190                1195                1200
Ser Lys Leu Val Ser Asp Phe Arg Lys Asp Phe Gln Phe Tyr Lys
    1205                1210                1215
Val Arg Glu Ile Asn Asn Tyr His His Ala His Asp Ala Tyr Leu
    1220                1225                1230
Asn Ala Val Val Gly Thr Ala Leu Ile Lys Lys Tyr Pro Lys Leu
    1235                1240                1245
Glu Ser Glu Phe Val Tyr Gly Asp Tyr Lys Val Tyr Asp Val Arg
    1250                1255                1260
Lys Met Ile Ala Lys Ser Glu Gln Glu Ile Gly Lys Ala Thr Ala
    1265                1270                1275
Lys Tyr Phe Phe Tyr Ser Asn Ile Met Asn Phe Phe Lys Thr Glu
    1280                1285                1290
Ile Thr Leu Ala Asn Gly Glu Ile Arg Lys Arg Pro Leu Ile Glu
    1295                1300                1305
Thr Asn Gly Glu Thr Gly Glu Ile Val Trp Asp Lys Gly Arg Asp
    1310                1315                1320
Phe Ala Thr Val Arg Lys Val Leu Ser Met Pro Gln Val Asn Ile
    1325                1330                1335
Val Lys Lys Thr Glu Val Gln Thr Gly Gly Phe Ser Lys Glu Ser
    1340                1345                1350
Ile Leu Pro Lys Arg Asn Ser Asp Lys Leu Ile Ala Arg Lys Lys
    1355                1360                1365
Asp Trp Asp Pro Lys Lys Tyr Gly Gly Phe Asp Ser Pro Thr Val
    1370                1375                1380
Ala Tyr Ser Val Leu Val Val Ala Lys Val Glu Lys Gly Lys Ser
    1385                1390                1395
Lys Lys Leu Lys Ser Val Lys Glu Leu Leu Gly Ile Thr Ile Met
    1400                1405                1410
Glu Arg Ser Ser Phe Glu Lys Asn Pro Ile Asp Phe Leu Glu Ala
    1415                1420                1425
Lys Gly Tyr Lys Glu Val Lys Lys Asp Leu Ile Ile Lys Leu Pro
    1430                1435                1440
Lys Tyr Ser Leu Phe Glu Leu Glu Asn Gly Arg Lys Arg Met Leu
    1445                1450                1455
Ala Ser Ala Gly Glu Leu Gln Lys Gly Asn Glu Leu Ala Leu Pro
    1460                1465                1470
Ser Lys Tyr Val Asn Phe Leu Tyr Leu Ala Ser His Tyr Glu Lys
    1475                1480                1485
```

```
Leu Lys Gly Ser Pro Glu Asp Asn Glu Gln Lys Gln Leu Phe Val
    1490                1495                1500

Glu Gln His Lys His Tyr Leu Asp Glu Ile Ile Glu Gln Ile Ser
    1505                1510                1515

Glu Phe Ser Lys Arg Val Ile Leu Ala Asp Ala Asn Leu Asp Lys
    1520                1525                1530

Val Leu Ser Ala Tyr Asn Lys His Arg Asp Lys Pro Ile Arg Glu
    1535                1540                1545

Gln Ala Glu Asn Ile Ile His Leu Phe Thr Leu Thr Asn Leu Gly
    1550                1555                1560

Ala Pro Ala Ala Phe Lys Tyr Phe Asp Thr Thr Ile Asp Arg Lys
    1565                1570                1575

Arg Tyr Thr Ser Thr Lys Glu Val Leu Asp Ala Thr Leu Ile His
    1580                1585                1590

Gln Ser Ile Thr Gly Leu Tyr Glu Thr Arg Ile Asp Leu Ser Gln
    1595                1600                1605

Leu Gly Gly Asp Ser Gly Gly Ser Thr Asn Leu Ser Asp Ile Ile
    1610                1615                1620

Glu Lys Glu Thr Gly Lys Gln Leu Val Ile Gln Glu Ser Ile Leu
    1625                1630                1635

Met Leu Pro Glu Glu Val Glu Glu Val Ile Gly Asn Lys Pro Glu
    1640                1645                1650

Ser Asp Ile Leu Val His Thr Ala Tyr Asp Glu Ser Thr Asp Glu
    1655                1660                1665

Asn Val Met Leu Leu Thr Ser Asp Ala Pro Glu Tyr Lys Pro Trp
    1670                1675                1680

Ala Leu Val Ile Gln Asp Ser Asn Gly Glu Asn Lys Ile Lys Met
    1685                1690                1695

Leu Ser Gly Gly Ser Pro Lys Lys Lys Arg Lys Val
    1700                1705                1710

<210> SEQ ID NO 51
<211> LENGTH: 198
<212> TYPE: PRT
<213> ORGANISM: Homo sapiens

<400> SEQUENCE: 51

Met Asp Ser Leu Leu Met Asn Arg Arg Lys Phe Leu Tyr Gln Phe Lys
  1               5                  10                  15

Asn Val Arg Trp Ala Lys Gly Arg Arg Glu Thr Tyr Leu Cys Tyr Val
                 20                  25                  30

Val Lys Arg Arg Asp Ser Ala Thr Ser Phe Ser Leu Asp Phe Gly Tyr
             35                  40                  45

Leu Arg Asn Lys Asn Gly Cys His Val Glu Leu Leu Phe Leu Arg Tyr
         50                  55                  60

Ile Ser Asp Trp Asp Leu Asp Pro Gly Arg Cys Tyr Arg Val Thr Trp
 65                  70                  75                  80

Phe Thr Ser Trp Ser Pro Cys Tyr Asp Cys Ala Arg His Val Ala Asp
                 85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140
```

```
Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
            165                 170                 175

Arg Arg Ile Leu Leu Pro Leu Tyr Glu Val Asp Asp Leu Arg Asp Ala
            180                 185                 190

Phe Arg Thr Leu Gly Leu
            195

<210> SEQ ID NO 52
<211> LENGTH: 190
<212> TYPE: PRT
<213> ORGANISM: Artificial
<220> FEATURE:
<223> OTHER INFORMATION: hAIDv solubility variant lacking N-terminal
      RNA-binding region

<400> SEQUENCE: 52

Met Asp Pro His Ile Phe Thr Ser Asn Phe Asn Asn Gly Ile Gly Arg
1               5                   10                  15

His Lys Thr Tyr Leu Cys Tyr Glu Val Glu Arg Leu Asp Ser Ala Thr
            20                  25                  30

Ser Phe Ser Leu Asp Phe Gly Tyr Leu Arg Asn Lys Asn Gly Cys His
        35                  40                  45

Val Glu Leu Leu Phe Leu Arg Tyr Ile Ser Asp Trp Asp Leu Asp Pro
50                  55                  60

Gly Arg Cys Tyr Arg Val Thr Trp Phe Thr Ser Trp Ser Pro Cys Tyr
65                  70                  75                  80

Asp Cys Ala Arg His Val Ala Asp Phe Leu Arg Gly Asn Pro Asn Leu
                85                  90                  95

Ser Leu Arg Ile Phe Thr Ala Arg Leu Tyr Phe Cys Glu Asp Arg Lys
            100                 105                 110

Ala Glu Pro Glu Gly Leu Arg Arg Leu His Arg Ala Gly Val Gln Ile
        115                 120                 125

Ala Ile Met Thr Phe Lys Asp Tyr Phe Tyr Cys Trp Asn Thr Phe Val
130                 135                 140

Glu Asn His Glu Arg Thr Phe Lys Ala Trp Glu Gly Leu His Glu Asn
145                 150                 155                 160

Ser Val Arg Leu Ser Arg Gln Leu Arg Arg Ile Leu Leu Pro Leu Tyr
            165                 170                 175

Glu Val Asp Asp Leu Arg Asp Ala Phe Arg Thr Leu Gly Leu
            180                 185                 190

<210> SEQ ID NO 53
<211> LENGTH: 175
<212> TYPE: PRT
<213> ORGANISM: Artificial
<220> FEATURE:
<223> OTHER INFORMATION: hAIDv solubility variant lacking N-terminal
      RNA-binding region and the C-terminal poorly structured region

<400> SEQUENCE: 53

Met Asp Pro His Ile Phe Thr Ser Asn Phe Asn Asn Gly Ile Gly Arg
1               5                   10                  15

His Lys Thr Tyr Leu Cys Tyr Glu Val Glu Arg Leu Asp Ser Ala Thr
            20                  25                  30

Ser Phe Ser Leu Asp Phe Gly Tyr Leu Arg Asn Lys Asn Gly Cys His
        35                  40                  45
```

Val Glu Leu Leu Phe Leu Arg Tyr Ile Ser Asp Trp Asp Leu Asp Pro
 50                  55                  60

Gly Arg Cys Tyr Arg Val Thr Trp Phe Thr Ser Trp Ser Pro Cys Tyr
 65                  70                  75                  80

Asp Cys Ala Arg His Val Ala Asp Phe Leu Arg Gly Asn Pro Asn Leu
                 85                  90                  95

Ser Leu Arg Ile Phe Thr Ala Arg Leu Tyr Phe Cys Glu Asp Arg Lys
                100                 105                 110

Ala Glu Pro Glu Gly Leu Arg Leu His Arg Ala Gly Val Gln Ile
                115                 120                 125

Ala Ile Met Thr Phe Lys Asp Tyr Phe Tyr Cys Trp Asn Thr Phe Val
130                 135                 140

Glu Asn His Glu Arg Thr Phe Lys Ala Trp Glu Gly Leu His Glu Asn
145                 150                 155                 160

Ser Val Arg Leu Ser Arg Gln Leu Arg Arg Ile Leu Leu Pro Leu
                165                 170                 175

<210> SEQ ID NO 54
<211> LENGTH: 229
<212> TYPE: PRT
<213> ORGANISM: Rattus norvegicus

<400> SEQUENCE: 54

Met Ser Ser Glu Thr Gly Pro Val Ala Val Asp Pro Thr Leu Arg Arg
 1               5                  10                  15

Arg Ile Glu Pro His Glu Phe Glu Val Phe Asp Pro Arg Glu Leu
                 20                  25                  30

Arg Lys Glu Thr Cys Leu Leu Tyr Glu Ile Asn Trp Gly Gly Arg His
                 35                  40                  45

Ser Ile Trp Arg His Thr Ser Gln Asn Thr Asn Lys His Val Glu Val
 50                  55                  60

Asn Phe Ile Glu Lys Phe Thr Thr Glu Arg Tyr Phe Cys Pro Asn Thr
 65                  70                  75                  80

Arg Cys Ser Ile Thr Trp Phe Leu Ser Trp Ser Pro Cys Gly Glu Cys
                 85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Arg Asn Arg
                115                 120                 125

Gln Gly Leu Arg Asp Leu Ile Ser Ser Gly Val Thr Ile Gln Ile Met
                130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
                180                 185                 190

Leu Asn Ile Leu Arg Arg Lys Gln Pro Gln Leu Thr Phe Phe Thr Ile
                195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 55
<211> LENGTH: 397
<212> TYPE: PRT
<213> ORGANISM: Mus musculus

<400> SEQUENCE: 55

Met Gly Pro Phe Cys Leu Gly Cys Ser His Arg Lys Cys Tyr Ser Pro
1               5                   10                  15

Ile Arg Asn Leu Ile Ser Gln Glu Thr Phe Lys Phe His Phe Lys Asn
            20                  25                  30

Leu Gly Tyr Ala Lys Gly Arg Lys Asp Thr Phe Leu Cys Tyr Glu Val
        35                  40                  45

Thr Arg Lys Asp Cys Asp Ser Pro Val Ser Leu His His Gly Val Phe
    50                  55                  60

Lys Asn Lys Asp Asn Ile His Ala Glu Ile Cys Phe Leu Tyr Trp Phe
65                  70                  75                  80

His Asp Lys Val Leu Lys Val Leu Ser Pro Arg Glu Phe Lys Ile
            85                  90                  95

Thr Trp Tyr Met Ser Trp Ser Pro Cys Phe Glu Cys Ala Glu Gln Ile
            100                 105                 110

Val Arg Phe Leu Ala Thr His His Asn Leu Ser Leu Asp Ile Phe Ser
        115                 120                 125

Ser Arg Leu Tyr Asn Val Gln Asp Pro Glu Thr Gln Gln Asn Leu Cys
    130                 135                 140

Arg Leu Val Gln Glu Gly Ala Gln Val Ala Ala Met Asp Leu Tyr Glu
145                 150                 155                 160

Phe Lys Lys Cys Trp Lys Lys Phe Val Asp Asn Gly Gly Arg Arg Phe
            165                 170                 175

Arg Pro Trp Lys Arg Leu Leu Thr Asn Phe Arg Tyr Gln Asp Ser Lys
        180                 185                 190

Leu Gln Glu Ile Leu Arg Arg Met Asp Pro Leu Ser Glu Glu Glu Phe
    195                 200                 205

Tyr Ser Gln Phe Tyr Asn Gln Arg Val Lys His Leu Cys Tyr Tyr His
    210                 215                 220

Arg Met Lys Pro Tyr Leu Cys Tyr Gln Leu Glu Gln Phe Asn Gly Gln
225                 230                 235                 240

Ala Pro Leu Lys Gly Cys Leu Leu Ser Glu Lys Gly Lys Gln His Ala
            245                 250                 255

Glu Ile Leu Phe Leu Asp Lys Ile Arg Ser Met Glu Leu Ser Gln Val
        260                 265                 270

Thr Ile Thr Cys Tyr Leu Thr Trp Ser Pro Cys Pro Asn Cys Ala Trp
    275                 280                 285

Gln Leu Ala Ala Phe Lys Arg Asp Arg Pro Asp Leu Ile Leu His Ile
    290                 295                 300

Tyr Thr Ser Arg Leu Tyr Phe His Trp Lys Arg Pro Phe Gln Lys Gly
305                 310                 315                 320

Leu Cys Ser Leu Trp Gln Ser Gly Ile Leu Val Asp Val Met Asp Leu
            325                 330                 335

Pro Gln Phe Thr Asp Cys Trp Thr Asn Phe Val Asn Pro Lys Arg Pro
        340                 345                 350

Phe Arg Pro Trp Lys Gly Leu Glu Ile Ile Ser Arg Arg Thr Gln Arg
    355                 360                 365

Arg Leu Arg Arg Ile Lys Glu Ser Trp Gly Leu Gln Asp Leu Val Asn
            370                 375                 380

Asp Phe Gly Asn Leu Gln Leu Gly Pro Pro Met Ser Asn
385                 390                 395

<210> SEQ ID NO 56
<211> LENGTH: 199
<212> TYPE: PRT
<213> ORGANISM: Artificial
<220> FEATURE:
<223> OTHER INFORMATION: mAPOBEC3 catalytic domain

<400> SEQUENCE: 56

Met Gly Pro Phe Cys Leu Gly Cys Ser His Arg Lys Cys Tyr Ser Pro
1               5                   10                  15

Ile Arg Asn Leu Ile Ser Gln Glu Thr Phe Lys Phe His Phe Lys Asn
            20                  25                  30

Leu Gly Tyr Ala Lys Gly Arg Lys Asp Thr Phe Leu Cys Tyr Glu Val
        35                  40                  45

Thr Arg Lys Asp Cys Asp Ser Pro Val Ser Leu His His Gly Val Phe
    50                  55                  60

Lys Asn Lys Asp Asn Ile His Ala Glu Ile Cys Phe Leu Tyr Trp Phe
65                  70                  75                  80

His Asp Lys Val Leu Lys Val Leu Ser Pro Arg Glu Glu Phe Lys Ile
                85                  90                  95

Thr Trp Tyr Met Ser Trp Ser Pro Cys Phe Glu Cys Ala Glu Gln Ile
            100                 105                 110

Val Arg Phe Leu Ala Thr His His Asn Leu Ser Leu Asp Ile Phe Ser
        115                 120                 125

Ser Arg Leu Tyr Asn Val Gln Asp Pro Glu Thr Gln Gln Asn Leu Cys
    130                 135                 140

Arg Leu Val Gln Glu Gly Ala Gln Val Ala Ala Met Asp Leu Tyr Glu
145                 150                 155                 160

Phe Lys Lys Cys Trp Lys Lys Phe Val Asp Asn Gly Gly Arg Arg Phe
                165                 170                 175

Arg Pro Trp Lys Arg Leu Leu Thr Asn Phe Arg Tyr Gln Asp Ser Lys
            180                 185                 190

Leu Gln Glu Ile Leu Arg Arg
        195

<210> SEQ ID NO 57
<211> LENGTH: 199
<212> TYPE: PRT
<213> ORGANISM: Homo sapiens

<400> SEQUENCE: 57

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

```
Ser Leu Gln Leu Asp Pro Ala Gln Ile Tyr Arg Val Thr Trp Phe Ile
             85                  90                  95

Ser Trp Ser Pro Cys Phe Ser Trp Gly Cys Ala Gly Glu Val Arg Ala
        100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
        130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
            195

<210> SEQ ID NO 58
<211> LENGTH: 384
<212> TYPE: PRT
<213> ORGANISM: Homo sapiens

<400> SEQUENCE: 58

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125

Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255
```

```
His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
                340                 345                 350

His Gln Gly Cys Pro Phe Gln Pro Trp Asp Gly Leu Asp Glu His Ser
            355                 360                 365

Gln Asp Leu Ser Gly Arg Leu Arg Ala Ile Leu Gln Asn Gln Glu Asn
        370                 375                 380

<210> SEQ ID NO 59
<211> LENGTH: 186
<212> TYPE: PRT
<213> ORGANISM: Artificial
<220> FEATURE:
<223> OTHER INFORMATION: hAPOBEC3G catalytic domain

<400> SEQUENCE: 59

Pro Pro Thr Phe Thr Phe Asn Phe Asn Asn Glu Pro Trp Val Arg Gly
1               5                   10                  15

Arg His Glu Thr Tyr Leu Cys Tyr Glu Val Glu Arg Met His Asn Asp
            20                  25                  30

Thr Trp Val Leu Leu Asn Gln Arg Arg Gly Phe Leu Cys Asn Gln Ala
        35                  40                  45

Pro His Lys His Gly Phe Leu Glu Gly Arg His Ala Glu Leu Cys Phe
    50                  55                  60

Leu Asp Val Ile Pro Phe Trp Lys Leu Asp Leu Asp Gln Asp Tyr Arg
65                  70                  75                  80

Val Thr Cys Phe Thr Ser Trp Ser Pro Cys Phe Ser Cys Ala Gln Glu
                85                  90                  95

Met Ala Lys Phe Ile Ser Lys Asn Lys His Val Ser Leu Cys Ile Phe
            100                 105                 110

Thr Ala Arg Ile Tyr Asp Asp Gln Gly Arg Cys Gln Glu Gly Leu Arg
        115                 120                 125

Thr Leu Ala Glu Ala Gly Ala Lys Ile Ser Ile Met Thr Tyr Ser Glu
    130                 135                 140

Phe Lys His Cys Trp Asp Thr Phe Val Asp His Gln Gly Cys Pro Phe
145                 150                 155                 160

Gln Pro Trp Asp Gly Leu Asp Glu His Ser Gln Asp Leu Ser Gly Arg
                165                 170                 175

Leu Arg Ala Ile Leu Gln Asn Gln Glu Asn
            180                 185

<210> SEQ ID NO 60
<211> LENGTH: 200
<212> TYPE: PRT
<213> ORGANISM: Homo sapiens
```

<400> SEQUENCE: 60

```
Met Ala Leu Leu Thr Ala Glu Thr Phe Arg Leu Gln Phe Asn Asn Lys
1               5                   10                  15

Arg Arg Leu Arg Arg Pro Tyr Tyr Pro Arg Lys Ala Leu Leu Cys Tyr
            20                  25                  30

Gln Leu Thr Pro Gln Asn Gly Ser Thr Pro Thr Arg Gly Tyr Phe Glu
        35                  40                  45

Asn Lys Lys Lys Cys His Ala Glu Ile Cys Phe Ile Asn Glu Ile Lys
50                  55                  60

Ser Met Gly Leu Asp Glu Thr Gln Cys Tyr Gln Val Thr Cys Tyr Leu
65                  70                  75                  80

Thr Trp Ser Pro Cys Ser Ser Cys Ala Trp Glu Leu Val Asp Phe Ile
                85                  90                  95

Lys Ala His Asp His Leu Asn Leu Gly Ile Phe Ala Ser Arg Leu Tyr
            100                 105                 110

Tyr His Trp Cys Lys Pro Gln Gln Lys Gly Leu Arg Leu Leu Cys Gly
        115                 120                 125

Ser Gln Val Pro Val Glu Val Met Gly Phe Pro Lys Phe Ala Asp Cys
130                 135                 140

Trp Glu Asn Phe Val Asp His Glu Lys Pro Leu Ser Phe Asn Pro Tyr
145                 150                 155                 160

Lys Met Leu Glu Glu Leu Asp Lys Asn Ser Arg Ala Ile Lys Arg Arg
                165                 170                 175

Leu Glu Arg Ile Lys Ile Pro Gly Val Arg Ala Gln Gly Arg Tyr Met
            180                 185                 190

Asp Ile Leu Cys Asp Ala Glu Val
        195                 200
```

<210> SEQ ID NO 61
<211> LENGTH: 373
<212> TYPE: PRT
<213> ORGANISM: Homo sapiens

<400> SEQUENCE: 61

```
Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Arg
        35                  40                  45

Leu Asp Ala Lys Ile Phe Arg Gly Gln Val Tyr Ser Gln Pro Glu His
50                  55                  60

His Ala Glu Met Cys Phe Leu Ser Trp Phe Cys Gly Asn Gln Leu Pro
65                  70                  75                  80

Ala Tyr Lys Cys Phe Gln Ile Thr Trp Phe Val Ser Trp Thr Pro Cys
                85                  90                  95

Pro Asp Cys Val Ala Lys Leu Ala Glu Phe Leu Ala Glu His Pro Asn
            100                 105                 110

Val Thr Leu Thr Ile Ser Ala Ala Arg Leu Tyr Tyr Tyr Trp Glu Arg
        115                 120                 125

Asp Tyr Arg Arg Ala Leu Cys Arg Leu Ser Gln Ala Gly Ala Arg Val
130                 135                 140

Lys Ile Met Asp Asp Glu Glu Phe Ala Tyr Cys Trp Glu Asn Phe Val
145                 150                 155                 160
```

Tyr Ser Glu Gly Gln Pro Phe Met Pro Trp Tyr Lys Phe Asp Asp Asn
                    165                 170                 175

Tyr Ala Phe Leu His Arg Thr Leu Lys Glu Ile Leu Arg Asn Pro Met
            180                 185                 190

Glu Ala Met Tyr Pro His Ile Phe Tyr Phe His Phe Lys Asn Leu Arg
        195                 200                 205

Lys Ala Tyr Gly Arg Asn Glu Ser Trp Leu Cys Phe Thr Met Glu Val
    210                 215                 220

Val Lys His His Ser Pro Val Ser Trp Lys Arg Gly Val Phe Arg Asn
225                 230                 235                 240

Gln Val Asp Pro Glu Thr His Cys His Ala Glu Arg Cys Phe Leu Ser
                245                 250                 255

Trp Phe Cys Asp Asp Ile Leu Ser Pro Asn Thr Asn Tyr Glu Val Thr
            260                 265                 270

Trp Tyr Thr Ser Trp Ser Pro Cys Pro Glu Cys Ala Gly Glu Val Ala
        275                 280                 285

Glu Phe Leu Ala Arg His Ser Asn Val Asn Leu Thr Ile Phe Thr Ala
    290                 295                 300

Arg Leu Tyr Tyr Phe Trp Asp Thr Asp Tyr Gln Glu Gly Leu Arg Ser
305                 310                 315                 320

Leu Ser Gln Glu Gly Ala Ser Val Glu Ile Met Gly Tyr Lys Asp Phe
                325                 330                 335

Lys Tyr Cys Trp Glu Asn Phe Val Tyr Asn Asp Asp Glu Pro Phe Lys
            340                 345                 350

Pro Trp Lys Gly Leu Lys Tyr Asn Phe Leu Phe Leu Asp Ser Lys Leu
        355                 360                 365

Gln Glu Ile Leu Glu
    370

<210> SEQ ID NO 62
<211> LENGTH: 189
<212> TYPE: PRT
<213> ORGANISM: Artificial
<220> FEATURE:
<223> OTHER INFORMATION: hAPOBEC3F catalytic domain

<400> SEQUENCE: 62

Lys Glu Ile Leu Arg Asn Pro Met Glu Ala Met Tyr Pro His Ile Phe
1               5                   10                  15

Tyr Phe His Phe Lys Asn Leu Arg Lys Ala Tyr Gly Arg Asn Glu Ser
            20                  25                  30

Trp Leu Cys Phe Thr Met Glu Val Val Lys His His Ser Pro Val Ser
        35                  40                  45

Trp Lys Arg Gly Val Phe Arg Asn Gln Val Asp Pro Glu Thr His Cys
    50                  55                  60

His Ala Glu Arg Cys Phe Leu Ser Trp Phe Cys Asp Asp Ile Leu Ser
65                  70                  75                  80

Pro Asn Thr Asn Tyr Glu Val Thr Trp Tyr Thr Ser Trp Ser Pro Cys
                85                  90                  95

Pro Glu Cys Ala Gly Glu Val Ala Glu Phe Leu Ala Arg His Ser Asn
            100                 105                 110

Val Asn Leu Thr Ile Phe Thr Ala Arg Leu Tyr Tyr Phe Trp Asp Thr
        115                 120                 125

Asp Tyr Gln Glu Gly Leu Arg Ser Leu Ser Gln Glu Gly Ala Ser Val
    130                 135                 140

```
Glu Ile Met Gly Tyr Lys Asp Phe Lys Tyr Cys Trp Glu Asn Phe Val
145                 150                 155                 160

Tyr Asn Asp Asp Glu Pro Phe Lys Pro Trp Lys Gly Leu Lys Tyr Asn
                165                 170                 175

Phe Leu Phe Leu Asp Ser Lys Leu Gln Glu Ile Leu Glu
            180                 185

<210> SEQ ID NO 63
<211> LENGTH: 1053
<212> TYPE: PRT
<213> ORGANISM: Staphylococcus aureus

<400> SEQUENCE: 63

Met Lys Arg Asn Tyr Ile Leu Gly Leu Asp Ile Gly Ile Thr Ser Val
1               5                   10                  15

Gly Tyr Gly Ile Ile Asp Tyr Glu Thr Arg Asp Val Ile Asp Ala Gly
            20                  25                  30

Val Arg Leu Phe Lys Glu Ala Asn Val Glu Asn Asn Glu Gly Arg Arg
        35                  40                  45

Ser Lys Arg Gly Ala Arg Arg Leu Lys Arg Arg Arg Arg His Arg Ile
50                  55                  60

Gln Arg Val Lys Lys Leu Leu Phe Asp Tyr Asn Leu Leu Thr Asp His
65                  70                  75                  80

Ser Glu Leu Ser Gly Ile Asn Pro Tyr Glu Ala Arg Val Lys Gly Leu
                85                  90                  95

Ser Gln Lys Leu Ser Glu Glu Glu Phe Ser Ala Ala Leu Leu His Leu
            100                 105                 110

Ala Lys Arg Arg Gly Val His Asn Val Asn Glu Val Glu Glu Asp Thr
        115                 120                 125

Gly Asn Glu Leu Ser Thr Lys Glu Gln Ile Ser Arg Asn Ser Lys Ala
130                 135                 140

Leu Glu Glu Lys Tyr Val Ala Glu Leu Gln Leu Glu Arg Leu Lys Lys
145                 150                 155                 160

Asp Gly Glu Val Arg Gly Ser Ile Asn Arg Phe Lys Thr Ser Asp Tyr
                165                 170                 175

Val Lys Glu Ala Lys Gln Leu Leu Lys Val Gln Lys Ala Tyr His Gln
            180                 185                 190

Leu Asp Gln Ser Phe Ile Asp Thr Tyr Ile Asp Leu Leu Glu Thr Arg
        195                 200                 205

Arg Thr Tyr Tyr Glu Gly Pro Gly Glu Gly Ser Pro Phe Gly Trp Lys
210                 215                 220

Asp Ile Lys Glu Trp Tyr Glu Met Leu Met Gly His Cys Thr Tyr Phe
225                 230                 235                 240

Pro Glu Glu Leu Arg Ser Val Lys Tyr Ala Tyr Asn Ala Asp Leu Tyr
                245                 250                 255

Asn Ala Leu Asn Asp Leu Asn Asn Leu Val Ile Thr Arg Asp Glu Asn
            260                 265                 270

Glu Lys Leu Glu Tyr Tyr Glu Lys Phe Gln Ile Ile Glu Asn Val Phe
        275                 280                 285

Lys Gln Lys Lys Lys Pro Thr Leu Lys Gln Ile Ala Lys Glu Ile Leu
290                 295                 300

Val Asn Glu Glu Asp Ile Lys Gly Tyr Arg Val Thr Ser Thr Gly Lys
305                 310                 315                 320

Pro Glu Phe Thr Asn Leu Lys Val Tyr His Asp Ile Lys Asp Ile Thr
                325                 330                 335
```

```
Ala Arg Lys Glu Ile Ile Glu Asn Ala Glu Leu Leu Asp Gln Ile Ala
            340                 345                 350
Lys Ile Leu Thr Ile Tyr Gln Ser Ser Glu Asp Ile Gln Glu Glu Leu
        355                 360                 365
Thr Asn Leu Asn Ser Glu Leu Thr Gln Glu Glu Ile Glu Gln Ile Ser
    370                 375                 380
Asn Leu Lys Gly Tyr Thr Gly Thr His Asn Leu Ser Leu Lys Ala Ile
385                 390                 395                 400
Asn Leu Ile Leu Asp Glu Leu Trp His Thr Asn Asp Asn Gln Ile Ala
                405                 410                 415
Ile Phe Asn Arg Leu Lys Leu Val Pro Lys Lys Val Asp Leu Ser Gln
            420                 425                 430
Gln Lys Glu Ile Pro Thr Thr Leu Val Asp Asp Phe Ile Leu Ser Pro
        435                 440                 445
Val Val Lys Arg Ser Phe Ile Gln Ser Ile Lys Val Ile Asn Ala Ile
    450                 455                 460
Ile Lys Lys Tyr Gly Leu Pro Asn Asp Ile Ile Ile Glu Leu Ala Arg
465                 470                 475                 480
Glu Lys Asn Ser Lys Asp Ala Gln Lys Met Ile Asn Glu Met Gln Lys
                485                 490                 495
Arg Asn Arg Gln Thr Asn Glu Arg Ile Glu Glu Ile Ile Arg Thr Thr
            500                 505                 510
Gly Lys Glu Asn Ala Lys Tyr Leu Ile Glu Lys Ile Lys Leu His Asp
        515                 520                 525
Met Gln Glu Gly Lys Cys Leu Tyr Ser Leu Glu Ala Ile Pro Leu Glu
    530                 535                 540
Asp Leu Leu Asn Asn Pro Phe Asn Tyr Glu Val Asp His Ile Ile Pro
545                 550                 555                 560
Arg Ser Val Ser Phe Asp Asn Ser Phe Asn Asn Lys Val Leu Val Lys
                565                 570                 575
Gln Glu Glu Asn Ser Lys Lys Gly Asn Arg Thr Pro Phe Gln Tyr Leu
            580                 585                 590
Ser Ser Ser Asp Ser Lys Ile Ser Tyr Glu Thr Phe Lys Lys His Ile
        595                 600                 605
Leu Asn Leu Ala Lys Gly Lys Gly Arg Ile Ser Lys Thr Lys Lys Glu
    610                 615                 620
Tyr Leu Leu Glu Glu Arg Asp Ile Asn Arg Phe Ser Val Gln Lys Asp
625                 630                 635                 640
Phe Ile Asn Arg Asn Leu Val Asp Thr Arg Tyr Ala Thr Arg Gly Leu
                645                 650                 655
Met Asn Leu Leu Arg Ser Tyr Phe Arg Val Asn Asn Leu Asp Val Lys
            660                 665                 670
Val Lys Ser Ile Asn Gly Gly Phe Thr Ser Phe Leu Arg Arg Lys Trp
        675                 680                 685
Lys Phe Lys Lys Glu Arg Asn Lys Gly Tyr Lys His His Ala Glu Asp
    690                 695                 700
Ala Leu Ile Ile Ala Asn Ala Asp Phe Ile Phe Lys Glu Trp Lys Lys
705                 710                 715                 720
Leu Asp Lys Ala Lys Lys Val Met Glu Asn Gln Met Phe Glu Glu Lys
                725                 730                 735
Gln Ala Glu Ser Met Pro Glu Ile Glu Thr Glu Gln Glu Tyr Lys Glu
            740                 745                 750
```

```
Ile Phe Ile Thr Pro His Gln Ile Lys His Ile Lys Asp Phe Lys Asp
            755                 760                 765

Tyr Lys Tyr Ser His Arg Val Asp Lys Lys Pro Asn Arg Glu Leu Ile
770                 775                 780

Asn Asp Thr Leu Tyr Ser Thr Arg Lys Asp Lys Gly Asn Thr Leu
785                 790                 795                 800

Ile Val Asn Asn Leu Asn Gly Leu Tyr Asp Lys Asp Asn Asp Lys Leu
            805                 810                 815

Lys Lys Leu Ile Asn Lys Ser Pro Glu Lys Leu Met Tyr His His
                820                 825                 830

Asp Pro Gln Thr Tyr Gln Lys Leu Lys Leu Ile Met Glu Gln Tyr Gly
            835                 840                 845

Asp Glu Lys Asn Pro Leu Tyr Lys Tyr Glu Glu Thr Gly Asn Tyr
850                 855                 860

Leu Thr Lys Tyr Ser Lys Lys Asp Asn Gly Pro Val Ile Lys Lys Ile
865                 870                 875                 880

Lys Tyr Tyr Gly Asn Lys Leu Asn Ala His Leu Asp Ile Thr Asp Asp
                885                 890                 895

Tyr Pro Asn Ser Arg Asn Lys Val Val Lys Leu Ser Leu Lys Pro Tyr
            900                 905                 910

Arg Phe Asp Val Tyr Leu Asp Asn Gly Val Tyr Lys Phe Val Thr Val
            915                 920                 925

Lys Asn Leu Asp Val Ile Lys Lys Glu Asn Tyr Tyr Glu Val Asn Ser
            930                 935                 940

Lys Cys Tyr Glu Glu Ala Lys Lys Leu Lys Lys Ile Ser Asn Gln Ala
945                 950                 955                 960

Glu Phe Ile Ala Ser Phe Tyr Asn Asn Asp Leu Ile Lys Ile Asn Gly
                965                 970                 975

Glu Leu Tyr Arg Val Ile Gly Val Asn Asp Leu Leu Asn Arg Ile
            980                 985                 990

Glu Val Asn Met Ile Asp Ile Thr Tyr Arg Glu Tyr Leu Glu Asn Met
            995                 1000                1005

Asn Asp Lys Arg Pro Pro Arg Ile Ile Lys Thr Ile Ala Ser Lys
    1010                1015                1020

Thr Gln Ser Ile Lys Lys Tyr Ser Thr Asp Ile Leu Gly Asn Leu
    1025                1030                1035

Tyr Glu Val Lys Ser Lys Lys His Pro Gln Ile Ile Lys Lys Gly
    1040                1045                1050

<210> SEQ ID NO 64
<211> LENGTH: 984
<212> TYPE: PRT
<213> ORGANISM: Campylobacter jejuni

<400> SEQUENCE: 64

Met Ala Arg Ile Leu Ala Phe Asp Ile Gly Ile Ser Ser Ile Gly Trp
1               5                   10                  15

Ala Phe Ser Glu Asn Asp Glu Leu Lys Asp Cys Gly Val Arg Ile Phe
                20                  25                  30

Thr Lys Val Glu Asn Pro Lys Thr Gly Glu Ser Leu Ala Leu Pro Arg
            35                  40                  45

Arg Leu Ala Arg Ser Ala Arg Lys Arg Leu Ala Arg Arg Lys Ala Arg
        50                  55                  60

Leu Asn His Leu Lys His Leu Ile Ala Asn Glu Phe Lys Leu Asn Tyr
65                  70                  75                  80
```

-continued

```
Glu Asp Tyr Gln Ser Phe Asp Glu Ser Leu Ala Lys Ala Tyr Lys Gly
                85                  90                  95
Ser Leu Ile Ser Pro Tyr Glu Leu Arg Phe Arg Ala Leu Asn Glu Leu
            100                 105                 110
Leu Ser Lys Gln Asp Phe Ala Arg Val Ile Leu His Ile Ala Lys Arg
        115                 120                 125
Arg Gly Tyr Asp Asp Ile Lys Asn Ser Asp Asp Lys Glu Lys Gly Ala
    130                 135                 140
Ile Leu Lys Ala Ile Lys Gln Asn Glu Glu Lys Leu Ala Asn Tyr Gln
145                 150                 155                 160
Ser Val Gly Glu Tyr Leu Tyr Lys Glu Tyr Phe Gln Lys Phe Lys Glu
                165                 170                 175
Asn Ser Lys Glu Phe Thr Asn Val Arg Asn Lys Lys Glu Ser Tyr Glu
            180                 185                 190
Arg Cys Ile Ala Gln Ser Phe Leu Lys Asp Glu Leu Lys Leu Ile Phe
        195                 200                 205
Lys Lys Gln Arg Glu Phe Gly Phe Ser Phe Ser Lys Lys Phe Glu Glu
    210                 215                 220
Glu Val Leu Ser Val Ala Phe Tyr Lys Arg Ala Leu Lys Asp Phe Ser
225                 230                 235                 240
His Leu Val Gly Asn Cys Ser Phe Phe Thr Asp Glu Lys Arg Ala Pro
                245                 250                 255
Lys Asn Ser Pro Leu Ala Phe Met Phe Val Ala Leu Thr Arg Ile Ile
            260                 265                 270
Asn Leu Leu Asn Asn Leu Lys Asn Thr Glu Gly Ile Leu Tyr Thr Lys
        275                 280                 285
Asp Asp Leu Asn Ala Leu Leu Asn Glu Val Leu Lys Asn Gly Thr Leu
    290                 295                 300
Thr Tyr Lys Gln Thr Lys Lys Leu Leu Gly Leu Ser Asp Asp Tyr Glu
305                 310                 315                 320
Phe Lys Gly Glu Lys Gly Thr Tyr Phe Ile Glu Phe Lys Lys Tyr Lys
                325                 330                 335
Glu Phe Ile Lys Ala Leu Gly Glu His Asn Leu Ser Gln Asp Asp Leu
            340                 345                 350
Asn Glu Ile Ala Lys Asp Ile Thr Leu Ile Lys Asp Glu Ile Lys Leu
        355                 360                 365
Lys Lys Ala Leu Ala Lys Tyr Asp Leu Asn Gln Asn Gln Ile Asp Ser
    370                 375                 380
Leu Ser Lys Leu Glu Phe Lys Asp His Leu Asn Ile Ser Phe Lys Ala
385                 390                 395                 400
Leu Lys Leu Val Thr Pro Leu Met Leu Glu Gly Lys Lys Tyr Asp Glu
                405                 410                 415
Ala Cys Asn Glu Leu Asn Leu Lys Val Ala Ile Asn Glu Asp Lys Lys
            420                 425                 430
Asp Phe Leu Pro Ala Phe Asn Glu Thr Tyr Tyr Lys Asp Glu Val Thr
        435                 440                 445
Asn Pro Val Val Leu Arg Ala Ile Lys Glu Tyr Arg Lys Val Leu Asn
    450                 455                 460
Ala Leu Leu Lys Lys Tyr Gly Lys Val His Lys Ile Asn Ile Glu Leu
465                 470                 475                 480
Ala Arg Glu Val Gly Lys Asn His Ser Gln Arg Ala Lys Ile Glu Lys
                485                 490                 495
```

```
Glu Gln Asn Glu Asn Tyr Lys Ala Lys Lys Asp Ala Glu Leu Glu Cys
                500                 505                 510

Glu Lys Leu Gly Leu Lys Ile Asn Ser Lys Asn Ile Leu Lys Leu Arg
            515                 520                 525

Leu Phe Lys Glu Gln Lys Glu Phe Cys Ala Tyr Ser Gly Glu Lys Ile
        530                 535                 540

Lys Ile Ser Asp Leu Gln Asp Glu Lys Met Leu Glu Ile Asp His Ile
545                 550                 555                 560

Tyr Pro Tyr Ser Arg Ser Phe Asp Asp Ser Tyr Met Asn Lys Val Leu
                565                 570                 575

Val Phe Thr Lys Gln Asn Gln Glu Lys Leu Asn Gln Thr Pro Phe Glu
            580                 585                 590

Ala Phe Gly Asn Asp Ser Ala Lys Trp Gln Lys Ile Glu Val Leu Ala
        595                 600                 605

Lys Asn Leu Pro Thr Lys Lys Gln Lys Arg Ile Leu Asp Lys Asn Tyr
            610                 615                 620

Lys Asp Lys Glu Gln Lys Asn Phe Lys Asp Arg Asn Leu Asn Asp Thr
625                 630                 635                 640

Arg Tyr Ile Ala Arg Leu Val Leu Asn Tyr Thr Lys Asp Tyr Leu Asp
                645                 650                 655

Phe Leu Pro Leu Ser Asp Asp Glu Asn Thr Lys Leu Asn Asp Thr Gln
            660                 665                 670

Lys Gly Ser Lys Val His Val Glu Ala Lys Ser Gly Met Leu Thr Ser
        675                 680                 685

Ala Leu Arg His Thr Trp Gly Phe Ser Ala Lys Asp Arg Asn Asn His
        690                 695                 700

Leu His His Ala Ile Asp Ala Val Ile Ile Ala Tyr Ala Asn Asn Ser
705                 710                 715                 720

Ile Val Lys Ala Phe Ser Asp Phe Lys Lys Glu Gln Glu Ser Asn Ser
                725                 730                 735

Ala Glu Leu Tyr Ala Lys Lys Ile Ser Glu Leu Asp Tyr Lys Asn Lys
            740                 745                 750

Arg Lys Phe Phe Glu Pro Phe Ser Gly Phe Arg Gln Lys Val Leu Asp
        755                 760                 765

Lys Ile Asp Glu Ile Phe Val Ser Lys Pro Glu Arg Lys Lys Pro Ser
770                 775                 780

Gly Ala Leu His Glu Glu Thr Phe Arg Lys Glu Glu Phe Tyr Gln
785                 790                 795                 800

Ser Tyr Gly Gly Lys Glu Gly Val Leu Lys Ala Leu Glu Leu Gly Lys
                805                 810                 815

Ile Arg Lys Val Asn Gly Lys Ile Val Lys Asn Gly Asp Met Phe Arg
            820                 825                 830

Val Asp Ile Phe Lys His Lys Lys Thr Asn Lys Phe Tyr Ala Val Pro
        835                 840                 845

Ile Tyr Thr Met Asp Phe Ala Leu Lys Val Leu Pro Asn Lys Ala Val
        850                 855                 860

Ala Arg Ser Lys Lys Gly Glu Ile Lys Asp Trp Ile Leu Met Asp Glu
865                 870                 875                 880

Asn Tyr Glu Phe Cys Phe Ser Leu Tyr Lys Asp Ser Leu Ile Leu Ile
                885                 890                 895

Gln Thr Lys Asp Met Gln Glu Pro Glu Phe Val Tyr Tyr Asn Ala Phe
            900                 905                 910
```

```
Thr Ser Ser Thr Val Ser Leu Ile Val Ser Lys His Asp Asn Lys Phe
            915                 920                 925

Glu Thr Leu Ser Lys Asn Gln Lys Ile Leu Phe Lys Asn Ala Asn Glu
    930                 935                 940

Lys Glu Val Ile Ala Lys Ser Ile Gly Ile Gln Asn Leu Lys Val Phe
945                 950                 955                 960

Glu Lys Tyr Ile Val Ser Ala Leu Gly Glu Val Thr Lys Ala Glu Phe
                965                 970                 975

Arg Gln Arg Glu Asp Phe Lys Lys
            980

<210> SEQ ID NO 65
<211> LENGTH: 1037
<212> TYPE: PRT
<213> ORGANISM: Parvibaculum lavamentivorans

<400> SEQUENCE: 65

Met Glu Arg Ile Phe Gly Phe Asp Ile Gly Thr Thr Ser Ile Gly Phe
1               5                   10                  15

Ser Val Ile Asp Tyr Ser Ser Thr Gln Ser Ala Gly Asn Ile Gln Arg
                20                  25                  30

Leu Gly Val Arg Ile Phe Pro Glu Ala Arg Asp Pro Asp Gly Thr Pro
            35                  40                  45

Leu Asn Gln Gln Arg Arg Gln Lys Arg Met Met Arg Arg Gln Leu Arg
        50                  55                  60

Arg Arg Arg Ile Arg Arg Lys Ala Leu Asn Glu Thr Leu His Glu Ala
65                  70                  75                  80

Gly Phe Leu Pro Ala Tyr Gly Ser Ala Asp Trp Pro Val Val Met Ala
                85                  90                  95

Asp Glu Pro Tyr Glu Leu Arg Arg Arg Gly Leu Glu Glu Gly Leu Ser
                100                 105                 110

Ala Tyr Glu Phe Gly Arg Ala Ile Tyr His Leu Ala Gln His Arg His
            115                 120                 125

Phe Lys Gly Arg Glu Leu Glu Glu Ser Asp Thr Pro Asp Pro Asp Val
        130                 135                 140

Asp Asp Glu Lys Glu Ala Ala Asn Glu Arg Ala Ala Thr Leu Lys Ala
145                 150                 155                 160

Leu Lys Asn Glu Gln Thr Thr Leu Gly Ala Trp Leu Ala Arg Arg Pro
                165                 170                 175

Pro Ser Asp Arg Lys Arg Gly Ile His Ala His Arg Asn Val Val Ala
            180                 185                 190

Glu Glu Phe Glu Arg Leu Trp Glu Val Gln Ser Lys Phe His Pro Ala
        195                 200                 205

Leu Lys Ser Glu Glu Met Arg Ala Arg Ile Ser Asp Thr Ile Phe Ala
    210                 215                 220

Gln Arg Pro Val Phe Trp Arg Lys Asn Thr Leu Gly Glu Cys Arg Phe
225                 230                 235                 240

Met Pro Gly Glu Pro Leu Cys Pro Lys Gly Ser Trp Leu Ser Gln Gln
                245                 250                 255

Arg Arg Met Leu Glu Lys Leu Asn Asn Leu Ala Ile Ala Gly Gly Asn
            260                 265                 270

Ala Arg Pro Leu Asp Ala Glu Glu Arg Asp Ala Ile Leu Ser Lys Leu
        275                 280                 285

Gln Gln Gln Ala Ser Met Ser Trp Pro Gly Val Arg Ser Ala Leu Lys
    290                 295                 300
```

```
Ala Leu Tyr Lys Gln Arg Gly Glu Pro Gly Ala Glu Lys Ser Leu Lys
305                 310                 315                 320

Phe Asn Leu Glu Leu Gly Gly Ser Lys Leu Leu Gly Asn Ala Leu
            325                 330                 335

Glu Ala Lys Leu Ala Asp Met Phe Gly Pro Asp Trp Pro Ala His Pro
            340                 345                 350

Arg Lys Gln Glu Ile Arg His Ala Val His Glu Arg Leu Trp Ala Ala
            355                 360                 365

Asp Tyr Gly Glu Thr Pro Asp Lys Lys Arg Val Ile Ile Leu Ser Glu
            370                 375                 380

Lys Asp Arg Lys Ala His Arg Glu Ala Ala Asn Ser Phe Val Ala
385                 390                 395                 400

Asp Phe Gly Ile Thr Gly Glu Gln Ala Ala Gln Leu Gln Ala Leu Lys
            405                 410                 415

Leu Pro Thr Gly Trp Glu Pro Tyr Ser Ile Pro Ala Leu Asn Leu Phe
            420                 425                 430

Leu Ala Glu Leu Glu Lys Gly Gly Arg Phe Gly Ala Leu Val Asn Gly
            435                 440                 445

Pro Asp Trp Glu Gly Trp Arg Arg Thr Asn Phe Pro His Arg Asn Gln
450                 455                 460

Pro Thr Gly Glu Ile Leu Asp Lys Leu Pro Ser Pro Ala Ser Lys Glu
465                 470                 475                 480

Glu Arg Glu Arg Ile Ser Gln Leu Arg Asn Pro Thr Val Val Arg Thr
            485                 490                 495

Gln Asn Glu Leu Arg Lys Val Val Asn Asn Leu Ile Gly Leu Tyr Gly
            500                 505                 510

Lys Pro Asp Arg Ile Arg Ile Glu Val Gly Arg Asp Val Gly Lys Ser
            515                 520                 525

Lys Arg Glu Arg Glu Glu Ile Gln Ser Gly Ile Arg Arg Asn Glu Lys
            530                 535                 540

Gln Arg Lys Lys Ala Thr Glu Asp Leu Ile Lys Asn Gly Ile Ala Asn
545                 550                 555                 560

Pro Ser Arg Asp Asp Val Glu Lys Trp Ile Leu Trp Lys Glu Gly Gln
            565                 570                 575

Glu Arg Cys Pro Tyr Thr Gly Asp Gln Ile Gly Phe Asn Ala Leu Phe
            580                 585                 590

Arg Glu Gly Arg Tyr Glu Val Glu His Ile Trp Pro Arg Ser Arg Ser
            595                 600                 605

Phe Asp Asn Ser Pro Arg Asn Lys Thr Leu Cys Arg Lys Asp Val Asn
610                 615                 620

Ile Glu Lys Gly Asn Arg Met Pro Phe Glu Ala Phe Gly His Asp Glu
625                 630                 635                 640

Asp Arg Trp Ser Ala Ile Gln Ile Arg Leu Gln Gly Met Val Ser Ala
            645                 650                 655

Lys Gly Gly Thr Gly Met Ser Pro Gly Lys Val Lys Arg Phe Leu Ala
            660                 665                 670

Lys Thr Met Pro Glu Asp Phe Ala Ala Arg Gln Leu Asn Asp Thr Arg
            675                 680                 685

Tyr Ala Ala Lys Gln Ile Leu Ala Gln Leu Lys Arg Leu Trp Pro Asp
            690                 695                 700

Met Gly Pro Glu Ala Pro Val Lys Val Glu Ala Val Thr Gly Gln Val
705                 710                 715                 720
```

```
Thr Ala Gln Leu Arg Lys Leu Trp Thr Leu Asn Asn Ile Leu Ala Asp
                725                 730                 735

Asp Gly Glu Lys Thr Arg Ala Asp His Arg His Ala Ile Asp Ala
            740                 745                 750

Leu Thr Val Ala Cys Thr His Pro Gly Met Thr Asn Lys Leu Ser Arg
            755                 760                 765

Tyr Trp Gln Leu Arg Asp Asp Pro Arg Ala Glu Lys Pro Ala Leu Thr
            770                 775                 780

Pro Pro Trp Asp Thr Ile Arg Ala Asp Ala Glu Lys Ala Val Ser Glu
785                 790                 795                 800

Ile Val Val Ser His Arg Val Arg Lys Lys Val Ser Gly Pro Leu His
                805                 810                 815

Lys Glu Thr Thr Tyr Gly Asp Thr Gly Thr Asp Ile Lys Thr Lys Ser
                820                 825                 830

Gly Thr Tyr Arg Gln Phe Val Thr Arg Lys Lys Ile Glu Ser Leu Ser
            835                 840                 845

Lys Gly Glu Leu Asp Glu Ile Arg Asp Pro Arg Ile Lys Glu Ile Val
            850                 855                 860

Ala Ala His Val Ala Gly Arg Gly Gly Asp Pro Lys Lys Ala Phe Pro
865                 870                 875                 880

Pro Tyr Pro Cys Val Ser Pro Gly Pro Glu Ile Arg Lys Val Arg
                885                 890                 895

Leu Thr Ser Lys Gln Gln Leu Asn Leu Met Ala Gln Thr Gly Asn Gly
                900                 905                 910

Tyr Ala Asp Leu Gly Ser Asn His His Ile Ala Ile Tyr Arg Leu Pro
            915                 920                 925

Asp Gly Lys Ala Asp Phe Glu Ile Val Ser Leu Phe Asp Ala Ser Arg
            930                 935                 940

Arg Leu Ala Gln Arg Asn Pro Ile Val Gln Arg Thr Arg Ala Asp Gly
945                 950                 955                 960

Ala Ser Phe Val Met Ser Leu Ala Ala Gly Ala Ile Met Ile Pro
                965                 970                 975

Glu Gly Ser Lys Lys Gly Ile Trp Ile Val Gln Gly Val Trp Ala Ser
            980                 985                 990

Gly Gln Val Val Leu Glu Arg Asp Thr Asp Ala Asp His Ser Thr Thr
            995                 1000                1005

Thr Arg Pro Met Pro Asn Pro Ile Leu Lys Asp Asp Ala Lys Lys
        1010            1015            1020

Val Ser Ile Asp Pro Ile Gly Arg Val Arg Pro Ser Asn Asp
        1025            1030            1035

<210> SEQ ID NO 66
<211> LENGTH: 1082
<212> TYPE: PRT
<213> ORGANISM: Neisseria cinerea

<400> SEQUENCE: 66

Met Ala Ala Phe Lys Pro Asn Pro Met Asn Tyr Ile Leu Gly Leu Asp
1               5                   10                  15

Ile Gly Ile Ala Ser Val Gly Trp Ala Ile Val Glu Ile Asp Glu Glu
            20                  25                  30

Glu Asn Pro Ile Arg Leu Ile Asp Leu Gly Val Arg Val Phe Glu Arg
        35                  40                  45

Ala Glu Val Pro Lys Thr Gly Asp Ser Leu Ala Ala Ala Arg Arg Leu
    50                  55                  60
```

```
Ala Arg Ser Val Arg Arg Leu Thr Arg Arg Ala His Arg Leu Leu
 65                  70                  75                  80

Arg Ala Arg Arg Leu Leu Lys Arg Glu Gly Val Leu Gln Ala Ala Asp
                 85                  90                  95

Phe Asp Glu Asn Gly Leu Ile Lys Ser Leu Pro Asn Thr Pro Trp Gln
            100                 105                 110

Leu Arg Ala Ala Ala Leu Asp Arg Lys Leu Thr Pro Leu Glu Trp Ser
        115                 120                 125

Ala Val Leu Leu His Leu Ile Lys His Arg Gly Tyr Leu Ser Gln Arg
130                 135                 140

Lys Asn Glu Gly Glu Thr Ala Asp Lys Glu Leu Gly Ala Leu Leu Lys
145                 150                 155                 160

Gly Val Ala Asp Asn Thr His Ala Leu Gln Thr Gly Asp Phe Arg Thr
                165                 170                 175

Pro Ala Glu Leu Ala Leu Asn Lys Phe Glu Lys Glu Ser Gly His Ile
            180                 185                 190

Arg Asn Gln Arg Gly Asp Tyr Ser His Thr Phe Asn Arg Lys Asp Leu
        195                 200                 205

Gln Ala Glu Leu Asn Leu Leu Phe Glu Lys Gln Lys Glu Phe Gly Asn
210                 215                 220

Pro His Val Ser Asp Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                245                 250                 255

His Cys Thr Phe Glu Pro Thr Glu Pro Lys Ala Ala Lys Asn Thr Tyr
            260                 265                 270

Thr Ala Glu Arg Phe Val Trp Leu Thr Lys Leu Asn Asn Leu Arg Ile
        275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Asp Leu Asp Thr Ala Phe Phe Lys Gly Leu Arg
                325                 330                 335

Tyr Gly Lys Asp Asn Ala Glu Ala Ser Thr Leu Met Glu Met Lys Ala
            340                 345                 350

Tyr His Ala Ile Ser Arg Ala Leu Glu Lys Gly Leu Lys Asp Lys
        355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Val Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
            420                 425                 430

Pro Leu Met Glu Gln Gly Asn Arg Tyr Asp Glu Ala Cys Thr Glu Ile
        435                 440                 445

Tyr Gly Asp His Tyr Gly Lys Lys Asn Thr Glu Glu Lys Ile Tyr Leu
450                 455                 460

Pro Pro Ile Pro Ala Asp Glu Ile Arg Asn Pro Val Val Leu Arg Ala
465                 470                 475                 480
```

```
Leu Ser Gln Ala Arg Lys Val Ile Asn Gly Val Arg Arg Tyr Gly
                485                 490                 495

Ser Pro Ala Arg Ile His Ile Glu Thr Ala Arg Glu Val Gly Lys Ser
            500                 505                 510

Phe Lys Asp Arg Lys Glu Ile Glu Lys Arg Gln Glu Glu Asn Arg Lys
        515                 520                 525

Asp Arg Glu Lys Ser Ala Ala Lys Phe Arg Glu Tyr Phe Pro Asn Phe
    530                 535                 540

Val Gly Glu Pro Lys Ser Lys Asp Ile Leu Lys Leu Arg Leu Tyr Glu
545                 550                 555                 560

Gln Gln His Gly Lys Cys Leu Tyr Ser Gly Lys Glu Ile Asn Leu Gly
                565                 570                 575

Arg Leu Asn Glu Lys Gly Tyr Val Glu Ile Asp His Ala Leu Pro Phe
            580                 585                 590

Ser Arg Thr Trp Asp Asp Ser Phe Asn Asn Lys Val Leu Ala Leu Gly
        595                 600                 605

Ser Glu Asn Gln Asn Lys Gly Asn Gln Thr Pro Tyr Glu Tyr Phe Asn
    610                 615                 620

Gly Lys Asp Asn Ser Arg Glu Trp Gln Glu Phe Lys Ala Arg Val Glu
625                 630                 635                 640

Thr Ser Arg Phe Pro Arg Ser Lys Lys Gln Arg Ile Leu Leu Gln Lys
                645                 650                 655

Phe Asp Glu Asp Gly Phe Lys Glu Arg Asn Leu Asn Asp Thr Arg Tyr
            660                 665                 670

Ile Asn Arg Phe Leu Cys Gln Phe Val Ala Asp His Met Leu Leu Thr
        675                 680                 685

Gly Lys Gly Lys Arg Arg Val Phe Ala Ser Asn Gly Gln Ile Thr Asn
    690                 695                 700

Leu Leu Arg Gly Phe Trp Gly Leu Arg Lys Val Arg Ala Glu Asn Asp
705                 710                 715                 720

Arg His His Ala Leu Asp Ala Val Val Val Ala Cys Ser Thr Ile Ala
                725                 730                 735

Met Gln Gln Lys Ile Thr Arg Phe Val Arg Tyr Lys Glu Met Asn Ala
            740                 745                 750

Phe Asp Gly Lys Thr Ile Asp Lys Glu Thr Gly Glu Val Leu His Gln
        755                 760                 765

Lys Ala His Phe Pro Gln Pro Trp Glu Phe Phe Ala Gln Glu Val Met
    770                 775                 780

Ile Arg Val Phe Gly Lys Pro Asp Gly Lys Pro Glu Phe Glu Glu Ala
785                 790                 795                 800

Asp Thr Pro Glu Lys Leu Arg Thr Leu Leu Ala Glu Lys Leu Ser Ser
                805                 810                 815

Arg Pro Glu Ala Val His Lys Tyr Val Thr Pro Leu Phe Ile Ser Arg
            820                 825                 830

Ala Pro Asn Arg Lys Met Ser Gly Gln Gly His Met Glu Thr Val Lys
        835                 840                 845

Ser Ala Lys Arg Leu Asp Glu Gly Ile Ser Val Leu Arg Val Pro Leu
    850                 855                 860

Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895
```

-continued

Asp Asp Pro Ala Lys Ala Phe Ala Glu Pro Phe Tyr Lys Tyr Asp Lys
                900                 905                 910

Ala Gly Asn Arg Thr Gln Gln Val Lys Ala Val Arg Val Glu Gln Val
            915                 920                 925

Gln Lys Thr Gly Val Trp Val His Asn His Asn Gly Ile Ala Asp Asn
        930                 935                 940

Ala Thr Ile Val Arg Val Asp Val Phe Glu Lys Gly Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Thr Val Met Asp
            980                 985                 990

Asp Ser Phe Glu Phe Lys Phe Val Leu Tyr Ala Asn Asp Leu Ile Lys
        995                 1000                1005

Leu Thr Ala Lys Lys Asn Glu Phe Leu Gly Tyr Phe Val Ser Leu
    1010                1015                1020

Asn Arg Ala Thr Gly Ala Ile Asp Ile Arg Thr His Asp Thr Asp
    1025                1030                1035

Ser Thr Lys Gly Lys Asn Gly Ile Phe Gln Ser Val Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 67
<211> LENGTH: 1003
<212> TYPE: PRT
<213> ORGANISM: Campylobacter lari

<400> SEQUENCE: 67

Met Arg Ile Leu Gly Phe Asp Ile Gly Ile Asn Ser Ile Gly Trp Ala
1               5                   10                  15

Phe Val Glu Asn Asp Glu Leu Lys Asp Cys Gly Val Arg Ile Phe Thr
                20                  25                  30

Lys Ala Glu Asn Pro Lys Asn Lys Glu Ser Leu Ala Leu Pro Arg Arg
            35                  40                  45

Asn Ala Arg Ser Ser Arg Arg Leu Lys Arg Arg Lys Ala Arg Leu
        50                  55                  60

Ile Ala Ile Lys Arg Ile Leu Ala Lys Glu Leu Lys Leu Asn Tyr Lys
65                  70                  75                  80

Asp Tyr Val Ala Ala Asp Gly Glu Leu Pro Lys Ala Tyr Glu Gly Ser
                85                  90                  95

Leu Ala Ser Val Tyr Glu Leu Arg Tyr Lys Ala Leu Thr Gln Asn Leu
            100                 105                 110

Glu Thr Lys Asp Leu Ala Arg Val Ile Leu His Ile Ala Lys His Arg
        115                 120                 125

Gly Tyr Met Asn Lys Asn Glu Lys Ser Asn Asp Ala Lys Lys Gly
    130                 135                 140

Lys Ile Leu Ser Ala Leu Lys Asn Asn Ala Leu Lys Leu Glu Asn Tyr
145                 150                 155                 160

Gln Ser Val Gly Glu Tyr Phe Tyr Lys Glu Phe Phe Gln Lys Tyr Lys
                165                 170                 175

Lys Asn Thr Lys Asn Phe Ile Lys Ile Arg Asn Thr Lys Asp Asn Tyr
            180                 185                 190

-continued

```
Asn Asn Cys Val Leu Ser Ser Asp Leu Glu Lys Glu Leu Lys Leu Ile
            195                 200                 205

Leu Glu Lys Gln Lys Glu Phe Gly Tyr Asn Tyr Ser Glu Asp Phe Ile
    210                 215                 220

Asn Glu Ile Leu Lys Val Ala Phe Phe Gln Arg Pro Leu Lys Asp Phe
225                 230                 235                 240

Ser His Leu Val Gly Ala Cys Thr Phe Phe Glu Glu Lys Arg Ala
                245                 250                 255

Cys Lys Asn Ser Tyr Ser Ala Trp Glu Phe Val Ala Leu Thr Lys Ile
            260                 265                 270

Ile Asn Glu Ile Lys Ser Leu Glu Lys Ile Ser Gly Glu Ile Val Pro
    275                 280                 285

Thr Gln Thr Ile Asn Glu Val Leu Asn Leu Ile Leu Asp Lys Gly Ser
290                 295                 300

Ile Thr Tyr Lys Lys Phe Arg Ser Cys Ile Asn Leu His Glu Ser Ile
305                 310                 315                 320

Ser Phe Lys Ser Leu Lys Tyr Asp Lys Glu Asn Ala Glu Asn Ala Lys
                325                 330                 335

Leu Ile Asp Phe Arg Lys Leu Val Glu Phe Lys Lys Ala Leu Gly Val
            340                 345                 350

His Ser Leu Ser Arg Gln Glu Leu Asp Gln Ile Ser Thr His Ile Thr
    355                 360                 365

Leu Ile Lys Asp Asn Val Lys Leu Lys Thr Val Leu Glu Lys Tyr Asn
    370                 375                 380

Leu Ser Asn Glu Gln Ile Asn Asn Leu Leu Glu Ile Glu Phe Asn Asp
385                 390                 395                 400

Tyr Ile Asn Leu Ser Phe Lys Ala Leu Gly Met Ile Leu Pro Leu Met
                405                 410                 415

Arg Glu Gly Lys Arg Tyr Asp Glu Ala Cys Glu Ile Ala Asn Leu Lys
            420                 425                 430

Pro Lys Thr Val Asp Glu Lys Asp Phe Leu Pro Ala Phe Cys Asp
    435                 440                 445

Ser Ile Phe Ala His Glu Leu Ser Asn Pro Val Asn Arg Ala Ile
    450                 455                 460

Ser Glu Tyr Arg Lys Val Leu Asn Ala Leu Leu Lys Lys Tyr Gly Lys
465                 470                 475                 480

Val His Lys Ile His Leu Glu Leu Ala Arg Asp Val Gly Leu Ser Lys
                485                 490                 495

Lys Ala Arg Glu Lys Ile Glu Lys Gln Lys Glu Asn Gln Ala Val
            500                 505                 510

Asn Ala Trp Ala Leu Lys Glu Cys Glu Asn Ile Gly Leu Lys Ala Ser
    515                 520                 525

Ala Lys Asn Ile Leu Lys Leu Lys Leu Trp Lys Glu Gln Lys Glu Ile
    530                 535                 540

Cys Ile Tyr Ser Gly Asn Lys Ile Ser Ile Glu His Leu Lys Asp Glu
545                 550                 555                 560

Lys Ala Leu Glu Val Asp His Ile Tyr Pro Tyr Ser Arg Ser Phe Asp
                565                 570                 575

Asp Ser Phe Ile Asn Lys Val Leu Val Phe Thr Lys Glu Asn Gln Glu
            580                 585                 590

Lys Leu Asn Lys Thr Pro Phe Glu Ala Phe Gly Lys Asn Ile Glu Lys
    595                 600                 605
```

```
Trp Ser Lys Ile Gln Thr Leu Ala Gln Asn Leu Pro Tyr Lys Lys Lys
    610                 615                 620
Asn Lys Ile Leu Asp Glu Asn Phe Lys Asp Lys Gln Gln Glu Asp Phe
625                 630                 635                 640
Ile Ser Arg Asn Leu Asn Asp Thr Arg Tyr Ile Ala Thr Leu Ile Ala
                645                 650                 655
Lys Tyr Thr Lys Glu Tyr Leu Asn Phe Leu Leu Leu Ser Glu Asn Glu
            660                 665                 670
Asn Ala Asn Leu Lys Ser Gly Glu Lys Gly Ser Lys Ile His Val Gln
            675                 680                 685
Thr Ile Ser Gly Met Leu Thr Ser Val Leu Arg His Thr Trp Gly Phe
        690                 695                 700
Asp Lys Lys Asp Arg Asn Asn His Leu His His Ala Leu Asp Ala Ile
705                 710                 715                 720
Ile Val Ala Tyr Ser Thr Asn Ser Ile Ile Lys Ala Phe Ser Asp Phe
                725                 730                 735
Arg Lys Asn Gln Glu Leu Leu Lys Ala Arg Phe Tyr Ala Lys Glu Leu
            740                 745                 750
Thr Ser Asp Asn Tyr Lys His Gln Val Lys Phe Phe Glu Pro Phe Lys
        755                 760                 765
Ser Phe Arg Glu Lys Ile Leu Ser Lys Ile Asp Glu Ile Phe Val Ser
    770                 775                 780
Lys Pro Pro Arg Lys Arg Ala Arg Arg Ala Leu His Lys Asp Thr Phe
785                 790                 795                 800
His Ser Glu Asn Lys Ile Ile Asp Lys Cys Ser Tyr Asn Ser Lys Glu
                805                 810                 815
Gly Leu Gln Ile Ala Leu Ser Cys Gly Arg Val Arg Lys Ile Gly Thr
            820                 825                 830
Lys Tyr Val Glu Asn Asp Thr Ile Val Arg Val Asp Ile Phe Lys Lys
        835                 840                 845
Gln Asn Lys Phe Tyr Ala Ile Pro Ile Tyr Ala Met Asp Phe Ala Leu
    850                 855                 860
Gly Ile Leu Pro Asn Lys Ile Val Ile Thr Gly Lys Asp Lys Asn Asn
865                 870                 875                 880
Asn Pro Lys Gln Trp Gln Thr Ile Asp Glu Ser Tyr Glu Phe Cys Phe
                885                 890                 895
Ser Leu Tyr Lys Asn Asp Leu Ile Leu Leu Gln Lys Lys Asn Met Gln
            900                 905                 910
Glu Pro Glu Phe Ala Tyr Tyr Asn Asp Phe Ser Ile Ser Thr Ser Ser
        915                 920                 925
Ile Cys Val Glu Lys His Asp Asn Lys Phe Glu Asn Leu Thr Ser Asn
    930                 935                 940
Gln Lys Leu Leu Phe Ser Asn Ala Lys Glu Gly Ser Val Lys Val Glu
945                 950                 955                 960
Ser Leu Gly Ile Gln Asn Leu Lys Val Phe Glu Lys Tyr Ile Ile Thr
                965                 970                 975
Pro Leu Gly Asp Lys Ile Lys Ala Asp Phe Gln Pro Arg Glu Asn Ile
            980                 985                 990
Ser Leu Lys Thr Ser Lys Lys Tyr  Gly Leu Arg
            995                 1000
```

US 11,326,157 B2

BASE EDITORS WITH IMPROVED PRECISION AND SPECIFICITY

CLAIM OF PRIORITY

This application is a national stage application of PCT/US2018/034719, filed May 25, 2018, which claims the benefit of U.S. Provisional Patent Application Ser. No. 62/511,296, filed on May 25, 2017; Ser. No. 62/541,544, filed on Aug. 4, 2017; and Ser. No. 62/622,676, filed on Jan. 26, 2018. The entire contents of the foregoing are hereby incorporated by reference.

FEDERALLY SPONSORED RESEARCH OR DEVELOPMENT

This invention was made with Government support under Grant Nos. GM118158 and HG009490 awarded by the National Institutes of Health. The Government has certain rights in the invention.

TECHNICAL FIELD

Described herein are methods and compositions for improving the genome-wide specificities of targeted base editing technologies.

BACKGROUND

Base editing (BE) technologies use an engineered DNA binding domain (such as RNA-guided, catalytically inactive Cas9 (dead Cas9 or dCas9), a nickase version of Cas9 (nCas9), or zinc finger (ZF) arrays) to recruit a cytidine deaminase domain to a specific genomic location to effect site-specific cytosine-thymine transition substitutions[1,2]. BE is a particularly attractive tool for treating genetic diseases that manifest in cellular contexts where making precise mutations by homology directed repair (HDR) would be therapeutically beneficial but are difficult to create with traditional nuclease-based genome editing technology. For example, it is challenging or impossible to achieve HDR outcomes in tissues composed primarily of slowly dividing or post-mitotic cell populations, since HDR pathways are restricted to the G2 and S phases of the cell cycle[3]. In addition, the efficiency of HDR repair can be substantially degraded before and after edits are created by the competing and more efficient induction of variable-length indel mutations caused by non-homologous end-joining-mediated repair of nuclease-induced breaks. By contrast, BE technology has the potential to allow practitioners to make highly controllable, highly precise mutations without the need for cell-type-variable DNA repair mechanisms.

SUMMARY

CRISPR base editor platforms (BE) possess the unique capability to generate precise, user-defined genome-editing events without the need for a donor DNA molecule. Base Editors (BEs) that include a single strand nicking CRISPR-Cas9 (nCas9) protein fused to a cytidine deaminase domain and uracil glycosylase inhibitor (UGI) (BE3) efficiently induce cytidine-to-thymidine (C-to-T) base transitions in a site-specific manner as determined by the CRISPR guide RNA (gRNA) spacer sequence[1]. As with all genome editing reagents, it is critical to first determine and then mitigate BE's capacity for generating off-target mutations before it is used for therapeutics so as to limit its potential for creating deleterious and irreversible genetically-encoded side-effects. Here we propose technological improvements to BE technology that will enable its maturation toward clinical relevance. First, we describe methods for limiting the absolute number of available cytosine substrates available for BE deamination by building BEs that make use of deaminases, either natural or engineered, that can only deaminate cytosines that exist in particular 2- or 3-nucleotide genomic contexts (Table 1).

The proteins can include one or more mutations listed in Table 7, e.g., to increase specificity of deaminase proteins or domains on their own or in any possible combinations. The proteins can include one or more mutations listed in Table 8, e.g., intended to alter the targetable motif sequence, optionally combined with any of the mutations in Table 7, e.g., to create engineered deaminase proteins or domains with altered and increased substrate sequence. Further, the proteins can include one or more mutations listed in Table 9, optionally combined with any of the mutations listed in Table 7 or Table 8 to create engineered deaminase proteins, e.g., with altered specificity for the first or third nucleotide in a trinucleotide motif and with increased specificity for its target motif relative to other possible deamination substrate motifs.

In some embodiments, the engineered variant of hAID, rAPOBEC1*, mAPOBEC3, BEC3A, hA,hAPOBEC3B, hAPOBEC3C, hAPOBEC3F, hAPOBEC3G or hAPOBEC3H comprises one or more mutations shown in Table 7, 8 and/or 9. In some embodiments, the mutation is N57A/G/Q/D/E; A71V; I96T; Y130F; or K60A/D/E, or a combination thereof.

In some embodiments, the engineered variant of hAID, rAPOBEC1*, mAPOBEC3, hAPOBEC3A, hAPOBEC3B, hAPOBEC3C, hAPOBEC3F, hAPOBEC3GQ or hAPOBEC3H comprises (i) one or more mutations shown in Table 7 and/or 8 and (ii) one or more mutations shown in Table 9.

In some embodiments, the engineered variant of hAID, rAPOBEC1*, mAPOBEC3, hAPOBEC3A, hAPOBEC3B, hAPOBEC3C, hAPOBEC3F, hAPOBEC3G or hAPOBEC3H comprises hAPOBEC3A with a mutation at one or more of N57 (preferably N57G or N57Q); K60 (preferably K60A or K60D), and/or Y130 (preferably Y130F); or hAID, rAPOBEC1*, mAPOBEC3, hAPOBEC3B, hAPOBEC3C, hAPOBEC3F, hAPOBEC3G or hAPOBEC3H with a mutation corresponding to N57 (e.g., at position 3 as shown in Table 7, e.g., a G at position 3). K60 (e.g., at position 4 as shown in Table 7, e.g., a D at position 4)), or Y130 (e.g., at position 6 as shown in Table 7, e.g., an F at position 6).

In some embodiments, the engineered variant of hAID, rAPOBEC1*, mAPOBEC3, hAPOBEC3A, hAPOBEC3B, hAPOBEC3C, hAPOBEC3F, hAPOBEC3G or hAPOBEC3H comprises hAPOBEC3A with a mutation at N57 (preferably N57G) and Y130 (preferably Y130F), or hAID, rAPOBEC1*, mAPOBEC3, hAPOBEC3B, hAPOBEC3C, hAPOBEC3F, hAPOBEC3Q or hAPOBEC3H with a mutation corresponding to N57 (e.g., at position 3 as shown in Table 7, e.g., a G at position 3) and a mutation corresponding to Y130 (e.g., at position 6 as shown in Table 7, e.g., a F at position 6).

In some embodiments, the engineered variant of hAID, rAPOBEC1*, mAPOBEC3, hAPOBEC3A, hAPOBEC3B, hAPOBEC3C, hAPOBEC3F, hAPOBEC3G or hAPOBEC3H comprises hAPOBEC3A with a mutation at A71 and/or 196, or hAID, rAPOBEC1*, mAPOBEC3, hAPOBEC3B, hAPOBEC3C, hAPOBEC3F, hAPOBEC3G or hAPOBEC3H with a mutation corresponding to A71 and/or 196 (e.g., as shown in table 10). For example, 196T, A71V, and Y130F each attenuate the editing activity of the deaminase from WT (which is critical because of off-target effects) without restoring much if any sequence preference, making them good candidates for all base editing sites.

In addition, provided herein are methods for treating a subject with beta thalassemia mutation HBB-28 (A>G), comprising delivering a therapeutically effective amount of a fusion protein of any of the preceding claims, wherein the deaminase comprises APO3A comprising a mutation at N57G or N57A or N57Q or K60A or K60D or Y130F, and preferably wherein the fusion protein comprises a ssDNA nicking or catalytically-inactive Cas9.

In some embodiments, the fusion protein is delivered as an RNP, mRNA, or plasmid.

In some embodiments, the methods include delivering the fusion protein ex vivo to a population of cells comprising CD34+ hematopoietic stem and/or progenitor cells collected from the subject under conditions sufficient for deamination of the mutated, and re-infusing the cells back into the subject.

Also provided herein are methods for deaminating a selected cytidine in a nucleic acid, the method comprising contacting the nucleic acid with a fusion protein or base editing system described herein.

Additionally, provided herein are compositions comprising a purified a fusion protein or base editing system as described herein.

Further, provided herein are nucleic acids encoding a fusion protein or base editing system described herein, as well as vectors comprising the nucleic acids, and host cells comprising the nucleic acids, e.g., stem cells, e.g., hematopoietic stem cells.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 2A and 2B show alignments for Recognition Loop 1 (RL1) and Loop 7, respectively (SEQ ID NOs:1-9). Both regions show low conservation across all proteins and have either been empirically demonstrated to significantly contribute to the sequence specificity of each enzyme or are predicted to do so based on homology. Alignment performed by Blosum62 matrix and visualized in Geneious.

FIGS. 3A-3B. Protein-DNA contacts made between APO3A and ssDNA substrate. RL1 residues are shown in magenta, Loop 7 residues are shown in red, ssDNA substrate is shown in yellow, and the remaining residues of APO3A are shown in gray. FIG. 3A shows the orientations of all residues in RL1 and Loop 7 that we propose to make substitution mutations to in order to alter or enhance the specificity of the deaminase domains described herein (SEQ ID NOs:1-9). FIG. 3B shows the base-specific hydrogen bond, shown as black dashed lines, formed between the thymine at the −1 position (relative to the target C) and D131 (SEQ ID NOs:10-18). PDB code: 5SWW.

DETAILED DESCRIPTION

Figure 1:
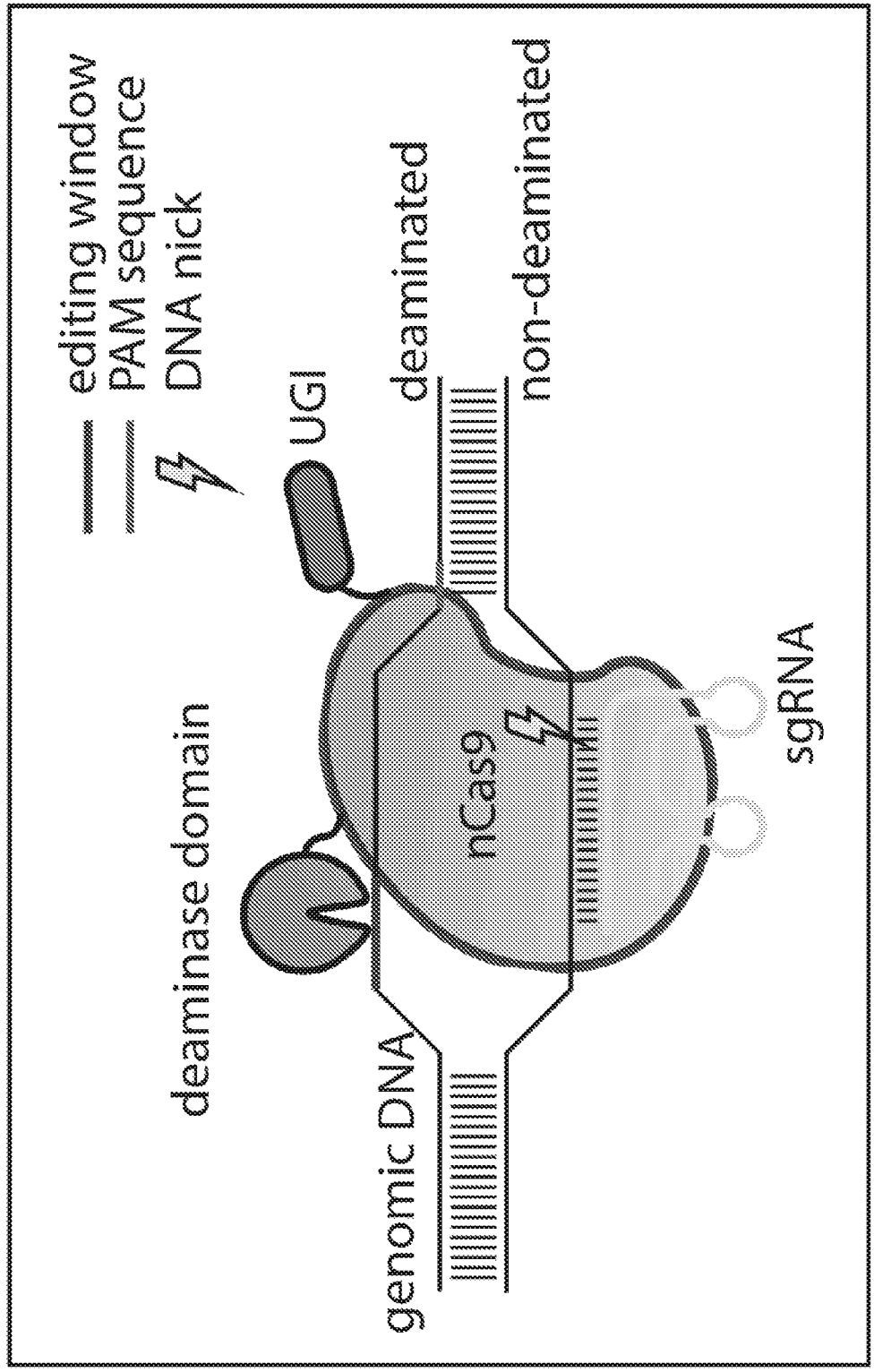
FIG. 1. Diagram of an exemplary typical high efficiency base editing system. A nicking Cas9 (nCas9) bearing a catalytically inactivating mutation at one of its two nuclease domains binds to the target site dictated by the variable spacer sequence of the sgRNA. The formation of a stable R-loop creates a ssDNA editing window on the non-deaminated strand. The Cas9 creates a single strand break in the genomic DNA, prompting the host cell to repair the lesion using the deaminated strand as a template, thus biasing repair towards the cytosine-thymine transition substitution.

In the most efficient BE configuration described to date, a cytidine deaminase (DA) domain and uracil glycosylase inhibitor (UGI; a small bacteriophage protein that inhibits host cell uracil deglycosylase (UDG), the enzyme responsible for excising uracil from the genome[1, 4]) are both fused to nCas9 (derived from either *Streptococcus pyogenes* Cas9 (SpCas9) or *Staphylococcus aureus* Cas9 (SaCas9). The nCas9 forms an R-loop at a target site specified by its single guide RNA (sgRNA) and recognition of an adjacent protospacer adjacent motif (PAM), leaving approximately 4-8 nucleotides of the non-target strand exposed as single stranded DNA (ssDNA) near the PAM-distal end of the R-loop (FIG. 1). This region of the ssDNA is the template that is able to be deaminated by the ssDNA-specific DA domain to produce a guanosine:uracil (G:U) mismatch and defines the editing window. The nCas9 nicks the non-deaminated strand of DNA, biasing conversion of the G:U mismatch to an adenine:thymine (A:T) base pair by directing the cell to repair the nick lesion using the deaminated strand as a template. To date, the DA domains described in these fusion proteins have been rat APOBEC1 (rAPO1), an activation-induced cytidine deaminase (AID) derived from lamprey termed CDA (PmCDA), human AID (hAID), or a hyperactive form of hAID lacking a nuclear export signall[12, 5-7]. BE technology was primarily established using the SpCas9 protein for its nCas9 domain (nSpCas9), but although herein we refer to nCas9, in general any Cas9-like nickase could be used based on any ortholog of the Cpf1 protein (including the related Cpf1 enzyme class), unless specifically indicated.

An important consideration for the use of BE in therapeutic settings will be to assess its genome-wide capacity for off-target mutagenesis and to modify the technology to minimize or, ideally, to eliminate the risks of stimulating deleterious off-target mutations. With current generation BE technology, we can predict three potential sources of off-target mutagenesis: (1) unwanted modification of cytosine bases within the on-target site because nCas9-stimulated R-loop formation can expose a total of 8 on-target nucleotides for deamination; (2) off-target R-loop formation (Cas9 has a well-documented ability to bind at off-target sites with varying degrees of homology to its sgRNA[8-9]) leading to cytosine deamination at these sites; and (3) BE-mediated deamination that might occur at sites without binding to DNA by the Cas9 part of the fusion (e.g., activity mediated from solution or at sites weakly specified only by the deaminase itself). Herein, we described technological improvements to BEs that can be used to reduce or eliminate potential unwanted BE mutagenesis.

Increasing the Specificity of Base Editors by Using Cytidine Deaminase Domains with Higher or Altered Target Site Preferences Current generation BE technology uses the cytosine deamination activity of rat APOBEC1 (rAPOBEC1) to effect cytosine-thymine transition substitutions in a window of approximately 8 nucleotides of single stranded DNA (ssDNA). The ssDNA target window is formed by the R-loop created by the nCas9 portion of the BE fusion protein and begins approximately 4 nucleotides downstream of the 5'-most nucleotide of the sgRNA complementarity region. Thus, the target C to be deaminated is within the gRNA target complementarity sequence. Within the target sequence, it needs to be located at positions 5, 6, 7, 8, or 9 counting from the 5'.

The rAPOBEC1 domain has little intrinsic substrate sequence specificity on its own and deaminates cytosines in all sequence contexts equally well unless the base immediately 5' to the target C is a G, in which case deamination is less efficient but still possible. In addition, when rAPOBEC1 is fused to nCas9 it appears to have processivity for multiple cytosines within the editing window[1]—a single binding event at the ssDNA target window often results in deamination of more than one cytosine in the window (if two or more cytosines are present).

Multiple deaminations per target window can result in undesired changes at the on-target binding site and at other off-target DNA sequences bound by nCas9 in the genome. To some degree, unwanted deaminations within the on-target editing window can be controlled by changing the length and flexibility of the protein linker separating rAPOBEC1 and nCas9; however, this control cannot be tuned to specific sequence locations in the editing window and still shows detectable deamination outside of the limited editing window[10].

To decrease or completely ablate undesired deamination of non-target cytosines within the on-target site's editing window, deamination of any cytosines at off-target sites, and limit unwanted processive deamination events at the on-target site, we built BEs using engineered deaminase domains with intrinsic specificity for short sequence motifs and/or non-processive deamination activity.

Base Editors

In some embodiments, the base editor is a deaminase that modifies cytosine DNA bases, e.g., a cytidine deaminase from the apolipoprotein B mRNA-editing enzyme, catalytic polypeptide-like (APOBEC) family of deaminases, including APOBEC1, APOBEC2, APOBEC3A, APOBEC3B, APOBEC3C, APOBEC3D/E, APOBEC3F, APOBEC3G APOBEC3H, APOBEC4 (see, e.g., Yang et al., J Genet Genomics. 2017 Sep. 20; 44(9):423-437); activation-induced cytidine deaminase (AID), e.g., activation induced cytidine deaminase (AICDA), cytosine deaminase 1 (CDA1), and CDA2, and cytosine deaminase acting on tRNA (CDAT). The following Table 1 provides exemplary sequences; other sequences can also be used.

TABLE 1

Exemplary Deaminases

| Deaminase | Nucleic Acid | Amino Acid |
|---|---|---|
| | GenBank Accession Nos. | |
| hAID/AICDA | NM_020661.3 isoform 1 | NP_065712.1 variant 1 |
| | NM_020661.3 isoform 2 | NP_065712.1 variant 2 |
| APOBEC1 | NM_001644.4 isoform a | NP_001635.2 variant 1 |
| | NM_005889.3 isoform b | NP_005880.2 variant 3 |
| APOBEC2 | NM_006789.3 | NP_006780.1 |
| APOBEC3A | NM_145699.3 isoform a | NP_663745.1 variant 1 |
| | NM_001270406.1 isoform b | NP_001257335.1 variant 2 |
| APOBEC3B | NM_004900.4 isoform a | NP_004891.4 variant 1 |
| | NM_001270411.1 isoform b | NP_001257340.1 variant 2 |
| APOBEC3C | NM_014508.2 | NP_055323.2 |
| APOBEC3D/E | NM_152426.3 | NP_689639.2 |
| APOBEC3F | NM_145298.5 isoform a | NP_660341.2 variant 1 |
| | NM_001006666.1 isoform b | NP_001006667.1 variant 2 |
| APOBEC3G | NM_021822.3 (isoform a) | NP_068594.1 (variant 1) |
| APOBEC3H | NM_001166003.2 | NP_001159475.2 (variant SV-200) |
| APOBEC4 | NM_203454.2 | NP_982279.1 |
| CDA1* | NM_127515.4 | NP_179547.1 |

*from *Saccharomyces cerevisiae* S288C

The human AID (hAID), human APOBEC3 and mouse APOBEC3 enzymes (APO3A-hAPO3H, mAPO3) possess specificity for one, two or three additional nucleotides surrounding the target cytosine (Table 2)[11-16]. The added specificity from 1 to 3 additional nucleotides would result in a 4- to 64-fold decreased probability of a non-target cytosine in a BE editing window being available for deamination in randomly distributed DNA. This would substantially enhance specificity of base editing enzymes within the genome at both on-target sites and nCas9 off-target sites with a high degree of similarity to the sgRNA, and would also contribute to limiting potential spurious sgRNA/nCas9-independent deamination throughout the genome by greatly reducing the number of total substrate sites in the genome. Importantly, the intrinsic sequence specificity of the hAPO3 and mAPO3 enzymes raises the possibility that these proteins could be engineered to alter or reassign their target sequence specificities. In this scenario, one could potentially engineer many different 2- and 3-bp recognizing deaminases to accommodate each target substrate sequence signature of interest.

TABLE 2

Cytidine deaminase domains described in this work and their substrate sequence preferences.

| Variant | Nucleotide sequence preference |
|---|---|
| hAID | 5'-WRC |
| rAPOBEC1* | 5'-TC ≥ CC ≥ AC > GC |
| mAPOBEC3 | 5'-TYC |

TABLE 2-continued

Cytidine deaminase domains described in this work and their substrate sequence preferences.

| Variant | Nucleotide sequence preference |
|---|---|
| hAPOBEC3A | 5'-TCY |
| hAPOBEC3B | 5'-TCR > TCT |
| hAPOBEC3C | 5'-WYC |
| hAPOBEC3F | 5'-TTC |
| hAPOBEC3G | 5'-CCC |
| hAPOBEC3H | 5'-TTCA ~ TTCT ~ TTCG > ACCCA > TGCA |

Nucleotide positions that are poorly specified or are permissive of two or more nucleotides are annotated according to IUPAC codes, where W = A or T, R = A or G, and Y = C or T.

Each endogenous hAPO3 and mAPO3 enzyme has an intrinsic 2-3 nt target substrate motif preference at which it can act. For instance, APO3A deaminates the bold cytosine in TC(A/G), while hAPO3G targets substrates of the form CCC. It would be advantageous to be able to modify the range of sequence motifs that are targetable by a given APO3 enzyme so as to increase the overall targeting range of this proposed class of substrate-specific APO3-containing BE reagents. In addition, engineering the substrate-specificity-determining residues of the APO3 enzymes will allow us to not only alter the preferred substrate site, but also improve the specificity of the APO3 enzyme for its preferred site relative to other closely matched di- or tri-nucleotide signatures that may exist abundantly across the genome. hAPO3 enzymes recognize their cognate sequence motifs through direct contacts formed between residues in two recognition loops with variable sequence composition termed recognition loop 1 (RL1) and Loop 7[12-13, 17-22] (see Table 3, FIGS. 2A-2B, and FIGS. 3A-3B). Others have previously described substitution mutations made to these residues that relax or alter the specificity of these domains. For instance, mutating hAPO3G Loop 7 residues D316 and D317 to arginine changes the substrate specificity of the enzyme from CCC to CCC (wherein the bold C represents the substrate for deamination)[23]. Mutating hAPO3F D311A increases targeting of TGC and TCC, where the unmodified enzyme prefers to target TTC[15]. Further, a chimeric APO3A protein in which the RL1 residues have been replaced by the RL1 residues of hAPO3G significantly relaxes specificity of the enzyme[24], and substituting hAID Loop 7 residues with those from hAPO3G or hAPO3F changes the target sequence profiles of the mutant hAID enzymes to resemble those of the donor enzymes[25]. This work establishes that substitution mutations to residues in RL1 and Loop 7 are predicted to alter specificity of the APO3 proteins by altering the base-specific contacts made between the protein and the target ssDNA, but as yet there have been no reports of re-engineering APO3 substrate sequence specificity beyond these initial studies. Further, to our knowledge, no groups have described strategies to heighten the specificity of these domains for their target sequence motifs.

TABLE 3

| | Recognition Loop Residues | |
|---|---|---|
| Deaminase | Recognition loop 1 residues | Loop 7 residues |
| hAID | V18 - K22 | A111 - P123 |
| rAPOBEC1* | D11 - R15 | A117 - R126 |
| mAPOBEC3* | L33 - K37 | S129 - E138 |
| hAPOBEC3A | G25 - R28 | A127 - L135 |
| hAPOBEC3C | L24 - N28 | A121 - C130 |
| hAPOBEC3G | E209 - R213 | A312 - R320 |
| hAPOBEC3H* | K16 - Y23 | S109 - P118 |
| hAPOBEC3F | L207 - Y211 | A304 - D313 |

Each Recognition loop 1 and Loop 7 region represents a region of the enzyme either known to contribute to the sequence specificity of the enzyme or predicted to contribute to sequence specificity based on sequence alignment (see FIGS. 3A-3B) where structural information is lacking (*indicates which proteins lack sufficient structural information). All protein sequences acquired from uniprot.org. All positional information refers to positions within the full-length protein sequences as described below.

Figure 2A:
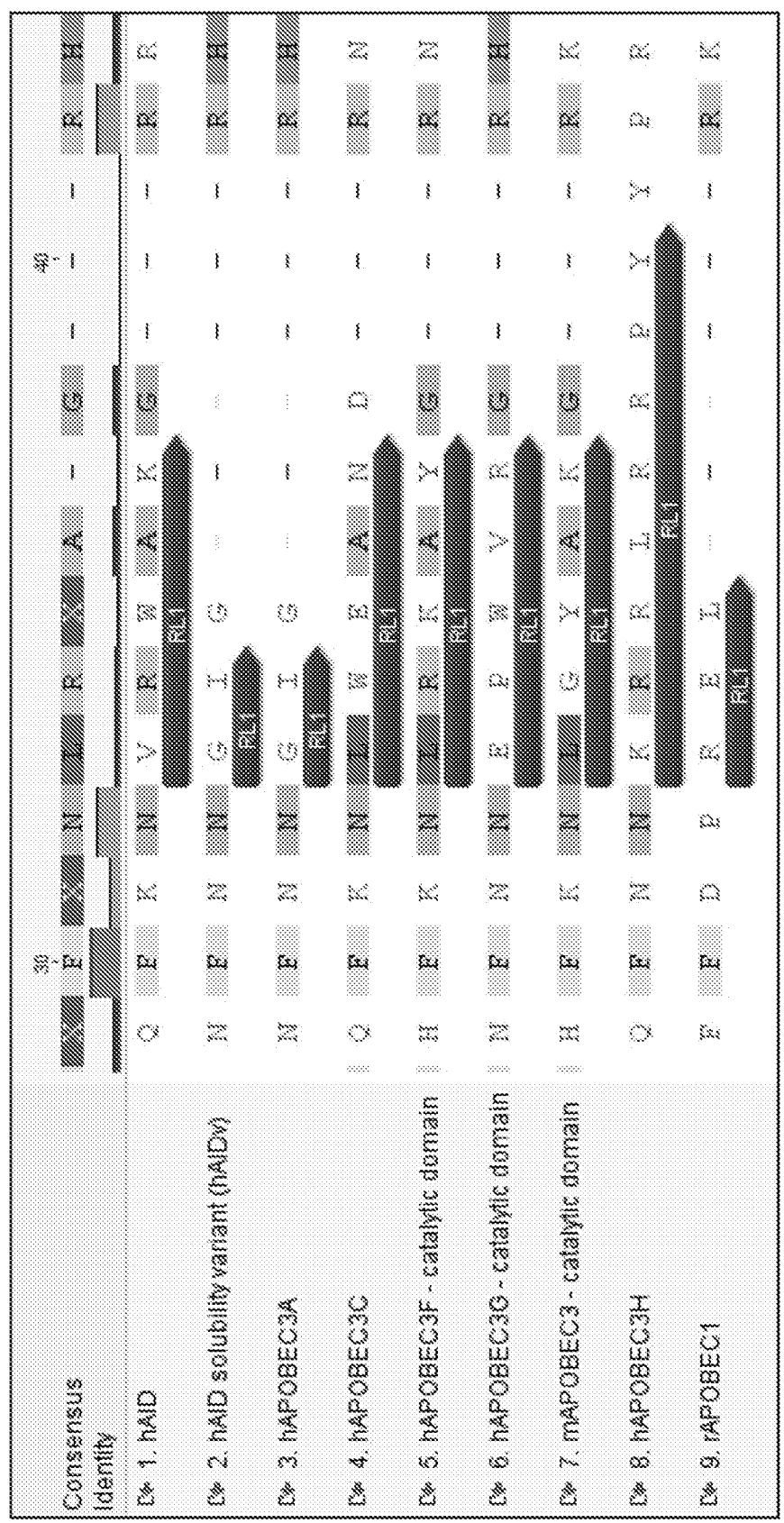
FIGS. 2A-2B.
Figure 2B:
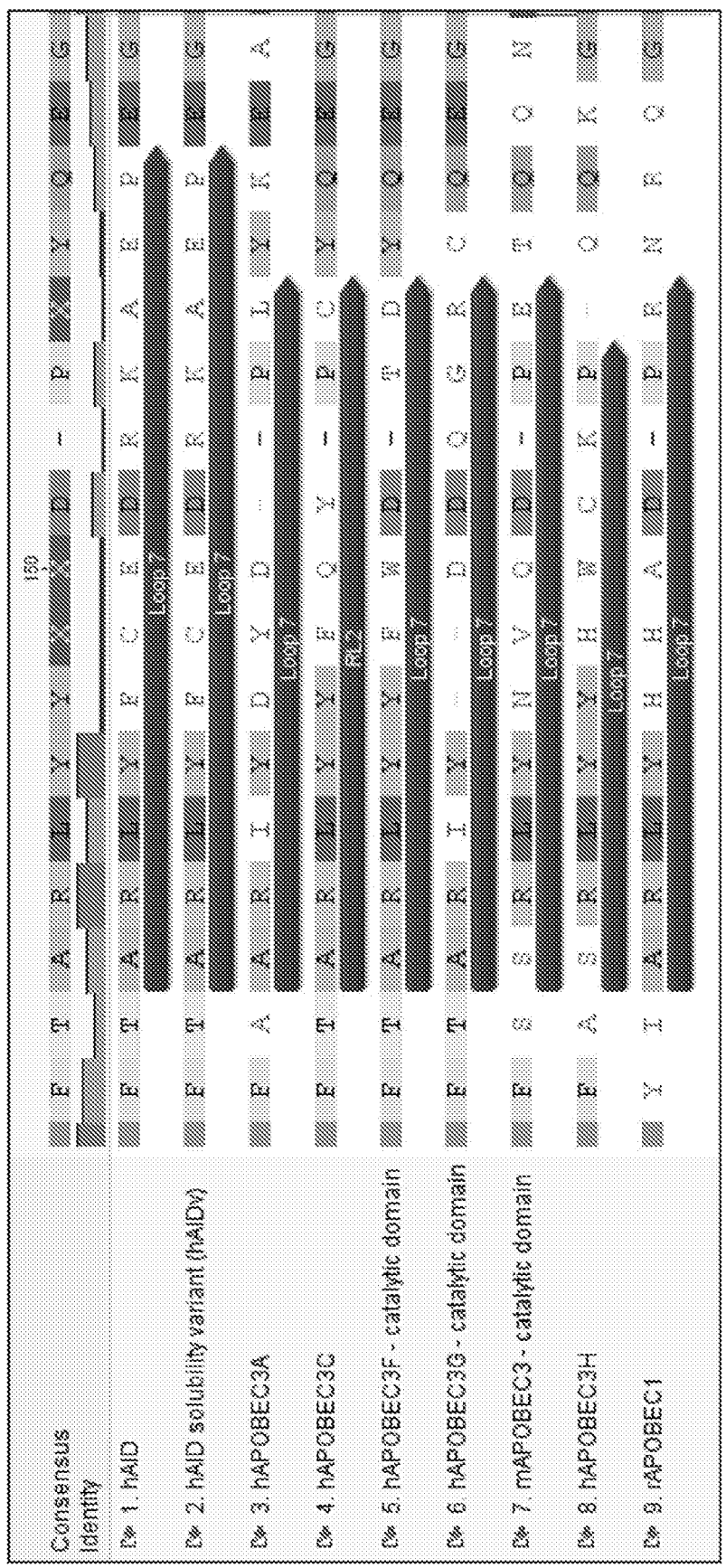

To this end, substitution mutations can be made to residues present in RL1 and/or Loop 7 (see Table 3 for residues corresponding to each APO3 or AID enzyme and FIGS. 2A-2B for an alignment of these proteins). To sample the greatest number of amino acid substitution combinations at positions in RL1 or Loop 7, we will randomize the amino acids in these loops and use a bacterial selection scheme to select for the library members with robust deamination activity on the desired sequence. In the case of Loop 7, residues believed to be most responsible for specifying the sequence motif will be individually mutated to residues that might be expected to form base-specific interactions with the desired sequence motif and the remaining positions in Loop 7 will be randomized. For example, APO3A residue D131 is known to form a hydrogen bond with 5'-TCY (wherein the bold T represents the base-specific contact). To alter the sequence specificity of APO3A from TCT>ACT, we will first design APO3A mutants bearing substitutions of D131 to N, Q, or R. Each of these APO3A variants will then be modified at positions 132-134 by cloning a synthesized degenerate oligonucleotide library made using an NNB, NNS or NNK reduced codon set (where N=A/C/G/T, B=C/G/T, S=C/G, and K=G/T).

The substitution mutations made to each of these residues include any of the 20 canonical amino acids in any combination with substitution mutations made to any of the other specified residue positions. Further, these mutations may be made in combination with truncating the enzymes in Table 3 to the minimal domain required for catalytic activity (catalytic domain; CD). See Exemplary Protein Sequences for examples of CDs derived from a subset of the enzymes described herein. These mutations may also be made in the presence or absence of all or any combination of 5 substitution mutations previously demonstrated to increase solubility and catalytic activity of hAPO3G (see Table 4 for a complete list of the homologous substitution mutations for each APO or AID enzyme described herein). Notably, the deaminase domains listed in Table 1 may have favorable intrinsic properties relative to rAPOBEC1 absent of any engineering we might do. As such, we describe herein the unmodified domains listed in Table 1 in addition to any engineered variants we may produce.

TABLE 4

| | Exemplary Substitution Mutations | | | | |
|---|---|---|---|---|---|
| Deaminase | Sub. 1 | Sub. 2 | Sub. 3 | Sub. 4 | Sub. 5 |
| hAID | — | — | F109K | — | — |
| rAPOBEC1* | L39K | — | Y115K | — | — |

TABLE 4-continued

Exemplary Substitution Mutations

| Deaminase | Sub. 1 | Sub. 2 | Sub. 3 | Sub. 4 | Sub. 5 |
|---|---|---|---|---|---|
| mAPOBEC3* | — | — | F127K | — | — |
| hAPOBEC3A | — | — | F125K | — | C171A |
| hAPOBEC3G | L234K | C243A | F310K | C321A | C356A |
| hAPOBEC3H* | — | — | F107K | — | — |
| hAPOBEC3F | — | — | F302K | — | — |

Each substitution mutation represents a residue of the enzyme either known to contribute to stability and solubility of the enzyme or predicted to contribute to sequence specificity based on sequence alignment to hAPOBEC3G where structural information is lacking (* indicates which proteins lack sufficient structural information). All positional information refers to the wild-type protein sequences acquired from uniprot.org. The exact position of these residues may change in engineered variants such as hAIDv. All positional information refers to positions within the full-length protein sequences as described below.

CRISPR-Cas Nucleases

The sequence specific deaminases described herein are fused to a Cas9 nickase. Although herein we refer to nCas9, in general any Cas9-like nickase could be used based on any ortholog of the Cpf1 protein (including the related Cpf1 enzyme class), unless specifically indicated. Table 5 provides an exemplary list.

TABLE 5

List of Exemplary Cas9 Orthologs

| Ortholog | UniProt Accession Number | Nickase Mutations/ Catalytic residues |
|---|---|---|
| S. pyogenes Cas9 (SpCas9) | Q99ZW2 | D10A, E762A, H840A, N854A, N863A, D986A[18] |
| S. aureus Cas9 (SaCas9) | J7RUA5 | D10A and N58018[19] |
| S. thermophilus Cas9 (St1Cas9) | G3ECR1 | D31A and N891A[20] |
| S. pasteurianus Cas9 (SpaCas9) | F5X275 | D10, H599* |
| C. jejuni Cas9 (CjCas9) | Q0P897 | D8A, H559A[21] |
| F. novicida Cas9 (FnCas9) | A0Q5Y3 | D11, N995[22] |
| P. lavamentivorans Cas9 (PlCas9) | A7HP89 | D8, H601* |
| C. lari Cas9 (ClCas9) | G1UFN3 | D7, H567* |
| F. novicida Cpf1 (FnCpf1) | A0Q7Q2 | D917, E1006, D1255[23] |
| M. bovoculi Cpf1 (MbCpf1) | Sequence given at end | N/A** |
| A. sp. BV3L6 (AsCpf1) | U2UMQ6 | D908, 993E, Q1226, D1263[24] |
| L. bacterium N2006 (LbCpf1) | A0A182DWE3 | D832A[25] |

These orthologs, and mutants and variants thereof as known in the art, can be used in any of the fusion proteins described herein. See, e.g., WO 2017/040348 (which describes variants of SaCas9 and SpCas 9 with increased specificity) and WO 2016/141224 (which describes variants of SaCas9 and SpCas 9 with altered PAM specificity).

The Cas9 nuclease from *S. pyogenes* (hereafter simply Cas9) can be guided via simple base pair complementarity between 17-20 nucleotides of an engineered guide RNA (gRNA), e.g., a single guide RNA or crRNA/tracrRNA pair, and the complementary strand of a target genomic DNA sequence of interest that lies next to a protospacer adjacent motif (PAM), e.g., a PAM matching the sequence NGG or NAG (Shen et al., Cell Res (2013); Dicarlo et al., Nucleic Acids Res (2013); Jiang et al., Nat Biotechnol 31, 233-239 (2013); Jinek et al., Elife 2, e00471 (2013); Hwang et al., Nat Biotechnol 31, 227-229 (2013); Cong et al., Science 339, 819-823 (2013); Mali et al., Science 339, 823-826 (2013c); Cho et al., Nat Biotechnol 31, 230-232 (2013); Jinek et al., Science 337, 816-821 (2012)). The engineered CRISPR from *Prevotella* and *Francisella* 1 (Cpf1) nuclease can also be used, e.g., as described in Zetsche et al., Cell 163, 759-771 (2015); Schunder et al., Int J Med Microbiol 303, 51-60 (2013); Makarova et al., Nat Rev Microbiol 13, 722-736 (2015); Fagerlund et al., Genome Biol 16, 251 (2015). Unlike SpCas9, Cpf1 requires only a single 42-nt crRNA, which has 23 nt at its 3' end that are complementary to the protospacer of the target DNA sequence (Zetsche et al., 2015). Furthermore, whereas SpCas9 recognizes an NGG PAM sequence that is 3' of the protospacer, AsCpf1 and LbCp1 recognize TTTN PAMs that are found 5' of the protospacer (Id.).

In some embodiments, the present system utilizes a wild type or variant Cas9 protein from *S. pyogenes* or *Staphylococcus aureus*, or a wild type Cpf1 protein from *Acidaminococcus* sp. BV3L6 or *Lachnospiraceae bacterium* ND2006 either as encoded in bacteria or codon-optimized for expression in mammalian cells and/or modified in its PAM recognition specificity and/or its genome-wide specificity. A number of variants have been described; see, e.g., WO 2016/141224, PCT/US2016/049147, Kleinstiver et al., Nat Biotechnol. 2016 August; 34(8):869-74; Tsai and Joung, Nat Rev Genet. 2016 May; 17(5):300-12; Kleinstiver et al., Nature. 2016 Jan. 28; 529(7587):490-5; Shmakov et al., Mol Cell. 2015 Nov. 5; 60(3):385-97; Kleinstiver et al., Nat Biotechnol. 2015 December; 33(12):1293-1298; Dahlman et al., Nat Biotechnol. 2015 November; 33(11):1159-61; Kleinstiver et al., Nature. 2015 Jul. 23; 523(7561):481-5; Wyvekens et al., Hum Gene Ther. 2015 July; 26(7):425-31; Hwang et al., Methods Mol Biol. 2015; 1311:317-34; Osborn et al., Hum Gene Ther. 2015 February; 26(2):114-26; Konermann et al., Nature. 2015 Jan. 29; 517(7536):583-8; Fu et al., Methods Enzymol. 2014; 546:21-45; and Tsai et al., Nat Biotechnol. 2014 June; 32(6):569-76, inter alia. The guide RNA is expressed or present in the cell together with the Cas9 or Cpf1. Either the guide RNA or the nuclease, or both, can be expressed transiently or stably in the cell or introduced as a purified protein or nucleic acid.

In some embodiments, the Cas9 also includes one of the following mutations, which reduce nuclease activity of the Cas9; e.g., for SpCas9, mutations at D10A or H840A (which creates a single-strand nickase).

In some embodiments, the SpCas9 variants also include mutations at one of the following amino acid positions, which destroy the nuclease activity of the Cas9: D10, E762, D839, H983, or D986 and H840 or N863, e.g., D10A/D10N and H840A/H840N/H840Y, to render the nuclease portion of the protein catalytically inactive; substitutions at these positions could be alanine (as they are in Nishimasu al., Cell 156, 935-949 (2014)), or other residues, e.g., glutamine, asparagine, tyrosine, serine, or aspartate, e.g., E762Q, H983N, H983Y, D986N, N863D, N863S, or N863H (see WO 2014/152432).

In some embodiments, the Cas9 is fused to one or more Uracil glycosylase inhibitor (UGI) sequences; an exemplary UGI sequence is as follows: TNLSDIIEKETGKQLVIQE-SILMLPEEVEEVIGNKPESDILVHTAYDES TDENVM LLTSDAPEYKPWALVIQDSNGENKIKML (SEQ ID NO:45). The UGI can be N terminal, C terminal, or absent (and optionally expressed in trans, e.g., separately, or provided or administered separately).

Methods of Use

The present compositions and methods can be used to enhance genome-wide specificity by engineered APO3A deaminases. For example, APO3A N57G employed in the BE3 architecture has increased genome-wide specificity at off target sites determined by the identity of the spacer sequence of the guide RNA when delivered by transient plasmid transfection. In addition, the methods can include delivery of APO3A BE3 with any of the mutations in Table 7, e.g., using RNP or mRNA transfection to limit genome-wide off target mutagenesis of base editor reagents. Additionally, the APO3A BE3 with any of the mutations in Table 7 (by themselves or together) can be delivered using transient plasmid transfection, RNP, or mRNA where the ssDNA nicking or catalytically-inactive Cas9 (nCas9) is any engineered SpCas9 protein[46] that recognizes an orthogonal PAM sequence to the SpCas9 NGG PAM in order to limit off target mutagenesis by the fusion protein. Additionally, APO3A can also be used with any of the mutations in Table 7 fused to S. aureus Cas9 or the engineered S. aureus Cas9 that recognizes an orthogonal PAM sequence[47]

Variants

In some embodiments, the components of the fusion proteins are at least 80%, e.g., at least 85%, 90%, 95%, 97%, or 99% identical to the amino acid sequence of a exemplary sequence (e.g., as provided herein), e.g., have differences at up to 5%, 10%, 15%, or 20% of the residues of the exemplary sequence replaced, e.g., with conservative mutations, in addition to the mutations described herein. In preferred embodiments, the variant retains desired activity of the parent, e.g., the nickase activity, and/or the ability to interact with a guide RNA and/or target DNA).

To determine the percent identity of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90% or 100%. The nucleotides at corresponding amino acid positions or nucleotide positions are then compared. When a position in the first sequence is occupied by the same nucleotide as the corresponding position in the second sequence, then the molecules are identical at that position (as used herein nucleic acid "identity" is equivalent to nucleic acid "homology"). The percent identity between the two sequences is a function of the number of identical positions shared by the sequences, taking into account the number of gaps, and the length of each gap, which need to be introduced for optimal alignment of the two sequences. Percent identity between two polypeptides or nucleic acid sequences is determined in various ways that are within the skill in the art, for instance, using publicly available computer software such as Smith Waterman Alignment (Smith, T. F. and M. S. Waterman (1981) J Mol Biol 147:195-7); "BestFit" (Smith and Waterman, Advances in Applied Mathematics, 482-489 (1981)) as incorporated into GeneMatcher Plus™, Schwarz and Dayhof (1979) Atlas of Protein Sequence and Structure, Dayhof, M. O., Ed, pp 353-358; BLAST program (Basic Local Alignment Search Tool; (Altschul, S. F., W. Gish, et al. (1990) J Mol Biol 215: 403-10), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins or nucleic acids, the length of comparison can be any length, up to and including full length (e.g., 5%, 10%, 20%, 30%, 40%, 50%, 60%, 70%, 80%, 90%, 95%, or 100%). For purposes of the present compositions and methods, at least 80% of the full length of the sequence is aligned.

For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

Also provided herein are isolated nucleic acids encoding the split deaminase fusion proteins, vectors comprising the isolated nucleic acids, optionally operably linked to one or more regulatory domains for expressing the variant proteins, and host cells, e.g., mammalian host cells, comprising the nucleic acids, and optionally expressing the variant proteins. In some embodiments, the host cells are stem cells, e.g., hematopoietic stem cells.

The split deaminase fusion proteins described herein can be used for altering the genome of a cell. The methods generally include expressing or contacting the split deaminase fusion proteins in the cells; in versions using one or two Cas9s, the methods include using a guide RNA having a region complementary to a selected portion of the genome of the cell. Methods for selectively altering the genome of a cell are known in the art, see, e.g., U.S. Pat. No. 8,993,233; US 20140186958; U.S. Pat. No. 9,023,649; WO/2014/099744; WO 2014/089290; WO2014/144592; WO144288; WO2014/204578; WO2014/152432; WO2115/099850; U.S. Pat. No. 8,697,359; US20160024529; US20160024524; US20160024523; US20160024510; US20160017366; US20160017301; US20150376652; US20150356239; US20150315576; US20150291965; US20150252358; US20150247150; US20150232883; US20150232882; US20150203872; US20150191744; US20150184139; US20150176064; US20150167000; US20150166969; US20150159175; US20150159174; US20150093473; US20150079681; US20150067922; US20150056629; US20150044772; US20150024500; US20150024499; US20150020223; US20140356867; US20140295557; US20140273235; US20140273226; US20140273037; US20140189896; US20140113376; US20140093941; US20130330778; US20130288251; US20120088676; US20110300538; US20110236530; US20110217739; US20110002889; US20100076057; US20110189776; US20110223638; US20130130248; US20150050699; US20150071899; US20150050699; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; US20140170753;

WO/2008/108989; WO/2010/054108; WO/2012/164565; WO/2013/098244; WO/2013/176772; US 20150071899; Makarova et al., "Evolution and classification of the CRISPR-Cas systems" 9(6) Nature Reviews Microbiology 467-477 (1-23) (June 2011); Wiedenheft et al., "RNA-guided genetic silencing systems in bacteria and archaea" 482 Nature 331-338 (Feb. 16, 2012); Gasiunas et al., "Cas9-crRNA ribonucleoprotein complex mediates specific DNA cleavage for adaptive immunity in bacteria" 109(39) Proceedings of the National Academy of Sciences USA E2579-E2586 (Sep. 4, 2012); Jinek et al., "A Programmable Dual-RNA-Guided DNA Endonuclease in Adaptive Bacterial Immunity" 337 Science 816-821 (Aug. 17, 2012); Carroll, "A CRISPR Approach to Gene Targeting" 20(9) Molecular Therapy 1658-1660 (September 2012); U.S. Appl. No. 61/652,086, filed May 25, 2012; Al-Attar et al., Clustered Regularly Interspaced Short Palindromic Repeats (CRISPRs): The Hallmark of an Ingenious Antiviral Defense Mechanism in Prokaryotes, Biol Chem. (2011) vol. 392, Issue 4, pp. 277-289; Hale et al., Essential Features and Rational Design of CRISPR RNAs That Function With the Cas RAMP Module Complex to Cleave RNAs, Molecular Cell, (2012) vol. 45, Issue 3, 292-302.

In some embodiments, the fusion proteins include a linker between the DNA binding domain (e.g., ZFN, TALE, or nCas9) and the BE domains. Linkers that can be used in these fusion proteins (or between fusion proteins in a concatenated structure) can include any sequence that does not interfere with the function of the fusion proteins. In preferred embodiments, the linkers are short, e.g., 2-20 amino acids, and are typically flexible (i.e., comprising amino acids with a high degree of freedom such as glycine, alanine, and serine). In some embodiments, the linker comprises one or more units consisting of GGGS (SEQ ID NO:46) or GGGGS (SEQ ID NO:47), e.g., two, three, four, or more repeats of the GGGS (SEQ ID NO:47) or GGGGS (SEQ ID NO:46) unit. Other linker sequences can also be used.

In some embodiments, the split deaminase fusion protein includes a cell-penetrating peptide sequence that facilitates delivery to the intracellular space, e.g., HIV-derived TAT peptide, penetratins, transportans, or hCT derived cell-penetrating peptides, see, e.g., Caron et al., (2001) Mol Ther. 3(3):310-8; Langel, Cell-Penetrating Peptides: Processes and Applications (CRC Press, Boca Raton Fla. 2002); El-Andaloussi et al., (2005) Curr Pharm Des. 11(28):3597-611; and Deshayes et al., (2005) Cell Mol Life Sci. 62(16):1839-49.

Cell penetrating peptides (CPPs) are short peptides that facilitate the movement of a wide range of biomolecules across the cell membrane into the cytoplasm or other organelles, e.g. the mitochondria and the nucleus. Examples of molecules that can be delivered by CPPs include therapeutic drugs, plasmid DNA, oligonucleotides, siRNA, peptide-nucleic acid (PNA), proteins, peptides, nanoparticles, and liposomes. CPPs are generally 30 amino acids or less, are derived from naturally or non-naturally occurring protein or chimeric sequences, and contain either a high relative abundance of positively charged amino acids, e.g. lysine or arginine, or an alternating pattern of polar and non-polar amino acids. CPPs that are commonly used in the art include Tat (Frankel et al., (1988) Cell. 55:1189-1193, Vives et al., (1997) J. Biol. Chem. 272:16010-16017), penetratin (Derossi et al., (1994) J. Biol. Chem. 269:10444-10450), polyarginine peptide sequences (Wender et al., (2000) Proc. Natl. Acad. Sci. USA 97:13003-13008, Futaki et al., (2001) J. Biol. Chem. 276:5836-5840), and transportan (Pooga et al., (1998) Nat. Biotechnol. 16:857-861).

CPPs can be linked with their cargo through covalent or non-covalent strategies. Methods for covalently joining a CPP and its cargo are known in the art, e.g. chemical cross-linking (Stetsenko et al., (2000) J. Org. Chem. 65:4900-4909, Gait et al. (2003) Cell. Mol. Life. Sci. 60:844-853) or cloning a fusion protein (Nagahara et al., (1998) Nat. Med. 4:1449-1453). Non-covalent coupling between the cargo and short amphipathic CPPs comprising polar and non-polar domains is established through electrostatic and hydrophobic interactions.

CPPs have been utilized in the art to deliver potentially therapeutic biomolecules into cells. Examples include cyclosporine linked to polyarginine for immunosuppression (Rothbard et al., (2000) Nature Medicine 6(11):1253-1257), siRNA against cyclin B1 linked to a CPP called MPG for inhibiting tumorigenesis (Crombez et al., (2007) Biochem Soc. Trans. 35:44-46), tumor suppressor p53 peptides linked to CPPs to reduce cancer cell growth (Takenobu et al., (2002) Mol. Cancer Ther. 1(12):1043-1049, Snyder et al., (2004) PLoS Biol. 2:E36), and dominant negative forms of Ras or phosphoinositol 3 kinase (PI3K) fused to Tat to treat asthma (Myou et al., (2003) J. Immunol. 171:4399-4405).

CPPs have been utilized in the art to transport contrast agents into cells for imaging and biosensing applications. For example, green fluorescent protein (GFP) attached to Tat has been used to label cancer cells (Shokolenko et al., (2005) DNA Repair 4(4):511-518). Tat conjugated to quantum dots have been used to successfully cross the blood-brain barrier for visualization of the rat brain (Santra et al., (2005) Chem. Commun. 3144-3146). CPPs have also been combined with magnetic resonance imaging techniques for cell imaging (Liu et al., (2006) Biochem. and Biophys. Res. Comm. 347(1):133-140). See also Ramsey and Flynn, Pharmacol Ther. 2015 Jul. 22. pii: S0163-7258(15)00141-2.

Alternatively or in addition, the split deaminase fusion proteins can include a nuclear localization sequence, e.g., SV40 large T antigen NLS (PKKKRRV (SEQ ID NO:48)) and nucleoplasmin NLS (KRPAATKKAGQAKKKK (SEQ ID NO:49)). Other NLSs are known in the art; see, e.g., Cokol et al., EMBO Rep. 2000 Nov. 15; 1(5): 411-415; Freitas and Cunha, Curr Genomics. 2009 December; 10(8): 550-557.

In some embodiments, the split deaminase fusion proteins include a moiety that has a high affinity for a ligand, for example GST, FLAG or hexahistidine sequences. Such affinity tags can facilitate the purification of recombinant split deaminase fusion proteins.

For methods in which the split deaminase fusion proteins are delivered to cells, the proteins can be produced using any method known in the art, e.g., by in vitro translation, or expression in a suitable host cell from nucleic acid encoding the split deaminase fusion protein; a number of methods are known in the art for producing proteins. For example, the proteins can be produced in and purified from yeast, E. coli, insect cell lines, plants, transgenic animals, or cultured mammalian cells; see, e.g., Palomares et al., "Production of Recombinant Proteins: Challenges and Solutions," Methods Mol Biol. 2004; 267:15-52. In addition, the split deaminase fusion proteins can be linked to a moiety that facilitates transfer into a cell, e.g., a lipid nanoparticle, optionally with a linker that is cleaved once the protein is inside the cell. See, e.g., LaFountaine et al., Int J Pharm. 2015 Aug. 13; 494(1): 180-194.

Expression Systems

To use the split deaminase fusion proteins described herein, it may be desirable to express them from a nucleic acid that encodes them. This can be performed in a variety of ways. For example, the nucleic acid encoding the split deaminase fusion can be cloned into an intermediate vector for transformation into prokaryotic or eukaryotic cells for replication and/or expression. Intermediate vectors are typically prokaryote vectors, e.g., plasmids, or shuttle vectors, or insect vectors, for storage or manipulation of the nucleic acid encoding the split deaminase fusion for production of the split deaminase fusion protein. The nucleic acid encoding the split deaminase fusion protein can also be cloned into an expression vector, for administration to a plant cell, animal cell, preferably a mammalian cell or a human cell, fungal cell, bacterial cell, or protozoan cell.

To obtain expression, a sequence encoding a split deaminase fusion protein is typically subcloned into an expression vector that contains a promoter to direct transcription. Suitable bacterial and eukaryotic promoters are well known in the art and described, e.g., in Sambrook et al., Molecular Cloning, A Laboratory Manual (3d ed. 2001); Kriegler, Gene Transfer and Expression: A Laboratory Manual (1990); and Current Protocols in Molecular Biology (Ausubel et al., eds., 2010). Bacterial expression systems for expressing the engineered protein are available in, e.g., *E. coli, Bacillus* sp., and *Salmonella* (Palva et al., 1983, Gene 22:229-235). Kits for such expression systems are commercially available. Eukaryotic expression systems for mammalian cells, yeast, and insect cells are well known in the art and are also commercially available.

The promoter used to direct expression of a nucleic acid depends on the particular application. For example, a strong constitutive promoter is typically used for expression and purification of fusion proteins. In contrast, when the split deaminase fusion protein is to be administered in vivo for gene regulation, either a constitutive or an inducible promoter can be used, depending on the particular use of the split deaminase fusion protein. In addition, a preferred promoter for administration of the split deaminase fusion protein can be a weak promoter, such as HSV TK or a promoter having similar activity. The promoter can also include elements that are responsive to transactivation, e.g., hypoxia response elements, Gal4 response elements, lac repressor response element, and small molecule control systems such as tetracycline-regulated systems and the RU-486 system (see, e.g., Gossen & Bujard, 1992, Proc. Natl. Acad. Sci. USA, 89:5547; Oligino et al., 1998, Gene Ther., 5:491-496; Wang et al., 1997, Gene Ther., 4:432-441; Neering et al., 1996, Blood, 88:1147-55; and Rendahl et al., 1998, Nat. Biotechnol., 16:757-761).

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to the nucleic acid sequence encoding the split deaminase fusion protein, and any signals required, e.g., for efficient polyadenylation of the transcript, transcriptional termination, ribosome binding sites, or translation termination. Additional elements of the cassette may include, e.g., enhancers, and heterologous spliced intronic signals.

The particular expression vector used to transport the genetic information into the cell is selected with regard to the intended use of the split deaminase fusion protein, e.g., expression in plants, animals, bacteria, fungus, protozoa, etc.

Standard bacterial expression vectors include plasmids such as pBR322 based plasmids, pSKF, pET23D, and commercially available tag-fusion expression systems such as GST and LacZ.

Expression vectors containing regulatory elements from eukaryotic viruses are often used in eukaryotic expression vectors, e.g., SV40 vectors, papilloma virus vectors, and vectors derived from Epstein-Barr virus. Other exemplary eukaryotic vectors include pMSG pAV009/A+, pMTO10/ A+, pMAMneo-5, baculovirus pDSVE, and any other vector allowing expression of proteins under the direction of the SV40 early promoter, SV40 late promoter, metallothionein promoter, murine mammary tumor virus promoter, Rous sarcoma virus promoter, polyhedrin promoter, or other promoters shown effective for expression in eukaryotic cells.

The vectors for expressing the split deaminase fusion protein can include RNA Pol III promoters to drive expression of the guide RNAs, e.g., the H1, U6 or 7SK promoters. These human promoters allow for expression of split deaminase fusion protein in mammalian cells following plasmid transfection.

Some expression systems have markers for selection of stably transfected cell lines such as thymidine kinase, hygromycin B phosphotransferase, and dihydrofolate reductase. High yield expression systems are also suitable, such as using a baculovirus vector in insect cells, with the gRNA encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of recombinant sequences.

Standard transfection methods are used to produce bacterial, mammalian, yeast or insect cell lines that express large quantities of protein, which are then purified using standard techniques (see, e.g., Colley et al., 1989, J. Biol. Chem., 264:17619-22; Guide to Protein Purification, in Methods in Enzymology, vol. 182 (Deutscher, ed., 1990)). Transformation of eukaryotic and prokaryotic cells are performed according to standard techniques (see, e.g., Morrison, 1977, J. Bacteriol. 132:349-351; Clark-Curtiss & Curtiss, Methods in Enzymology 101:347-362 (Wu et al., eds, 1983).

Any of the known procedures for introducing foreign nucleotide sequences into host cells may be used. These include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the split deaminase fusion protein.

Alternatively, the methods can include delivering the split deaminase fusion protein and guide RNA together, e.g., as a complex. For example, the split deaminase fusion protein and gRNA can be can be overexpressed in a host cell and purified, then complexed with the guide RNA (e.g., in a test tube) to form a ribonucleoprotein (RNP), and delivered to cells. In some embodiments, the split deaminase fusion protein can be expressed in and purified from bacteria through the use of bacterial expression plasmids. For example, His-tagged split deaminase fusion protein can be expressed in bacterial cells and then purified using nickel affinity chromatography. The use of RNPs circumvents the necessity of delivering plasmid DNAs encoding the nuclease or the guide, or encoding the nuclease as an mRNA. RNP delivery may also improve specificity, presumably because the half-life of the RNP is shorter and there's no persistent expression of the nuclease and guide (as you'd get from a plasmid). The RNPs can be delivered to the cells in vivo or in vitro, e.g., using lipid-mediated transfection or electroporation. See, e.g., Liang et al. "Rapid and highly efficient mammalian cell engineering via Cas9 protein transfection." Journal of biotechnology 208 (2015): 44-53; Zuris, John A., et al. "Cationic lipid-mediated delivery of proteins enables efficient protein-based genome editing in vitro and in vivo." Nature biotechnology 33.1 (2015): 73-80; Kim et al. "Highly efficient RNA-guided genome editing in human cells via delivery of purified Cas9 ribonucleoproteins." Genome research 24.6 (2014): 1012-1019.

The present invention also includes the vectors and cells comprising the vectors, as well as kits comprising the proteins and nucleic acids described herein, e.g., for use in a method described herein.

Treating Beta-Thalassemia

Beta-thalassemias are a group of hereditary disorders characterized by a genetic deficiency in the synthesis of beta-globin chains. Thalassemia major, in which the affected individual is homozygous for the mutation, is associated with severe anemia requiring transfusion. Thalassemia minor is the least severe and does not typically require treatment, while those with levels of severity between thalassemia minor and thalassemia major are said to have thalassemia intermedia. See, e.g., Cao and Galanello, Genetics in Medicine 12, 61-76 (2010);

The hAPOBEC3A mutants, e.g., N57G or N57A or N57Q or K60A or K60D or Y130F, as a fusion protein in the BE3 architecture as described herein can be used as a therapy in subjects, e.g., with the beta-thalassemia mutation HBB-28 (A>G) that is common in some east Asian populations (see Liang et al., Protein Cell. 2017 November; 8(11):811-822). Methods for identifying subjects with this mutation are known in the art; see, e.g., Saetung et al., Southeast Asian J Trop Med Public Health. 2013 November; 44(6):1055-64; Liu et al., Hemoglobin. 2015; 39(1):18-23; Doro et al., Hemoglobin. 2017 March; 41(2):96-99; Zhang et al., BMJ Open. 2017 Jan. 31; 7(1):e013367. The methods can include mobilizing and then extracting CD34+ hematopoietic stem and progenitor cells (HSPCs)(see, e.g., Bonig and Papayannopoulou, Methods Mol Biol. 2012; 904: 1-14; Jin, et al., BioMed Research International, vol. 2014, Article ID 435215, 9 pages, 2014). The HSPCs are then modified ex vivo (outside of the subject's body) by introducing mRNA encoding the base editor protein or by using purified base editor protein+guide (e.g., an RNP). The cells can be maintained in culture to allow for proliferation, e.g., for a few days, before infusing the modified cells back into the subject. The subject can also be myeloablated before infusion to ensure that the modified cells engraft well (see Sullivan, Keith M., et al., *New England Journal of Medicine* 378.1 (2018): 35-47.). The modified stem cells are then allowed to engraft in the subject's bone marrow and produce beta-thalassemia-free red blood cells.

As described herein, we investigated whether APO3A N57G BE3 was able to efficiently induce single nucleotide editing at the β-thalassemia causing allele HBB-28 (A>G) that is common in some east Asian populations. We first created a HEK293T model cell line bearing a singly-integrated 200 bp fragment of the disease-causing HBB-28 (A>G) promoter allele and tested whether APO3A N57G BE3 was able to more efficiently induce single nucleotide editing at the −28 (A>G) position (editing on the antisense strand, to affect the sense strand) relative to BE3 or the YE BE3 derivatives. As expected, APO3A N57G BE3 induced significantly fewer editing events at the HBB-25 bystander motif while retaining high editing activity at the −28 (A>G) cognate motif. Editing with BE3 produced 0.57% perfectly corrected alleles. Deamination of the HBB-25 cytidine in the editing window by BE3 produces the causal β-thalassemia mutations HBB-25 (G>T) and (G>C) mutations in 11.5% and 1.8% of alleles, respectively. The product −25 (G>A), present in 15.2% of total alleles after editing with BE3, may also produce an independent β-thalassemia phenotype, but this has yet to be clinically confirmed. Conversely, editing at the HBB-28 (A>G) site with APO3A N57G BE3 produced 22.5% perfectly corrected alleles, 40-fold more than BE3, and a total editing rate at the −25 position of 3.96%.

EXAMPLES

The invention is further described in the following examples, which do not limit the scope of the invention described in the claims.

Materials and Methods

Plasmids and Oligonucleotides

BE expression plasmids containing amino acid substitutions were generated by PCR and standard molecular cloning methods. gRNA expression plasmids were constructed by ligating annealed oligonucleotide duplexes into MLM3636 cut with BsmBI. All gRNAs except those targeting the HBB-28 (A>G) and CTNNB1 sites were designed to target sites containing a 5' guanine nucleotide.

Human Cell Culture and Transfection

2OS.EGFP cells containing a single stably integrated copy of the EGFP-PEST reporter gene and HEK293T cells were cultured in DMEM supplemented with 10% heat-inactivated fetal bovine serum, 2 mM GlutaMax, penicillin and streptomycin at 37° C. with 5% $CO_2$. The media for U2OS.EGFP cells was supplemented with 400 μg ml$^{-1}$ Geneticin. Cell line identity was validated by STR profiling (ATCC), and cells were tested regularly for *mycoplasma* contamination. U2OS.EGFP cells were transfected with 750 ng of plasmid expressing BE and 250 ng of plasmid expressing sgRNA according to the manufacturer's recommendations using the DN-100 program and SE cell line kit on a Lonza 4-D Nucleofector. For HEK293T transfections, 75,000 cells were seeded in 24-well plates and 18 hours later were transfected with 600 ng of plasmid expressing BE and 200 ng of plasmid expressing sgRNA using TransIT-293 (Mirus) according to the manufacturer's recommendations. For all targeted amplicon sequencing and GUIDE-seq experiments, genomic DNA was extracted 72 h post-transfection. Cells were lysed in lysis buffer containing 100 mM Tris-HCl pH 8.0, 150 mM NaCl, 5 mM EDTA, and 0.05% SDS and incubated overnight at 55 C in an incubator shaking at 250 rpm. Genomic DNA was extracted from lysed cells using carboxyl-modified Sera-Mag Magnetic Speed-beads resuspended in 2.5 M NaCl and 18% PEG-6000 (magnetic beads).

The HEK293T.HBB cell line was constructed by cloning a 200 base pair fragment of the HBB promoter upstream of an EF1a promoter driving expression of the puromycin resistance gene in a lentiviral vector. The HBB-28 (A>G) mutation was inserted by PCR and standard molecular cloning methods. The lentiviral vector was transfected into 293FS cells and media containing viral particles was harvested after 72 hours. Media containing viral particles was serially diluted and added to 10 cm plates with approximately 10 million HEK293T cells. After 48 hours, media was supplemented with 2.5 µg ml$^{-1}$ puromycin and cells were harvested from the 10 cm plate with the fewest surviving colonies to ensure single copy integration.

Off-Target Site Selection and Amplicon Design

Two of the sites characterized here, EMX1 site 1 and FANCF, were previously characterized by modified Digenome-seq, an unbiased approach to discover BE3-specific off-target sites. All off-targets discovered by modified Digenome-seq were investigated, and these sites represent the most comprehensive off-target characterization because they were discovered de novo using BE3. The VEGFA site 2 target is a promiscuous, homopolymeric gRNA that was previously characterized by GUIDE-seq. Because the VEGFA site 2 gRNA has over one hundred nuclease off-target sites, we selected the 20 off-target sites with the highest number of GUIDE-seq reads that also reside in loci for which we were able to design unique PCR amplification primers for characterization here. The CTNNB1 and HBB-28 (A>G) gRNAs had not been previously characterized with respect to BE or nuclease off-target sites. We performed GUIDE-seq as previously described" using these gRNAs to determine the SpCas9 nuclease off-target sites, and used Cas-OFFinder to predict all of the potential off-target sites with one RNA bulge and one mismatch. (GUIDE-seq and Cas-OFFinder analyses were performed using the hg38 reference genome.) This class of off-targets is more prevalent in BE3 relative to nucleases[16], and thus sites that we were unlikely to discover by GUIDE-seq. Primers were designed to amplify all off-target sites such that potential edited cytidines were within the first 100 base pairs of Illumina HTS reads. A total of six primer pairs encompassing EMX1 site 1, VEGFA site 2 and CTNNB1 site 1 off-target sites did not amplify their intended amplicon and were thus excluded from further analysis.

Statistical Testing

All statistical testing was performed using two-tailed Student's t-test according to the method of Benjamini, Krieger, and Yekutieli without assuming equal variances between samples.

Targeted Amplicon Sequencing

On- and off-target sites were amplified from ~100 ng genomic DNA from three biological replicates for each condition. PCR amplification was performed with Phusion High Fidelity DNA Polymerase (NEB). 50 µl PCR reactions were purified with 1× volume magnetic beads. Amplification fidelity was verified by capillary electrophoresis on a Qiaxcel instrument. Amplicons with orthogonal sequences were pooled for each triplicate transfection and Illumina flow cell-compatible adapters were added using the NEBNext Ultra II DNA Library Prep kit according to manufacturer instructions. Illumina i5 and i7 indices were added by an additional 10 cycles of PCR with Q5 High Fidelity DNA Polymerase using primers from NEBNext Multiplex Oligos for Illumina (Dual Index Primers Set 1) and purified using 0.7× volume magnetic beads. Final amplicon libraries containing Illumina-compatible adapters and indices were quantified by droplet digital PCR and sequenced with 150 bp paired end reads on an Illumina MiSeq instrument. Sequencing reads were de-multiplexed by MiSeq Reporter then analyzed for base frequency at each position by a modified version of CRISPResso[28]. Indels were quantified in a 10 base pair window surrounding the expected cut site for each sgRNA.

Expression of HBB-28 (A>G) gRNAs

In order to use eA3A BEs with the HF1 or Hypa mutations that decrease genome-wide off-target editing, it was necessary to use 20 nucleotides of spacer sequence in the gRNA with no mismatches between the spacer and target site. We expressed the HBB-28 (A>G) gRNA from a plasmid using the U6 promoter, which preferentially initiates transcription at a guanine nucleotide at the +1 position. To preserve perfect matching between the spacer and target site, we appended a self-cleaving 5' hammerhead ribozyme that is able to remove the mismatched guanine at the 5' of the spacer.

```
Exemplary protein sequences rAPOBEC1-XTEN L8-nCas9-UGI-SV40 NLS
MSSETGPVAVDPTLRRRIEPHEFEVFFDPRELRKETCLLYEINWGGRHSIW
RHTSQNTNKHVEVNFIEKFTTERYFCPNTRCSITWFLSWSPCGECSRAITEFLSRYP
HVTLFIYIARLYHHADPRNRQGLRDLISSGVTIQIMTEQESGYCWRNFVNYSPSNEA
HWPRYPHLVVVRLYVLELYCIILGLPPCLNILRRKQPQLTFFTIALQSCHYQRLPPHIL
WATGLKSGSETPGTSESATPESDKKYSIGLAIGTNSVGWAVITDEYKVPSKKFKVLG
NTDRHSIKKNLIGALLFDSGETAEATRLKRTARRRYTRRKNRICYLQEIFSNEMAKVD
DSFFHRLEESFLVEEDKKHERHPIFGNIVDEVAYHEKYPTIYHLRKKLVDSTDKADLR
LIYLALAHMIKFRGHFLIEGDLNPDNSDVDKLFIQLVQTYNQLFEENPINASGVDAKAI
LSARLSKSRRLENLIAQLPGEKKNGLFGNLIALSLGLTPNFKSNFDLAEDAKLQLSKD
TYDDDLDNLLAQIGDQYADLFLAAKNLSDAILLSDILRVNTEITKAPLSASMIKRYDEH
HQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKIEKIL
TFRIPYYVGPLARGNSRFAWMTRKSEETITPWNFEEVVDKGASAQSFIERMTNFDK
NLPNEKVLPKHSLLYEYFTVYNELTKVKYVTEGMRKPAFLSGEQKKAIVDLLFKTNR
KVTVKQLKEDYFKKIECFDSVEISGVEDRFNASLGTYHDLLKIIKDKDFLDNEENEDIL
EDIVLTLTLFEDREMIEERLKTYAHLFDDKVMKQLKRRRYTGWGRLSRKLINGIRDK
QSGKTILDFLKSDGFANRNFMQLIHDDSLTFKEDIQKAQVSGQGDSLHEHIANLAGS
PAIKKGILQTVKVVDELVKVMGRHKPENIVIEMARENQTTQKGQKNSRERMKRIEEG
IKELGSQILKEHPVENTQLQNEKLYLYYLQNGRDMYVDQELDINRLSDYDVDHIVPQ
SFLKDDSIDNKVLTRSDKNRGKSDNVPSEEVVKKMKNYWRQLLNAKLITQRKFDNL
TKAERGGLSELDKAGFIKRQLVETRQITKHVAQILDSRMNTKYDENDKLIREVKVITL
KSKLVSDFRKDFQFYKVREINNYHHAHDAYLNAVVGTALIKKYPKLESEFVYGDYKV
YDVRKMIAKSEQEIGKATAKYFFYSNIMNFFKTEITLANGEIRKRPLIETNGETGEIVW
DKGRDFATVRKVLSMPQVNIVKKTEVQTGGFSKESILPKRNSDKLIARKKDWDPKK
YGGFDSPTVAYSVLVVAKVEKGKSKKLKSVKELLGITIMERSSFEKNPIDFLEAKGYK
EVKKDLIIKLPKYSLFELENGRKRMLASAGELQKGNELALPSKYVNFLYLASHYEKLK
GSPEDNEQKQLFVEQHKHYLDEIIEQISEFSKRVILADANLDKVLSAYNKHRDKPIRE
QAENIIHLFTLTNLGAPAAFKYFDTTIDRKRYTSTKEVLDATLIHQSITGLYETRIDLSQ
```

| Exemplary protein sequences |
|---|
| LGGDSGGSTNLSDIIEKETGKQLVIQESILMLPEEVEEVIGNKPESDILVHTAYDESTD<br>ENVMLLTSDAPEYKPWALVIQDSNGENKIKMLSGGSPKKKRKV (SEQ ID NO: 50)<br><br>Uracil glycosylase inhibitor (UGI)<br>TNLSDIIEKETGKQLVIQESILMLPEEVEEVIGNKPESDILVHTAYDEST<br>DENVMLLTSDAPEYKPWALVIQDSNGENKIKML (SEQ ID NO: 45)<br><br>hAID<br>MDSLLMNRRKFLYQFKNVRWAKGRRETYLCYVVKRRDSATSFSLDFGYLR<br>NKNGCHVELLFLRYISDWDLDPGRCYRVTWFTSWSPCYDCARHVADFLRGNPNLS<br>LRIFTARLYFCEDRKAEPEGLRRLHRAGVQIAIMTFKDYFYCWNTFVENHERTFKAW<br>EGLHENSVRLSRQLRRILLPLYEVDDLRDAFRTLGL (SEQ ID NO: 51)<br><br>hAIDv solubility variant lacking N-terminal RNA-binding region<br>MDPHIFTSNFNNGIGRHKTYLCYEVERLDSATSFSLDFGYLRNKNGCHVELL<br>FLRYISDWDLDPGRCYRVTWFTSWSPCYDCARHVADFLRGNPNLSLRIFTARLYFC<br>EDRKAEPEGLRRLHRAGVQIAIMTFKDYFYCWNTFVENHERTFKAWEGLHENSVRL<br>SRQLRRILLPLYEVDDLRDAFRTLGL (SEQ ID NO: 52)<br><br>hAIDv solubility variant lacking N-terminal RNA-binding region and the<br>C-terminal poorly structured region<br>MDPHIFTSNFNNGIGRHKTYLCYEVERLDSATSFSLDFGYLRNKNGCHVELL<br>FLRYISDWDLDPGRCYRVTWFTSWSPCYDCARHVADFLRGNPNLSLRIFTARLYFC<br>EDRKAEPEGLRRLHRAGVQIAIMTFKDYFYCWNTFVENHERTFKAWEGLHENSVRL<br>SRQLRRILLPL (SEQ ID NO: 53)<br><br>rAPOBEC1<br>MSSETGPVAVDPTLRRRIEPHEFEVFFDPRELRKETCLLYEINWGGRHSIW<br>RHTSQNTNKHVEVNFIEKFTTERYFCPNTRCSITWFLSWSPCGECSRAITEFLSRYP<br>HVTLFIYIARLYHHADPRNRQGLRDLISSGVTIQIMTEQESGYCWRNFVNYSPSNEA<br>HWPRYPHLWVRLYVLELYCIILGLPPCLNILRRKQPQLTFFTIALQSCHYQRLPPHIL<br>WATGLK (SEQ ID NO: 54)<br><br>mAPOBEC3<br>MGPFCLGCSHRKCYSPIRNLISQETFKFHFKNLGYAKGRKDTFLCYEVTRK<br>DCDSPVSLHHGVFKNKDNIHAEICFLYWFHDKVLKVLSPREEFKITWYMSWSPCFE<br>CAEQIVRFLATHHNLSLDIFSSRLYNVQDPETQQNLCRLVQEGAQVAAMDLYEFKK<br>CWKKKFVDNGGRRFRPWKRLLTNFRYQDSKLQEILRRMDPLSEEEFYSQFYNQRVK<br>HLCYYHRMKPYLCYQLEQFNGQAPLKGCLLSEKGKQHAEILFLDKIRSMELSQVTIT<br>CYLTWSPCPNCAWQLAAFKRDRPDLILHIYTSRLYFHWKRPFQKGLCSLWQSGILV<br>DVMDLPQFTDCWTNFVNPKRPFRPWKGLEIISRRTQRRLRRIKESWGLQDLVNDF<br>GNLQLGPPMSN (SEQ ID NO: 55)<br><br>mAPOBEC3 catalytic domain<br>MGPFCLGCSHRKCYSPIRNLISQETFKFHFKNLGYAKGRKDTFLCYEVTRK<br>DCDSPVSLHHGVFKNKDNIHAEICFLYWFHDKVLKVLSPREEFKITWYMSWSPCFE<br>CAEQIVRFLATHHNLSLDIFSSRLYNVQDPETQQNLCRLVQEGAQVAAMDLYEFKK<br>CWKKKFVDNGGRRFRPWKRLLTNFRYQDSKLQEILRR (SEQ ID NO: 56)<br><br>hAPOBEC3A<br>MEASPASGPRHLMDPHIFTSNFNNGIGRHKTYLCYEVERLDNGTSVKMDQ<br>HRGFLHNQAKNLLCGFYGRHAELRFLDLVPSLQLDPAQIYRVTWFISWSPCFSWGC<br>AGEVRAFLQENTHVRLRIFAARIYDYDPLYKEALQMLRDAGAQVSIMTYDEFKHCW<br>DTFVDHQGCPFQPWDGLDEHSQALSGRLRAILQNQGN (SEQ ID NO: 57)<br><br>hAPOBEC3G<br>MKPHFRNTVERMYRDTFSYNFYNRPILSRRNTVWLCYEVKTKGPSRPPLDA<br>KIFRGQVYSELKYHPEMRFFHWFSKWRKLHRDQEYEVTWYISWSPCTKCTRDMAT<br>FLAEDPKVTLTIFVARLYYFWDPDYQEALRSLCQKRDGPRATMKIMNYDEFQHCWS<br>KFVYSQRELFEPWNNLPKYYILLHIMLGEILRHSMDPPTFTFNFNNEPWVRGRHETY<br>LCYEVERMHNDTWVLLNQRRGFLCNQAPHKHGFLEGRHAELCFLDVIPFWKLDLD<br>QDYRVTCFTSWSPCFSCAQEMAKFISKNKHVSLCIFTARIYDDQGRCQEGLRTLAE<br>AGAKISIMTYSEFKHCWDTFVDHQGCPFQPWDGLDEHSQDLSGRLRAILQNQEN<br>(SEQ ID NO: 58)<br><br>hAPOBEC3G catalytic domain<br>PPTFTFNFNNEPWVRGRHETYLCYEVERMHNDTWVLLNQRRGFLCNQAP<br>HKHGFLEGRHAELCFLDVIPFWKLDLDQDYRVTCFTSWSPCFSCAQEMAKFISKNK<br>HVSLCIFTARIYDDQGRCQEGLRTLAEAGAKISIMTYSEFKHCWDTFVDHQGCPFQ<br>PWDGLDEHSQDLSGRLRAILQNQEN (SEQ ID NO: 59)<br><br>hAPOBEC3H<br>MALLTAETFRLQFNNKRRLRRPYYPRKALLCYQLTPQNGSTPTRGYFENKK<br>KCHAEICFINEIKSMGLDETQCYQVTCYLTWSPCSSCAWELVDFIKAHDHLNLGIFA<br>SRLYYHWCKPQQKGLRLLCGSQVPVEVMGFPKFADCWENFVDHEKPLSFNPYKM<br>LEELDKNSRAIKRRLERIKIPGVRAQGRYMDILCDAEV (SEQ ID NO: 60) |

| Exemplary protein sequences |
|---|
| hAPOBEC3F<br>MKPHFRNTVERMYRDTFSYNFYNRPILSRRNTVWLCYEVKTKGPSRPRLD<br>AKIFRGQVYSQPEHHAEMCFLSWFCGNQLPAYKCFQITWFVSWTPCPDCVAKLAE<br>FLAEHPNVTLTISAARLYYYWERDYRRALCRLSQAGARVKIMDDEEFAYCWENFVY<br>SEGQPFMPWYKFDDNYAFLHRTLKEILRNPMEAMYPHIFYPHFKNLRKAYGRNES<br>WLCFTMEVVKHHSPVSWKRGVFRNQVDPETHCAERCFLSWFCDDILSPNTNYEV<br>TWYTSWSPCPECAGEVAEFLARHSNVNLTIFTARLYYFWDTDYQEGLRSLSQEGA<br>SVEIMGYKDFKYCWENFVYNDDEPFKPWKGLKYNFLFLDSKLQEILE (SEQ ID<br>NO: 61) |
| hAPOBEC3F catalytic domain<br>KEILRNPMEAMYPHIFYFHFKNLRKAYGRNESWLCFTMEVVKHHSPVSWKR<br>GVFRNQVDPETHCAERCFLSWFCDDILSPNTNYEVTWYTSWSPCPECAGEVAEF<br>LARHSNVNLTIFTARLYYFWDTDYQEGLRSLSQEGASVEIMGYKDFKYCWENFVYN<br>DDEPFKPWKGLKYNFLFLDSKLQEILE (SEQ ID NO: 62) |
| *S. aureus* Cas9<br>MKRNYILGLDIGITSVGYGIIDYETRDVIDAGVRLFKEANVENNEGRRSKRGA<br>RRLKRRRRHRIQRVKKLLFDYNLLTDHSELSGINPYEARVKGLSQKLSEEEFSAALL<br>HLAKRRGVHNVNEVEEDTGNELSTKEQISRNSKALEEKYVAELQLERLKKDGEVRG<br>SINRFKTSDYVKEAKQLLKVQKAYHQLDQSFIDTYIDLLETRRTYYEGPGEGSPFGW<br>KDIKEWYEMLMGHCTYFPEELRSVKYAYNADLYNALNDLNNLVITRDENEKLEYYE<br>KFQIIENVFKQKKKPTLKQIAKEILVNEEDIKGYRVTSTGKPEFTNLKVYHDIKDITARK<br>EIIENAELLDQIAKILTIYQSSEDIQEELTNLNSELTQEEIEQISNLKGYTGTHNLSLKAI<br>NLILDELWHTNDNQIAIFNRLKLVPKKVDLSQQKEIPTTLVDDFILSPVVKRSFIQSIKVI<br>NAIIKKYGLPNDIIIELAREKNSKDAQKMINEMQKRNRQTNERIEEIIRTTGKENAKYLI<br>EKIKLHDMQEGKCLYSLEAIPLEDLLNNPFNYEVDHIIPRSVSFDNSFNNKVLVKQEE<br>NSKKGNRTPFQYLSSSDSKISYETFKKHILNLAKGKGRISKTKKEYLLEERDINRFSV<br>QKDFINRNLVDTRYATRGLMNLLRSYFRVNNLDVKVKSINGGFTSFLRRKWKFKKE<br>RNKGYKHHAEDALIIANADFIFKEWKKLDKAKKVMENQMFEEKQAESMPEIETEQEY<br>KEIFITPHQIKHIKDFKDYKYSHRVDKKPNRELINDTLYSTRKDDKGNTLIVNNLNGLY<br>DKDNDKLKKLINKSPEKLLMYHHDPQTYQKLKLIMEQYGDEKNPLYKYYEETGNYLT<br>KYSKKDNGPVIKKIKYYGNKLNAHLDITDDYPNSRNKVVKLSLKPYRFDVYLDNGVY<br>KFVTVKNLDVIKKENYYEVNSKCYEEAKKLKKISNQAEFIASFYNNDLIKINGELYRVI<br>GVNNDLLNRIEVNMIDITYREYLENMNDKRPPRIIKTIASKTQSIKKYSTDILGNLYEVK<br>SKKHPQIIKKG (SEQ ID NO: 63) |
| *C. jejuni* Cas9<br>MARILAFDIGISSIGWAFSENDELKDCGVRIFTKVENPKTGESLALPRRLARS<br>ARKRLARRKARLNHLKHLIANEFKLNYEDYQSFDESLAKAYKGSLISPYELRFRALN<br>ELLSKQDFARVILHIAKRRGYDDIKNSDDKEKGAILKAIKQNEEKLANYQSVGEYLYK<br>EYFQKFKENSKEFTNVRNKKESYERCIAQSFLKDELKLIFKKQREFGFSFSKKFEEE<br>VLSVAFYKRALKDFSHLVGNCSFFTDEKRAPKNSPLAFMFVALTRIINLLNNLKNTEG<br>ILYTKDDLNALLNEVLKNGTLTYKQTKKLLGLSDDYEFKGEKGTYFIEFKKYKEFIKAL<br>GEHNLSQDDLNEIAKDITLIKDEIKLKKALAKYDLNQNQIDSLSKLEFKDHLNISFKALK<br>LVTPLMLEGKKYDEACNELNLKVAINEDKKDFLPAFNETYYKDEVTNPVVLRAIKEY<br>RKVLNALLKKYGKVHKINIELAREVGKNHSQRAKIEKEQNENYKAKKDAELECEKLG<br>LKINSKNILKLRLFKEQKEFCAYSGEKIKISDLQDEKMLEIDHIYPYSRSFDDSYMNKV<br>LVFTKQNQEKLNQTPFEAFGNDSAKWQKIEVLAKNLPTKKQKRILDKNYKDKEQKN<br>FKDRNLNDTRYIARLVLNYTKDYLDFLPLSDDENTKLNDTQKGSKVHVEAKSGMLTS<br>ALRHTWGFSAKDRNNHLHHAIDAVIIAYANNSIVKAFSDFKKEQESNSAELYAKKISE<br>LDYKNKRKFFEPFSGFRQKVLDKIDEIFVSKPERKKPSGALHEETFRKEEEFYQSYG<br>GKEGVLKALELGKIRKVNGKIVKNGDMFRVDIFKHKKTNKFYAVPIYTMDFALKVLPN<br>KAVARSKKGEIKDWILMDENYEFCFSLYKDSLILIQTKDMQEPEFVYYNAFTSSTVSL<br>IVSKHDNKFETLSKNQKILFKNANEKEVIAKSIGIQNLKVFEKYIVSALGEVTKAEFRQ<br>REDFKK (SEQ ID NO: 64) |
| *P. lavamentivorans* Cas9<br>MERIFGFDIGTTSIGFSVIDYSSTQSAGNIQRLGVRIFPEARDPDGTPLNQQR<br>RQKRMMRRQLRRRRIRRKALNETLHEAGFLPAYGSADWPVVMADEPYELRRRGL<br>EEGLSAYEFGRAIYHLAQHRHFKGRELEESDTPDPDVDDEKEAANERAATLKALKN<br>EQTTLGAWLARRPPSDRKRGIHAHRNVVAEEFERLWEVQSKFHPALKSEEMRARI<br>SDTIFAQRPVFWRKNTLGECRFMPGEPLCPKGSWLSQQRRMLEKLNNLAIAGGNA<br>RPLDAEERDAILSKLQQQASMSWPGVRSALKALYKQRGEPGAEKSLKFNLELGGE<br>SKLLGNALEAKLADMFGPDWPAHPRKQEIRHAVHERLWAADYGETPDKKRVIILSE<br>KDRKAHREAAANSFVADFGITGEQAAQLQALKLPTGWEPYSIPALNLFLAELEKGER<br>FGALVNGPDWEGWRRTNFPHRNQPTGEILDKLPSPASKEERERISQLRNPTVVRT<br>QNELRKVVNNLIGLYGKPDRIRIEVGRDVGKSKREREEIQSGIRRNEKQRKKATEDLI<br>KNGIANPSRDDVEKVVILWKEGQERCPYTGDQIGFNALFREGRYEVEHIWPRSRSF<br>DNSPRNKTLCRKDVNIEKGNRMPFEAFGHDEDRWSAIQIRLQGMVSAKGGTGMSP<br>GKVKRFLAKTMPEDFAARQLNDTRYAAKQILAQLKRLWPDMGPEAPVKVEAVTGQ<br>VTAQLRKLVVTLNNILADDGEKTRADHRHHAIDALTVACTHPGMTNKLSRYQQLRDD<br>PRAEKPALTPPWDTIRADAEKAVSEIVVSHRVRKKVSGPLHKETTYGDTGTDIKTKS<br>GTYRQFVTRKKIESLSKGELDEIRDPRIKEIVAAHVAGRGGDPKKAFPPYPCVSPGG<br>PEIRKVRLTSKQQLNLMAQTGNGYADLGSNHHIAIYRLPDGKADFEIVSLFDASRRL<br>AQRNPIVQRTRADGASFVMSLAAGEAIMIPEGSKKGIWIVQGVVVASGQVVLERDTD<br>ADHSTTTRPMPNPILKDDAKKVSIDPIGRVRPSND (SEQ ID NO: 65) |

Exemplary protein sequences

*N. cinerea* Cas9
MAAFKPNPMNYILGLDIGIASVGWAIVEIDEEENPIRLIDLGVRVFERAEVPKT
GDSLAAARRLARSVRRLTRRRAHRLLRARRLLKREGVLQAADFDENGLIKSLPNTP
WQLRAAALDRKLTPLEWSAVLLHLIKHRGYLSQRKNEGETADKELGALLKGVADNT
HALQTGDFRTPAELALNKFEKESGHIRNQRGDYSHTFNRKDLQAELNLLFEKQKEF
GNPHVSDGLKEGIETLLMTQRPALSGDAVQKMLGHCTFEPTEPKAAKNTYTAERFV
WLTKLNNLRILEQGSERPLTDTERATLMDEPYRKSKLTYAQARKLLDLDDTAFFKGL
RYGKDNAEASTLMEMKAYHAISRALEKEGLKDKKSPLNLSPELQDEIGTAFSLFKTD
EDITGRLKDRVQPEILEALLKHISFDKFVQISLKALRRIVPLMEQGNRYDEACTEIYGD
HYGKKNTEEKIYLPPIPADEIRNPVVLRALSQARKVINGVVRRYGSPARIHIETAREV
GKSFKDRKEIEKRQEENRKDREKSAAKFREYFPNFVGEPKSKDILKLRLYEQQHGK
CLYSGKEINLGRLNEKGYVEIDHALPFSRTWDDSFNNKVLALGSENQNKGNQTPYE
YFNGKDNSREWQEFKARVETSRFPRSKKQRILLQKFDEDGFKERNLNDTRYINRFL
CQFVADHMLLTGKGKRRVFASNGQITNLLRGFWGLRKVRAENDRHHALDAVVVAC
STIAMQQKITRFVRYKEMNAFDGKTIDKETGEVLHQKAHFPQPWEFFAQEVMIRVF
GKPDGKPEFEEADTPEKLRTLLAEKLSSRPEAVHKYVTPLFISRAPNRKMSGQGHM
ETVKSAKRLDEGISVLRVPLTQLKLKDLEKMVNREREPKLYEALKARLEAHKDDPAK
AFAEPFYKYDKAGNRTQQVKAVRVEQVQKTGVWVHNHNGIADNATIVRVDVFEKG
GKYYLVPIYSWQVAKGILPDRAVVQGKDEEDWTVMDDSFEFKFVLYANDLIKLTAKK
NEFLGYFVSLNRATGAIDIRTHDTDSTKGKNGIFQSVGVKTALSFQKYQIDELGKEIR
PCRLKKRPPVR (SEQ ID NO: 66)

*C. lari* Cas9
MRILGFDIGINSIGWAFVENDELKDCGVRIFTKAENPKNKESLALPRRNARSS
RRRLKRRKARLIAIKRILAKELKLNYKDYVAADGELPKAYEGSLASVYELRYKALTQN
LETKDLARVILHIAKHRGYMNKNEKKSNDAKKGKILSALKNNALKLENYQSVGEYFY
KEFFQKYKKNTKNFIKIRNTKDNYNNCVLSSDLEKELKLILEKQKEFGYNYSEDFINEI
LKVAFFQRPLKDFSHLVGACTFFEEEKRACKNSYSAWEFVALTKIINEIKSLEKISGEI
VPTQTINEVLNLILDKGSITYKKFRSCINLHESISFKSLKYDKENAENAKLIDFRKLVEF
KKALGVHSLSRQELDQISTHITLIKDNVKLKTVLEKYNLSNEQINNLLEIEFNDYINLSF
KALGMILPLMREGKRYDEACEIANLKPKTVDEKKDFLPAFCDSIFAHELSNPVVNRAI
SEYRKVLNALLKKYGKVHKIHLELARDVGLSKKAREKIEKEQKENQAVNAWALKECE
NIGLKASAKNILKLKLWKEQKEICIYSGNKISIEHLKDEKALEVDHIYPYSRSFDDSFIN
KVLVFTKENQEKLNKTPFEAFGKNIEKVVSKIQTLAQNLPYKKKNKILDENFKDKQQE
DFISRNLNDTRYIATLIAKYTKEYLNFLLLSENENANLKSGEKGSKIHVQTISGMLTSV
LRHTWGFDKKDRNNHLHHALDAIIVAYSTNSIIKAFSDFRKNQELLKARFYAKELTSD
NYKHQVKFFEPFKSFREKILSKIDEIFVSKPPRKRARRALHKDTFHSENKIIDKCSYNS
KEGLQIALSCGRVRKIGTKYVENDTIVRVDIFKKQNKFYAIPIYAMDFALGILPNKIVIT
GKDKNNNPKQWQTIDESYEFCFSLYKNDLILLQKKNMQEPEFAYYNDFSISTSSICV
EKHDNKFENLTSNQKLLFSNAKEGSVKVESLGIQNLKVFEKYIITPLGDKIKADFQPR
ENISLKTSKKYGLR (SEQ ID NO: 67)

Example 1. Improving the Genome-Wide Specificities of Targeted Base Editing Technologies Wild type cytidine deaminase domains have intrinsic substrate sequence specificity for 2-3 nucleotide motifs (see Table 1). APOBEC enzymes recognize their cognate sequence motifs through direct contacts formed between residues in two recognition loops with variable sequence composition termed recognition loop 1 (RL1) and Loop 7[12-3, 17-22] (see Table 2, FIGS. 2A-2B, and FIGS. 3A-3B). For instance, the primary determinant of APO3A substrate sequence specificity is residue D131 in loop 7, which makes two hydrogen bonds with the thymine in the 5' TC motif. To modify the specificity of APO3A we altered the identity of the residue at position 131 to residues that have previously been demonstrated to form base-specific contacts (Table 7)[43].

To alter the specificities of all other APOBEC deaminases listed in Table 1, we altered homologous residues from each of these proteins identified by sequence alignment to APO3A.

Although wild type APO3A possesses intrinsic sequence specificity for the 5' TcR motif, it is able to deaminate 5' AcR, 5' GcR and 5' CcR motifs (wherein the lowercase C is the base that is deaminated) with lower efficiencies. This suggests that it might be possible to engineer APO3A to have greater specificity for its canonical TcR substrate motif by removing excess binding energy in the form of contacts made between APO3A and its substrate ssDNA such that only TcG or TcA motifs are efficiently deaminated. Based on the crystal structure of APO3A bound to substrate ssDNA[21], we identified R28 and K30 (which seem to contact the base immediately 3' of the TCR in a semi-specific manner) as well as N57, R60, and Y130 (which all contact the ssDNA substrate backbone in non-base-specific manners) as candidate residues whose DNA contacts might contribute significant non-specific substrate binding energy such that altering them may result in a more specific deaminase. We have also identified W98 as a residue that contributes to the formation of the hydrophobic pocket that the target cytosine base is buried in and hypothesized that W98Y would decrease the hydrophobicity of this pocket while retaining deaminase activity, thereby decreasing any possible excess binding energy above that which is required for deamination of the Tc motif. Because multiple APOBEC homologs and orthologs bear significant similarity to APO3A at the sequence level, we have also identified the cognate residues expected to increase substrate sequence specificity for each of these proteins.

Figure 4:
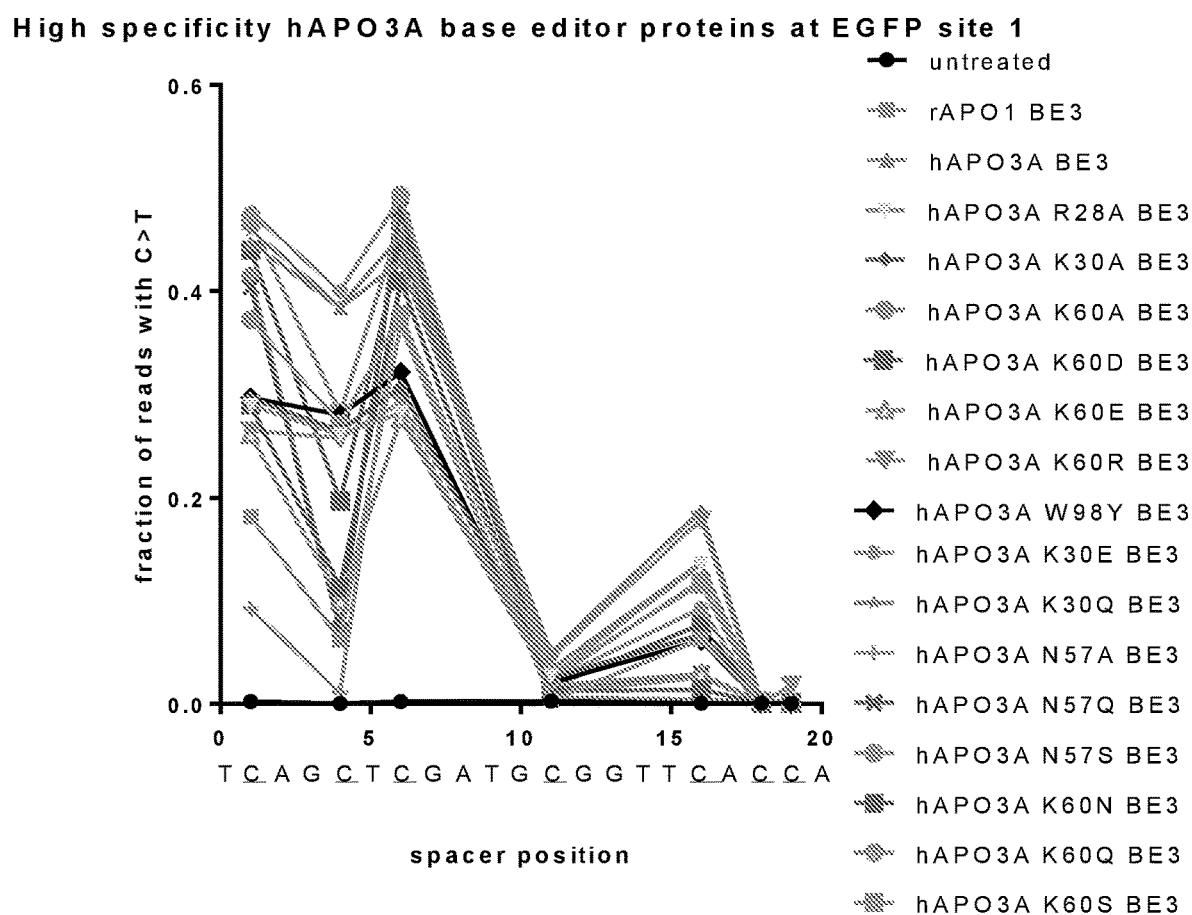
FIG. 4. APO3A-nCas9-UGI proteins were overexpressed in U2OS cells with a guide RNA targeting a site within a genomically integrated enhanced green fluorescent protein (EGFP) gene (SEQ ID NO:19). After 72 hours, genomic DNA was extracted from these cells and subjected to Illumina sequencing. The frequency of C>T transitions for each cytosine nucleotide within the spacer was plotted for each of the 15 APO3A variants bearing single residue substitutions.
Figure 5:
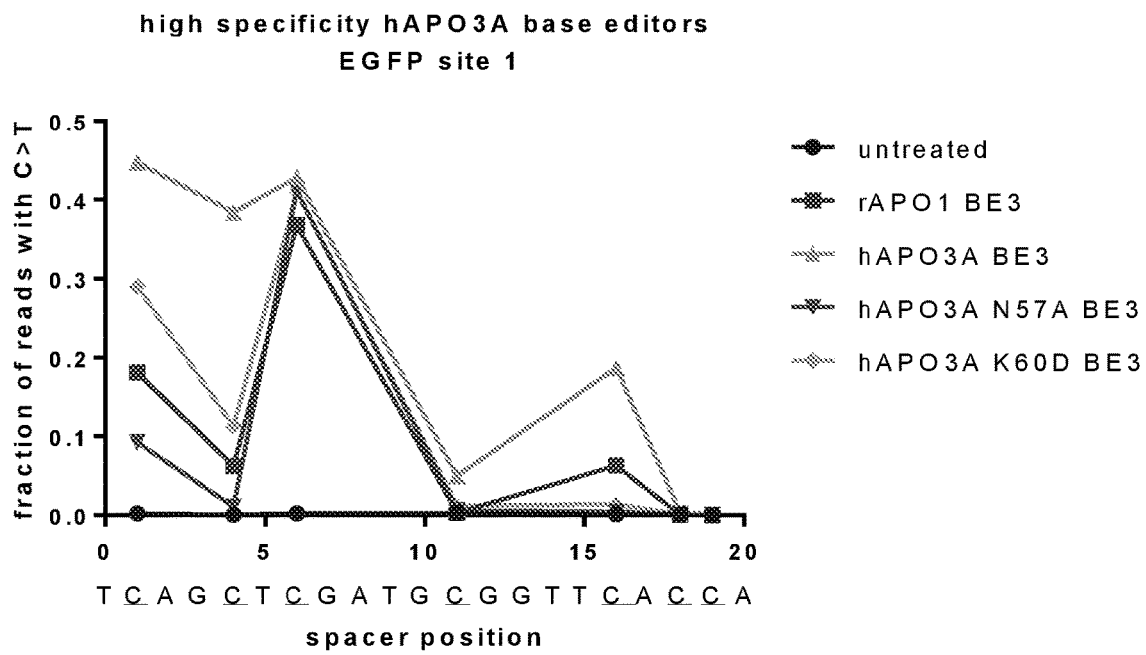
FIG. 5. APO3A-nCas9-UGI proteins were overexpressed in U2OS cells with a guide RNA targeting a site within a genomically integrated EGFP gene (SEQ ID NO: 19). After 72 hours, genomic DNA was extracted from these cells and subjected to Illumina sequencing. The frequency of C>T transitions for each cytosine nucleotide within the spacer was plotted for the APO3A-nCas9-UGI proteins bearing single residue substitutions at N57 or K60. Each of these proteins deaminated the off-target GCT motif within the editing window with decreased efficiency relative to the wild type base editor protein but retained efficient deamination activity at the on-target TCG motif within the editing window.
Figure 6:
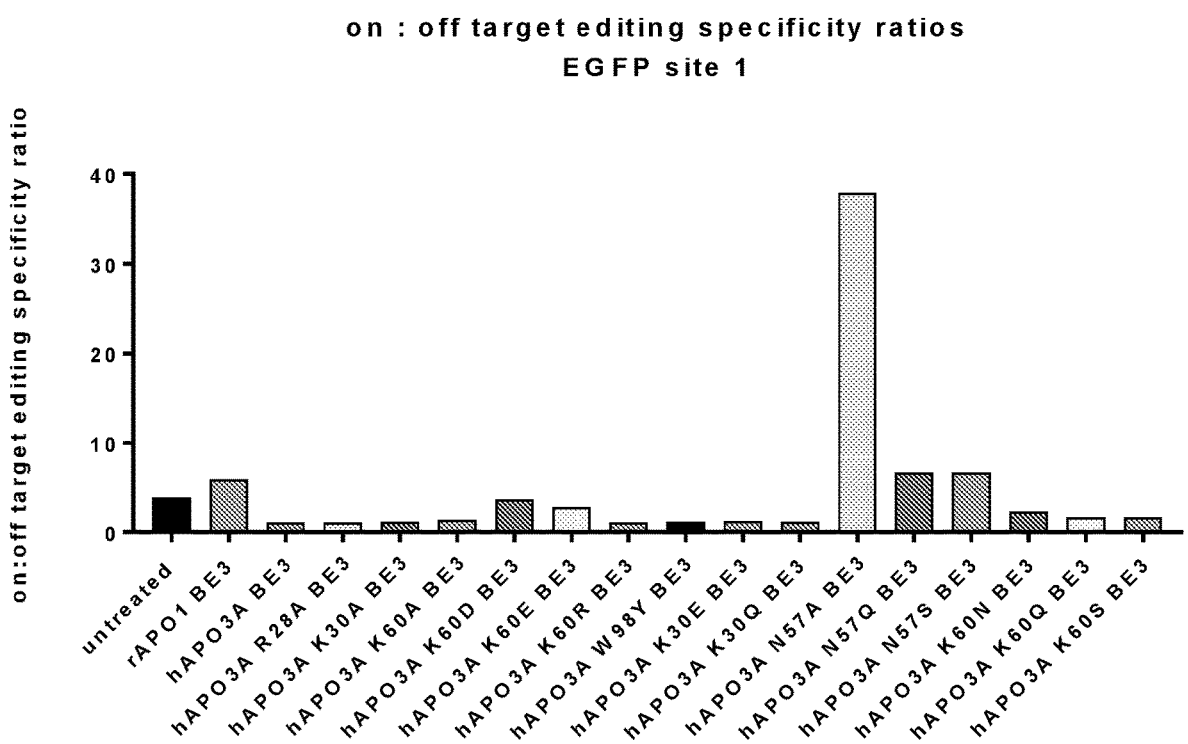
FIG. 6. The ratio of cytosine-to-thymine editing efficiencies for the on-target TCG and the off-target GCT motifs (both in the editing window) at EGFP site 1 are plotted for each of the APO3A-nCas9-UGI proteins bearing single residue substitutions. The proteins bearing N57 or K60 substitutions have increased specificity ratios relative to the wild-type APO3A base editor protein.
Figure 7:
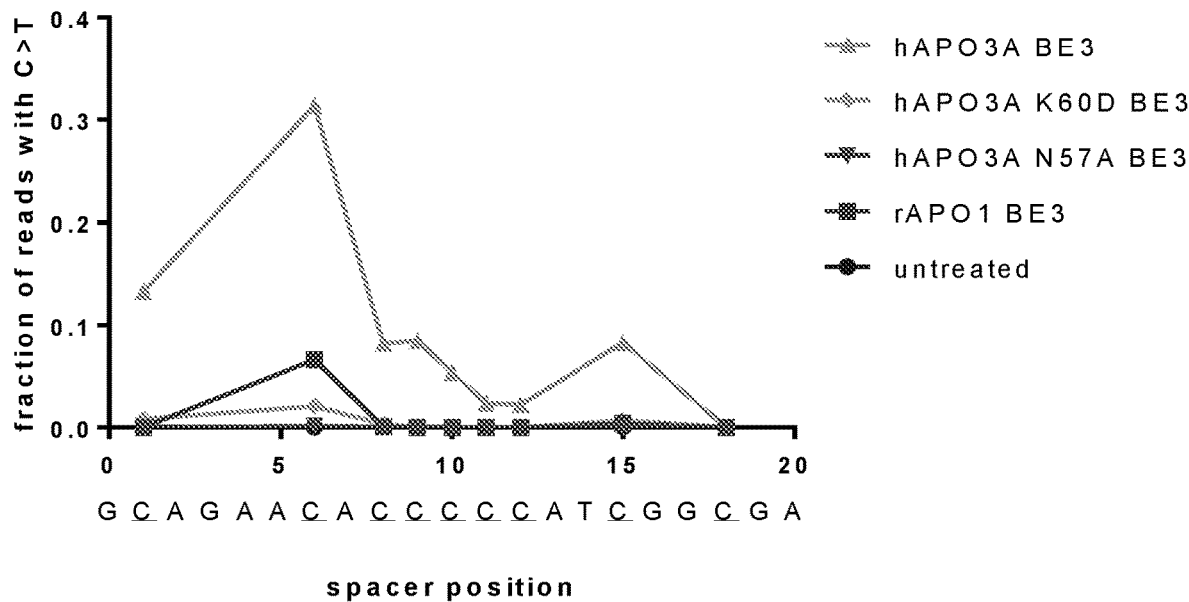
FIG. 7. APO3A-nCas9-UGI proteins were overexpressed in U2OS cells with a guide RNA targeting a site within a genomically integrated EGFP gene (SEQ ID NO:20). After 72 hours, genomic DNA was extracted from these cells and subjected to Illumina sequencing. The frequency of C>T transitions for each cytosine nucleotide within the spacer was plotted for each base editor protein.
Figure 8:
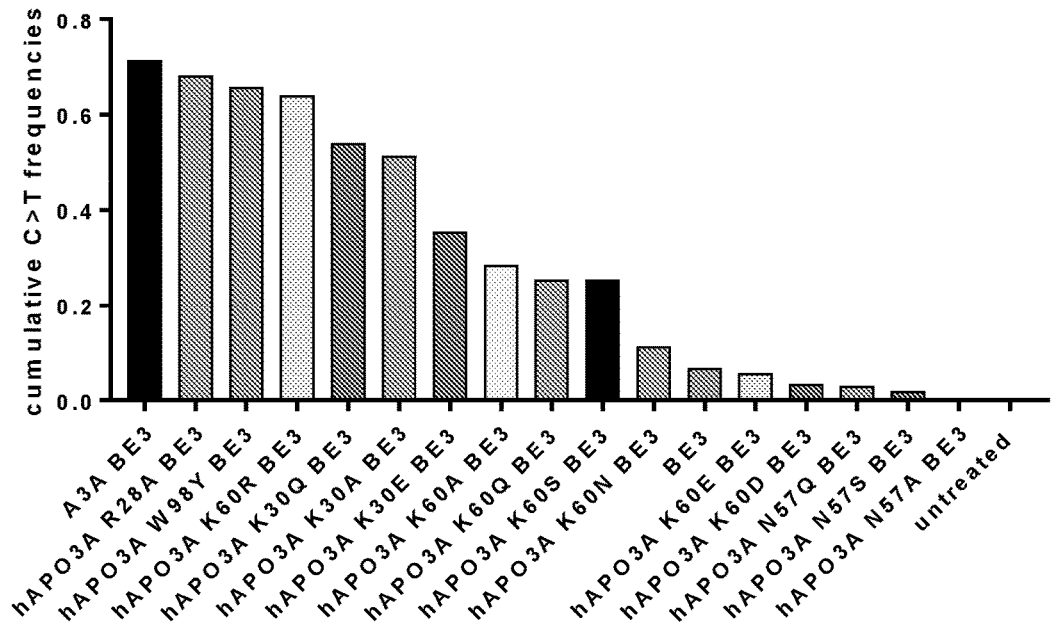
FIG. 8. Cumulative cytosine-to-thymine transition frequencies for all cytosines (all of which reside in off-target trinucleotide motifs) within the editing window of the EGFP site 2 target are plotted for each base editor protein. APO3A base editor proteins bearing single residue substitutions at N57 and K60 have significantly decreased ability to deaminase the off-target cytosines present in the editing window of this target site. Notably, APO3A N57A did not show any deaminase activity at this site.

To validate the mutations we hypothesized as able to contribute to engineered base editing proteins with increased specificity for TcR motifs, we cloned genes encoding APO3A-nCas9-UGI proteins bearing single residue substitutions in APO3A into plasmid vectors for protein overexpression in mammalian cells. We then transfected these plasmid vectors into human U2OS cells in combination with a plasmid designed to express a guide RNA targeting one of two discrete sites bearing multiple trinucleotide motifs capable of acting as deamination substrates within a single integrated EGFP gene. After 72 hours, we harvested the genomic DNA from the transfected U2OS populations and performed high-throughput amplicon sequencing at the guide RNA genomic target sites. We found that when the wild-type APO3A protein was fused to nCas9-UGI, the resulting protein was able to effect C>T transitions at the target site at the expected TcR motifs, but also on the GcT and GcG motifs present at the target site (FIG. 4). However, when N57 or K60 were mutated to residues listed in Table 7 we observed robust deamination at the on-target TcG present in the editing window, but significantly decreased ability of these proteins to target motifs outside of the base editing window and at the GcT motif present in the editing window. Notably, APO3A N57A-nCas9-UGI and APO3A K60D-nCas9-UGI retained robust activity on the editing window TcG but low to very low activity on the editing window GcT motif (FIG. 5). To quantitatively evaluate this increase in preference for TcG over GcT in the editing window of EGFP site 1, we divided the deamination frequency at the TcG motif in the editing window by the deamination frequency of the GcT motif in the editing window to determine the specificity ratio for these proteins (FIG. 6). We found that APO3A N57A-nCas9-UGI and APO3A K60D/E/N-nCas9-UGI both had demonstrated increased specificity for the TcG motif over the GcT motif relative to the wild-type APO3A-nCas9-UGI protein. We then evaluated the activity of these proteins on EGFP site 2, a target site bearing GcA, AcA, AcC, CcC, CcA and GcG motifs as well as a TcG motif outside of the editing window. Each of the previously described mutants demonstrated significantly decreased activity on each of these off target motifs in the target site, as well as decreased activity on the on-target TCG motif found outside of the editing window (FIG. 7, FIG. 8).

Based on the crystal structure of APO3A in complex with its ssDNA substrate[21], we determined that K30 makes a base-specific contact to the third nucleotide in the TcG motif. We hypothesized that mutations made to the residue at this position will alter the identity of the third nucleotide recognized by APO3A-nCas9-UGI in a trinucleotide substrate motif. Because we expect the identity of the residue at position 30 to significantly influence the identity of the third nucleotide in a substrate motif, we have determined the residues we expect to make contacts to specific bases in Table 9.

Figure 9:
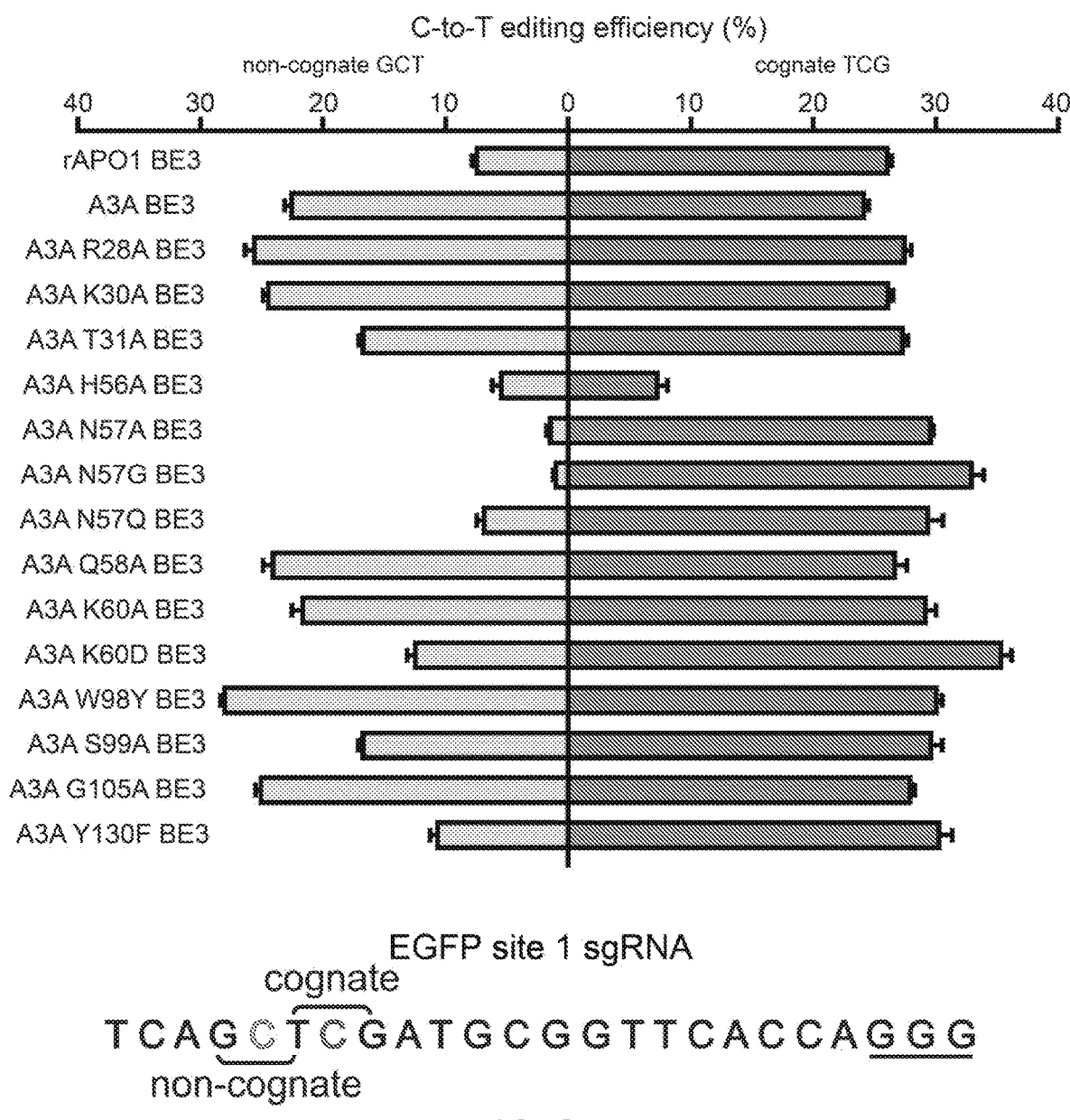
FIG. 9. U2OS cells bearing a stably integrated EGFP gene were transfected with plasmids expressing a guide targeting EGFP (the guide comprises TCAGCTCGATGCGGTT-CACCAGGG, SEQ ID NO:22) and the indicated base editor protein. After 72 hours, genomic DNA was extracted from the cells, the target site was amplified by PCR, and the PCR products were subjected to high throughput Illumina sequencing. The frequency of C-to-T transitions at the cognate and non-cognate motifs were plotted for each of the transfection conditions. Mutations made to hAPOBEC3A (APO3A) N57 were very effective in restoring sequence specificity of the deaminase domain in the base editor architecture.
Figure 10:
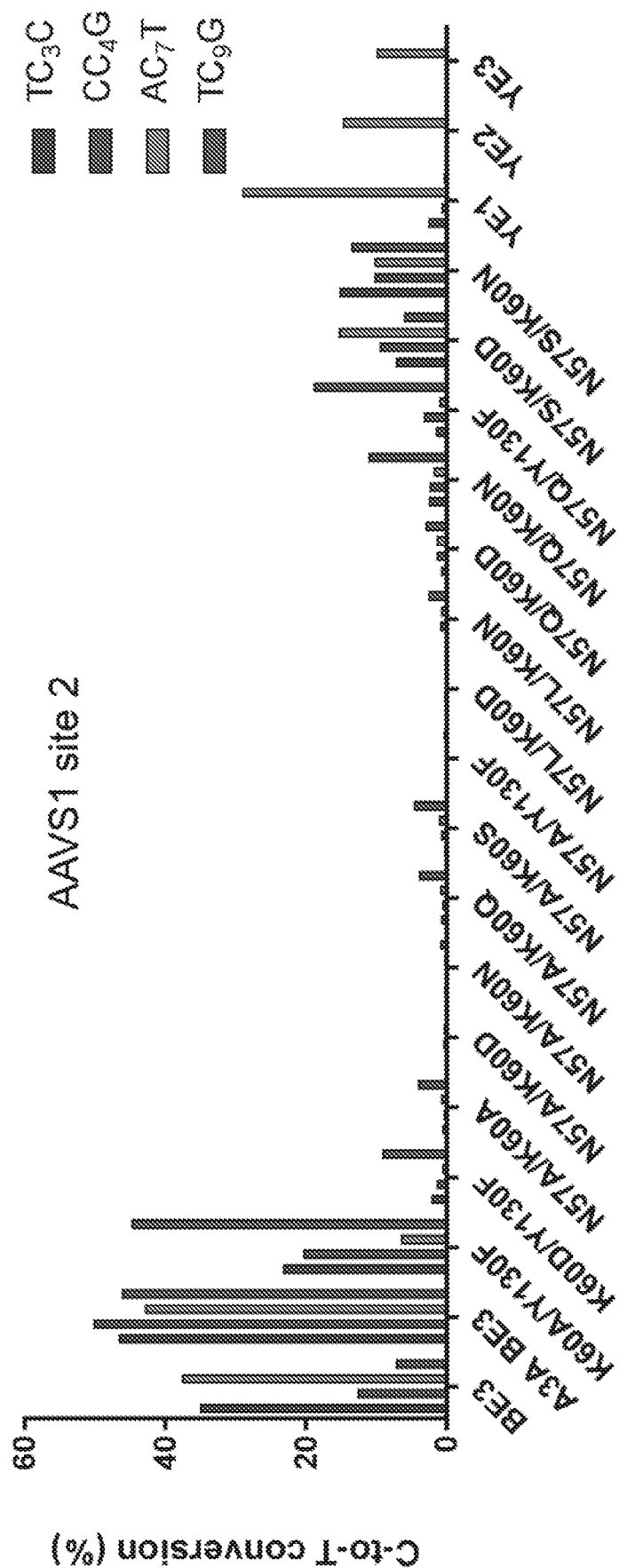
FIG. 10. HEK293T cells were transiently transfected with plasmids expressing the indicated gRNA and base editor protein. APO3A BE3 proteins bearing two substitutions generally lost significant activity at the cognate motifs in both gRNAs tested. However, the APO3A N57Q/Y130F Base Editor 3 (BE3) double mutant retained activity on the cognate motifs of both gRNAs while significantly decreasing the frequency of deamination at the non-cognate motifs.

Mutations made to various residues in APO3A (Table 9) were able to restore sequence preference to varying degrees when the resulting plasmid DNAs encoding base editor proteins were delivered by transient transfection to human cells along with a plasmid encoding a gRNA targeting a chromosomally-integrated EGFP gene (FIG. 9). We also found that we could enhance the specificity of APO3A for its cognate 5'TC motif by combining mutations to positions listed in Table 7 and targeting the BE proteins to the same EGFP target site by transient transfection of plasmid, resulting in the APO3A N57Q/Y130F BE3 variant (FIG. 10) which had similar motif specificity to APO3A N57A or N57G BE3.

Figure 11:
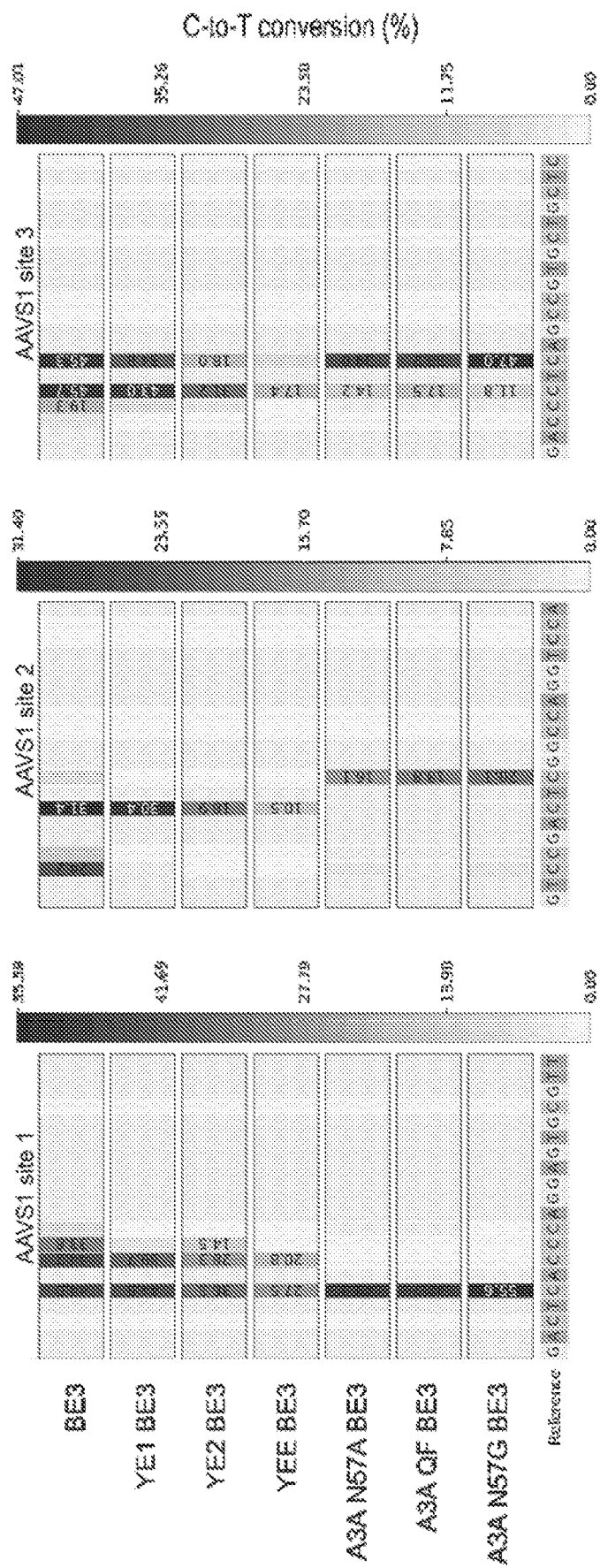
FIG. 11. HEK293T cells were transiently transfected with plasmids expressing the indicated gRNA and base editor protein. After 72 hours, genomic DNA was extracted, the target site was amplified by PCR, and the PCR products were subjected to high throughput Illumina sequencing. The frequencies of C-to-T transitions for all cytidines within the 20 nucleotide spacer sequence are plotted in heat map format. All three APO3A BE3 proteins were able to strongly bias deamination towards the cognate motif compared to BE3 and the engineered variants YE1, YE2, and YEE BE3 (YE BE3s), which decrease the frequency of such bystander mutations by incorporating point mutations into the rat APOBEC1 (rAPO1) deaminase domain that slow its kinetic rate and limit the length of its editing window compared to BE3[44]. Reference sequences, SEQ ID NOs:23-28.
Figure 12:
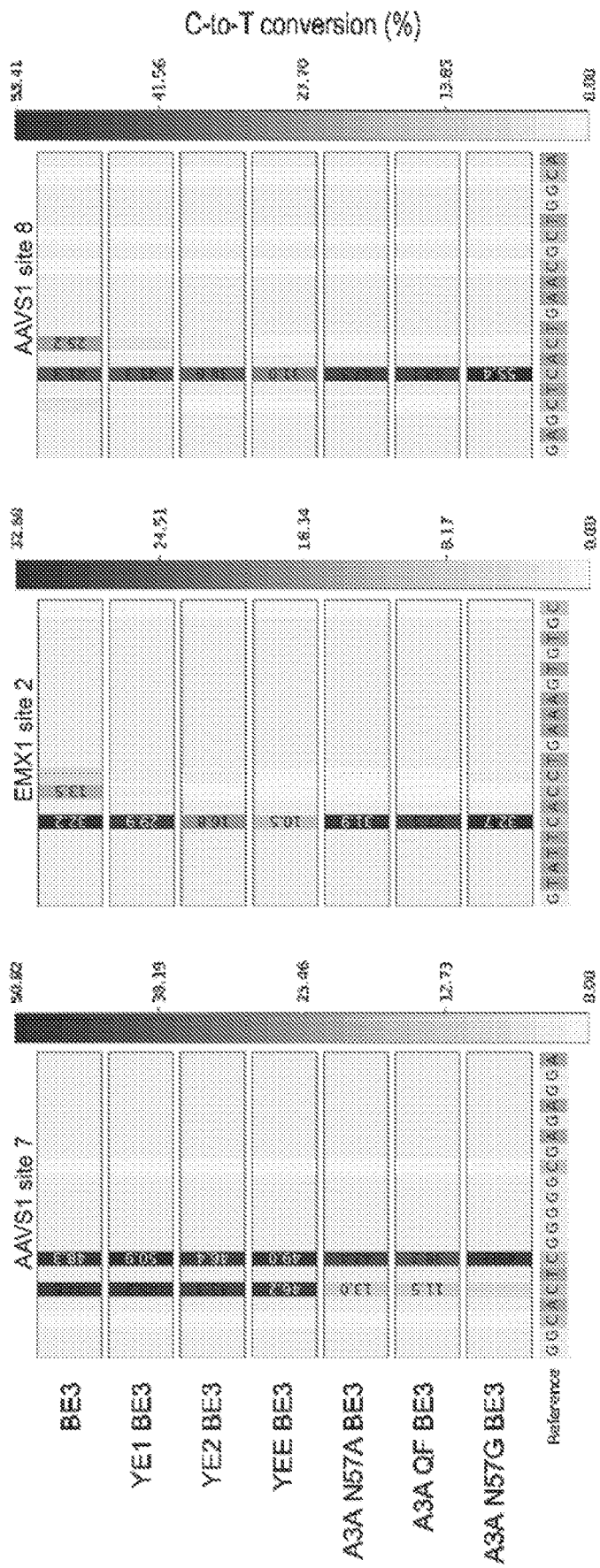
FIG. 12. HEK293T cells were transiently transfected with plasmids expressing the indicated gRNA and base editor protein. After 72 hours, genomic DNA was extracted, the target site was amplified by PCR, and the PCR products were subjected to high throughput Illumina sequencing. The frequencies of C-to-T transitions for all cytidines within the 20 nucleotide spacer sequence are plotted in heat map format. All three APO3A BE3 proteins were able to strongly bias deamination towards the cognate motif compared to BE3 and the YE BE3 proteins. Reference sequences, SEQ ID NOs:29-34.

We screened the activities of APO3A N57A or N57G or (N57Q/Y130F) BE3 at 12 endogenous genomic sites that contained a cognate 5'TC motif in the editing window in addition to another, non-cognate 5'VC (where V=A, C, or G) and compared them to BE3 and the state-of-the-art engineered variants YE1, YE2, and YEE BE3 (YE BE3 s), which decrease the frequency of such bystander mutations by incorporating point mutations into the rat APOBEC1 (rAPO1) deaminase domain that slow its kinetic rate and limit the length of its editing window compared to BE3[44]. We found that at 8 of the 12 sites, the engineered APO3A BE3 variants induced C-to-T editing at cognate motifs 5- to 264-fold more than at the non-cognate 5'VC motifs (FIGS. 11-12). However, the engineered APO3A BE3 variants induced cognate:non-cognate editing at ratios less than 5 at the remaining 4 sites.

Figure 13:
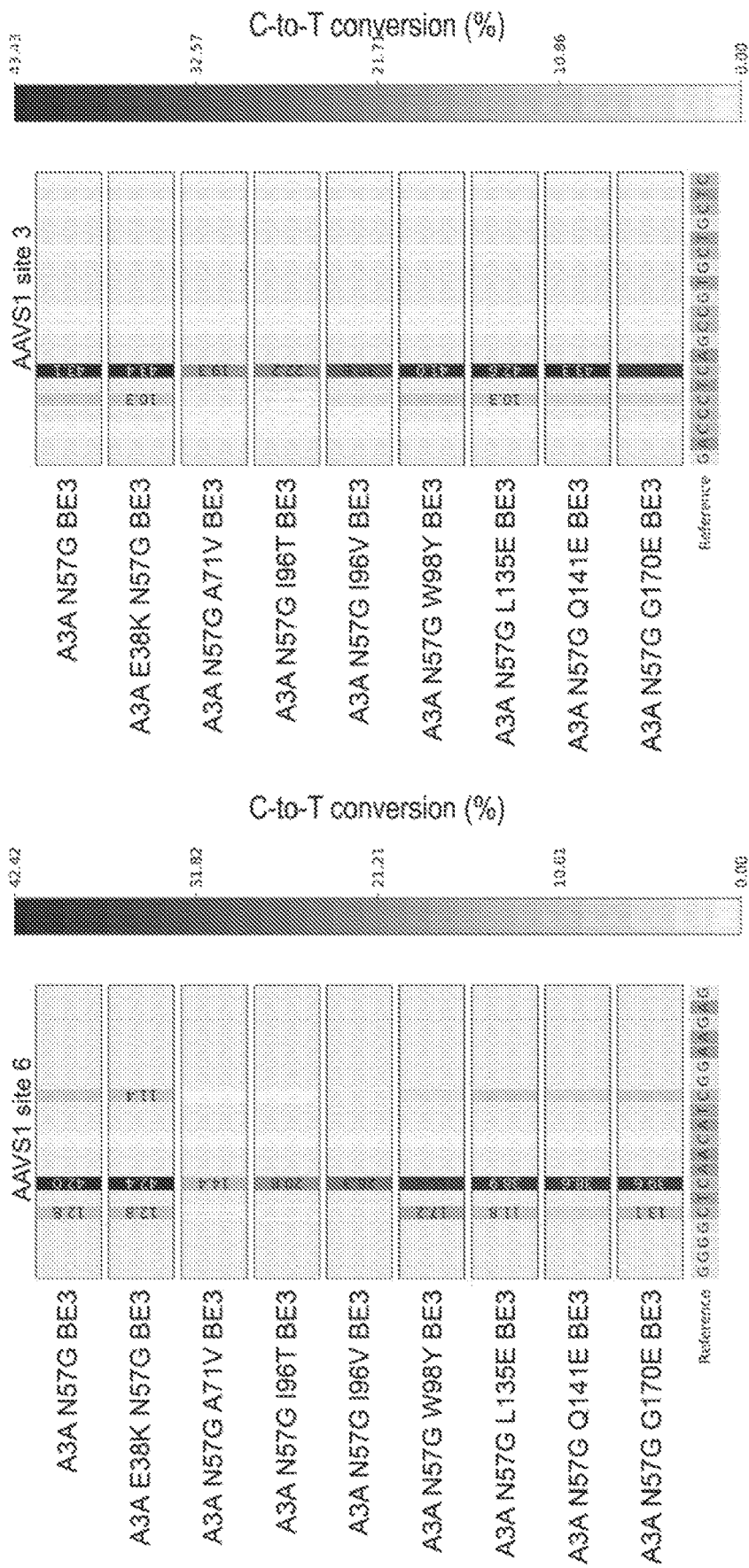
FIG. 13. HEK293T cells were transiently transfected with plasmids expressing the indicated gRNA and base editor protein. Samples were processed as outlined before. APO3A BE3 proteins bearing mutations to A71 or 196 in addition to N57G greatly decreased deamination frequencies at non-cognate motifs. The ratios of cognate to non-cognate editing for each site were plotted for all three sites for each of the variant base editor proteins, demonstrating that APO3A N57G 196T BE3 achieved cognate:non-cognate editing ratios of approximately 13 for each of the three sites tested. Reference sequences, SEQ ID NOs:35-37.

We next sought to improve sequence-specific deamination at these sites by adding mutations to APO3A N57G BE3 at residues previously shown to influence the catalytic rate and processivity of homologous proteins (Table 10). Although the addition of the individual homologous mutations derived from the YE BE3 proteins did not significantly increase sequence specificity of the APO3A N57G double mutants, mutations made to residues A71 and I96 greatly increased the cognate:non-cognate editing ratios for the three tested sites from less than 5 to approximately 13 (FIG. 13).

Critically, the exact nature of these mutations may differ in a manner dependent on delivery modality. For instance, delivery of these reagents by ribonucleoprotein (RNP) or encoded in mRNA may result in shorter duration of the proteins in cells. Shorter duration of base editor proteins in cells can result in different mutational spectra compared to longer-lived delivery, e.g. by plasmid transfection[45]. As a result, it may be necessary to use engineered cytidine deaminase BEs that retain sub-optimal sequence specificity when delivered by plasmid but optimal sequence specificity when delivered by shorter-lived modalities, for instance APO3A N57Q or K60D or Y130F BE3.

Figure 14:
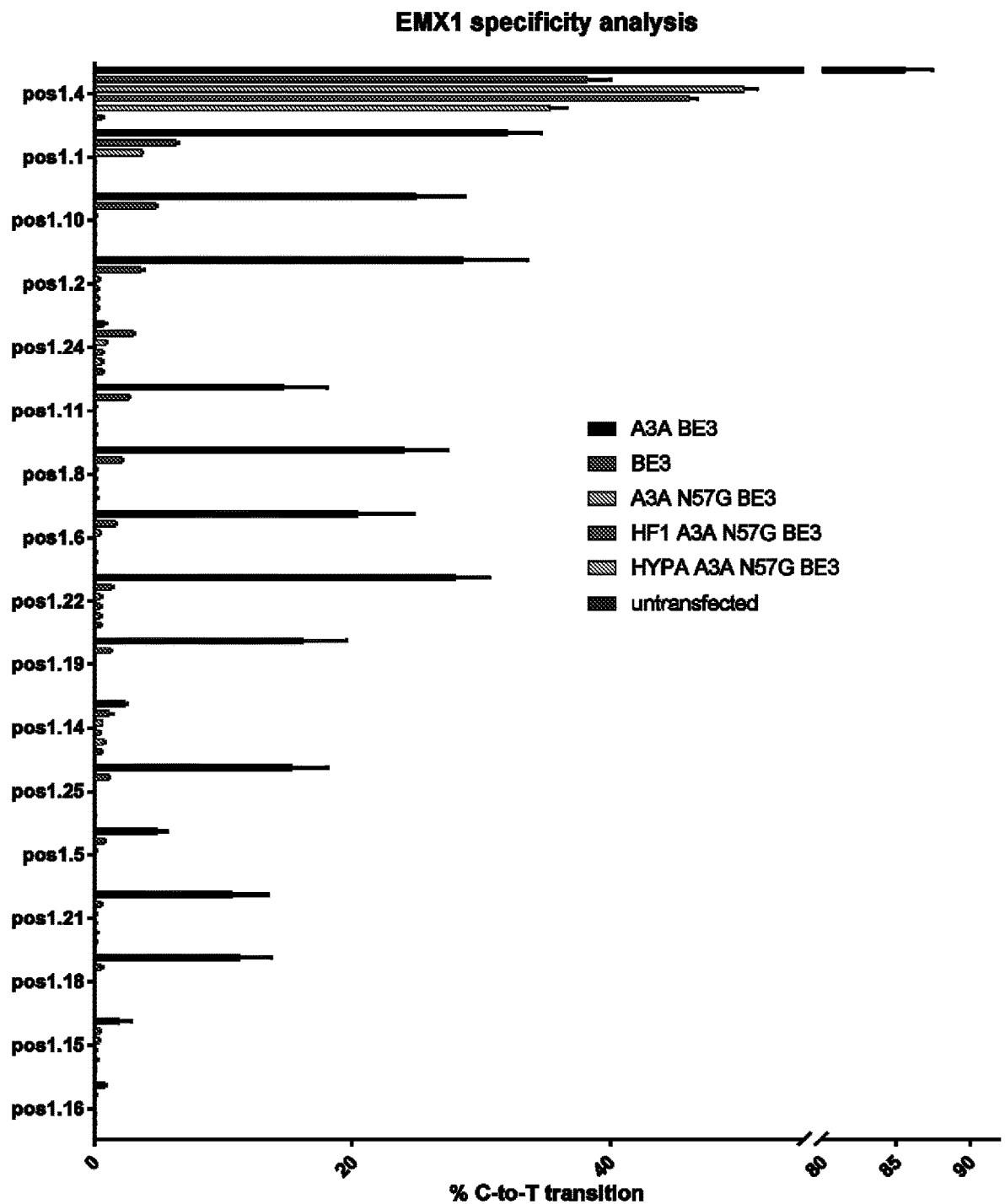
FIG. 14. HEK293T cells were transiently transfected with plasmids expressing the indicated gRNA and base editor protein. Samples were processed as outlined before. To obtain the deamination frequencies plotted, all C-to-T transition frequencies for the cytidines falling within the editing window were summed. APO3A BE3 induced very high levels of deamination at 16 of 25 off target sites. BE3 induced deamination at the same off target sites as APO3A BE3, but at lower frequencies. APO3A N57G BE3 induced indels at only 6 of 25 sites, and at much lower frequencies than BE3 at those 6 sites.
Figure 15:
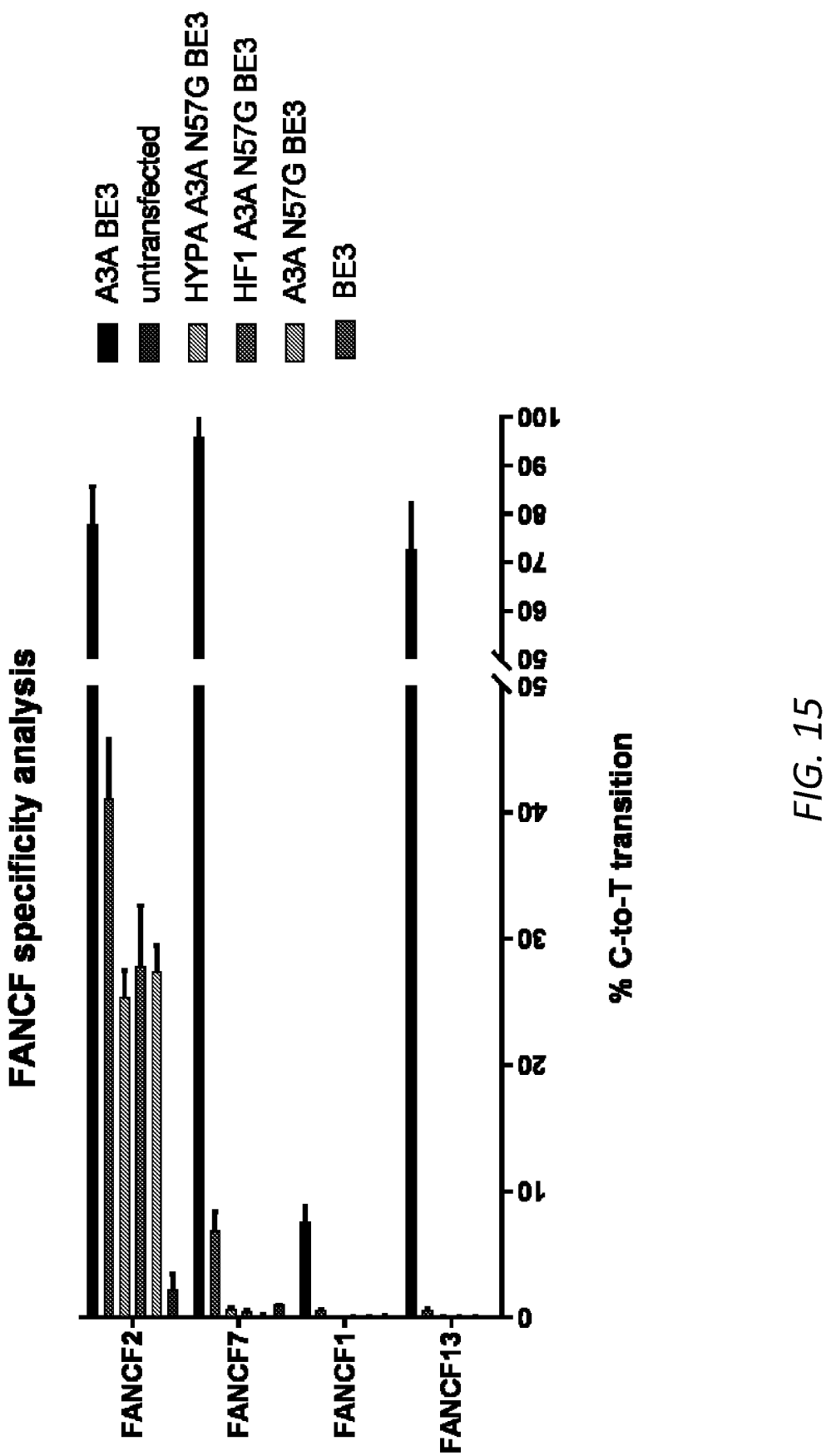
FIG. 15. HEK293T cells were transiently transfected with plasmids expressing the indicated gRNA and base editor protein. Samples were processed as outlined before. To obtain the deamination frequencies plotted, all C-to-T transition frequencies for the cytidines falling within the editing window were summed. APO3A BE3 induced very high levels of deamination at 3 of 15 off target sites. BE3 induced deamination at the same off target sites as APO3A BE3, but at lower frequencies. APO3A N57G BE3 did not induce deamination at any of the 15 investigated off target sites.

The engineered variant APO3A N57G BE3 also demonstrates increased genome-wide fidelity at off-target sites compared to wild-type APO3A BE3 and BE3. We transiently transfected cells with plasmid DNA encoding APO3A BE3, APO3A N57G BE3, or BE3 along with plasmid that expresses the well-characterized EMX1 (FIG. 14) or FANCF gRNAs (FIG. 15). BE3 induced detectable editing by high-throughput sequencing at 16 of the 25 previously-identified off-target sites for EMX1 and at 3 of the 15 off-target sites for FANCF. Conversely, APO3A N57G BE3 induced editing at 6/25 sites for EMX1 and 0/15 for FANCF. At sites that APO3A N57G BE3 did induce off-target editing at, it was at greatly reduced frequencies compared to BE3. Addition of the high fidelity mutations from HF1 or Hypa SpCas9 to APO3A N57G BE3 reduced all off-target editing to below the detection threshold of the assay.

Figure 16:
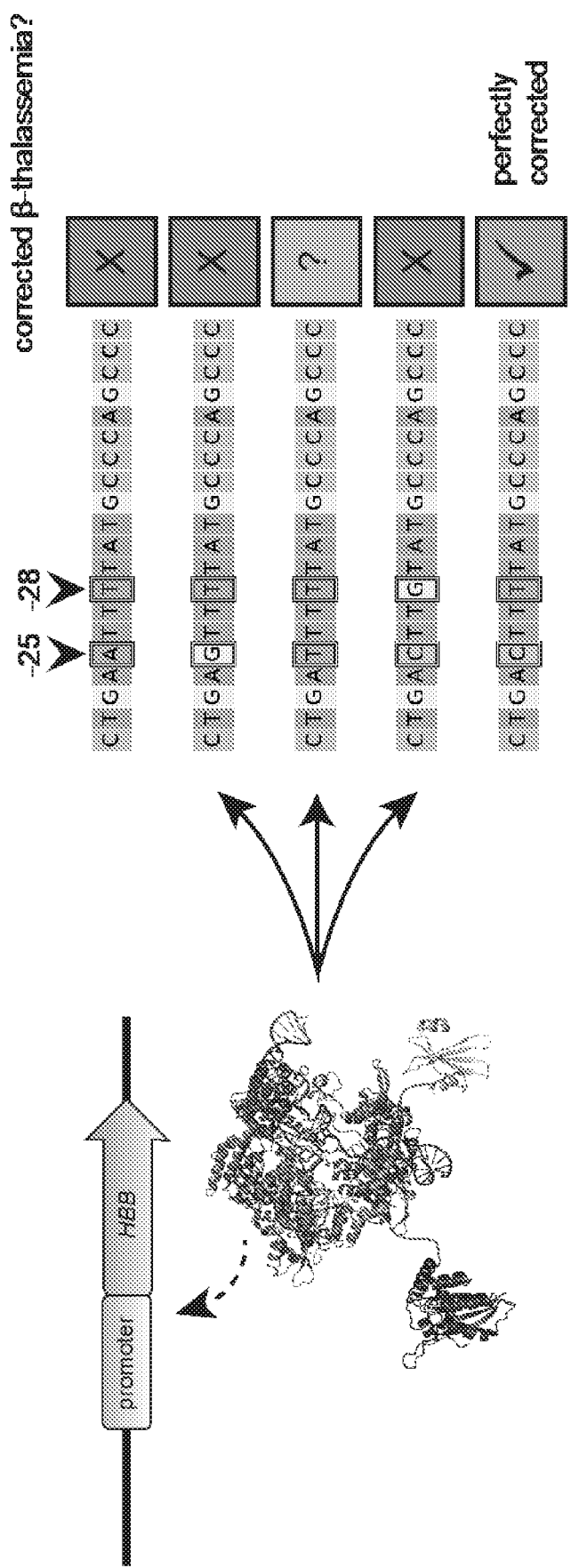
FIG. 16. Schematic showing the potential allele products from targeting the HBB-28(A>G) disease allele with base editor proteins. Mutation of the −25 bystander cytidine present in the editing window causes beta-thalassemia phenotypes independent of editing at the −28 position. As such, it's critical that the −25 position in not edited by the base editor protein. SEQ ID NOs:38-42 are shown.

Finally, we sought to determine whether APO3A N57G base editors could be used to more efficiently correct the beta-thalassemia mutation HBB-28 (A>G). In the gRNA targeting this mutation (CTGACTTcTATGCCCAGCCC (where the bolded lowercase "c" is the target cytosine)) on the antisense strand, a second cytidine preceded by a 5'A (bystander cytidine) exists in the editing window in addition to the target cytidine preceded by a 5'T at position −28. Mutation of the bystander cytidine produces independent beta thalassemia phenotypes and should be avoided in any potential therapy for the HBB-28 (A>G) mutation. We transiently transfected plasmid DNA encoding BE3 or APO3A N57G BE3 (as well as the other proteins shown in FIG. 16, including those adding a second UGI domain to A3A N57G BE3 or the HF1 or Hypa high fidelity mutations to the nCas9 moiety) into HEK293 cells bearing a lentivirally-integrated 200 base pair fragment of the HBB promoter encoding the HBB-28 (A>G) mutation. After 72 hours, we harvested genomic DNA from the cells and used PCR to amplify the target site, and sequenced the PCR product by illumina high throughput sequencing to examine the deamination frequencies of both the target and bystander cytidines.

Figure 17:
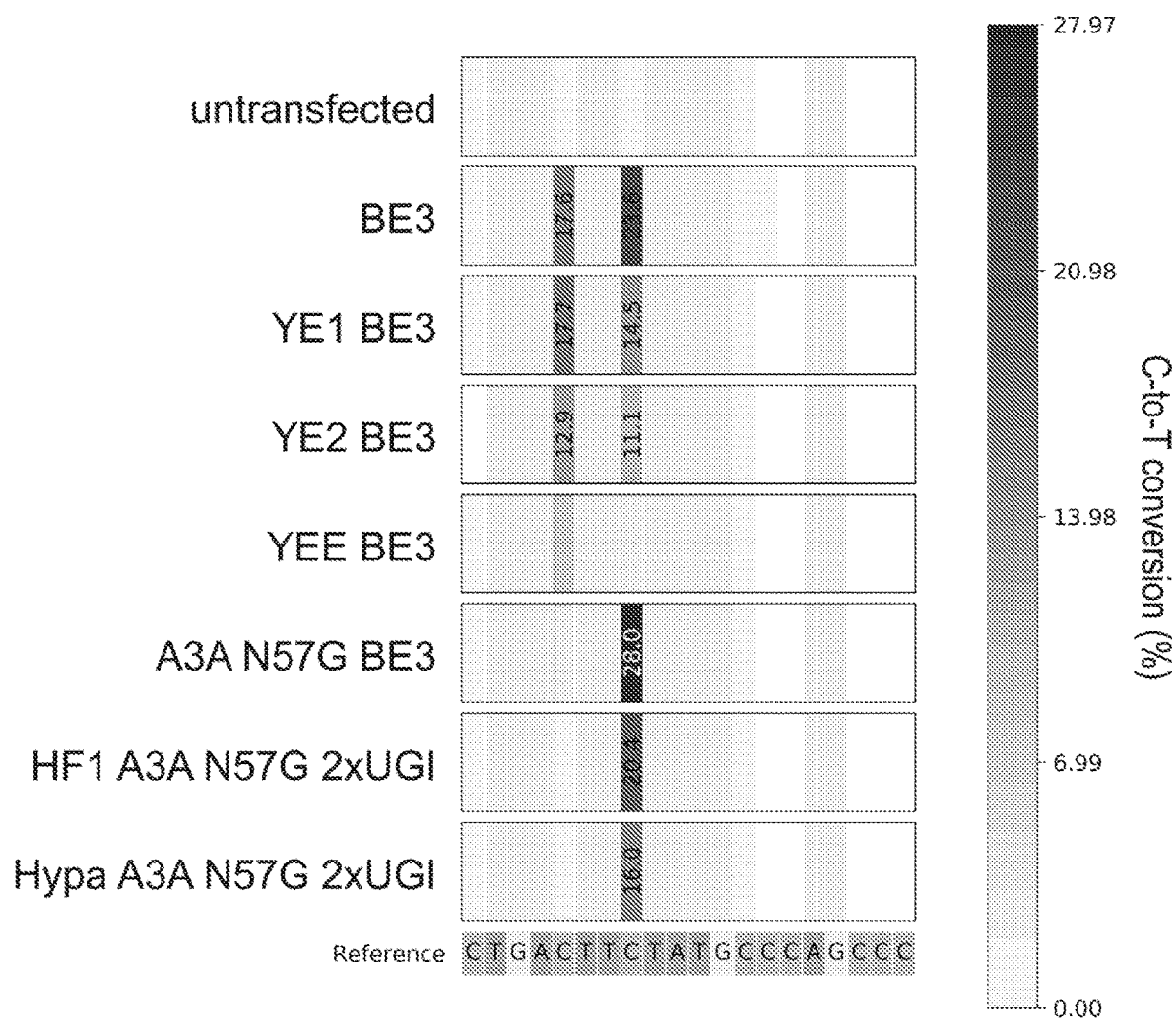
FIG. 17. HEK293T cells bearing a chromosomally-integrated, 200 base pair fragment of the HBB-28 (A>G) disease-causing allele were transiently transfected with plasmids expressing the HBB-28-targeting gRNA and the indicated BE protein. BE3 and the YE BE3 proteins deaminated the cognate and non-cognate cytidines are approximately equal frequencies, while the APO3A N57G BE proteins strongly deaminated the-28 cognate motif to correct the disease while avoiding deamination of the second cytidine in the editing window. Reference sequence, SEQ ID NO:43.
Figure 18:
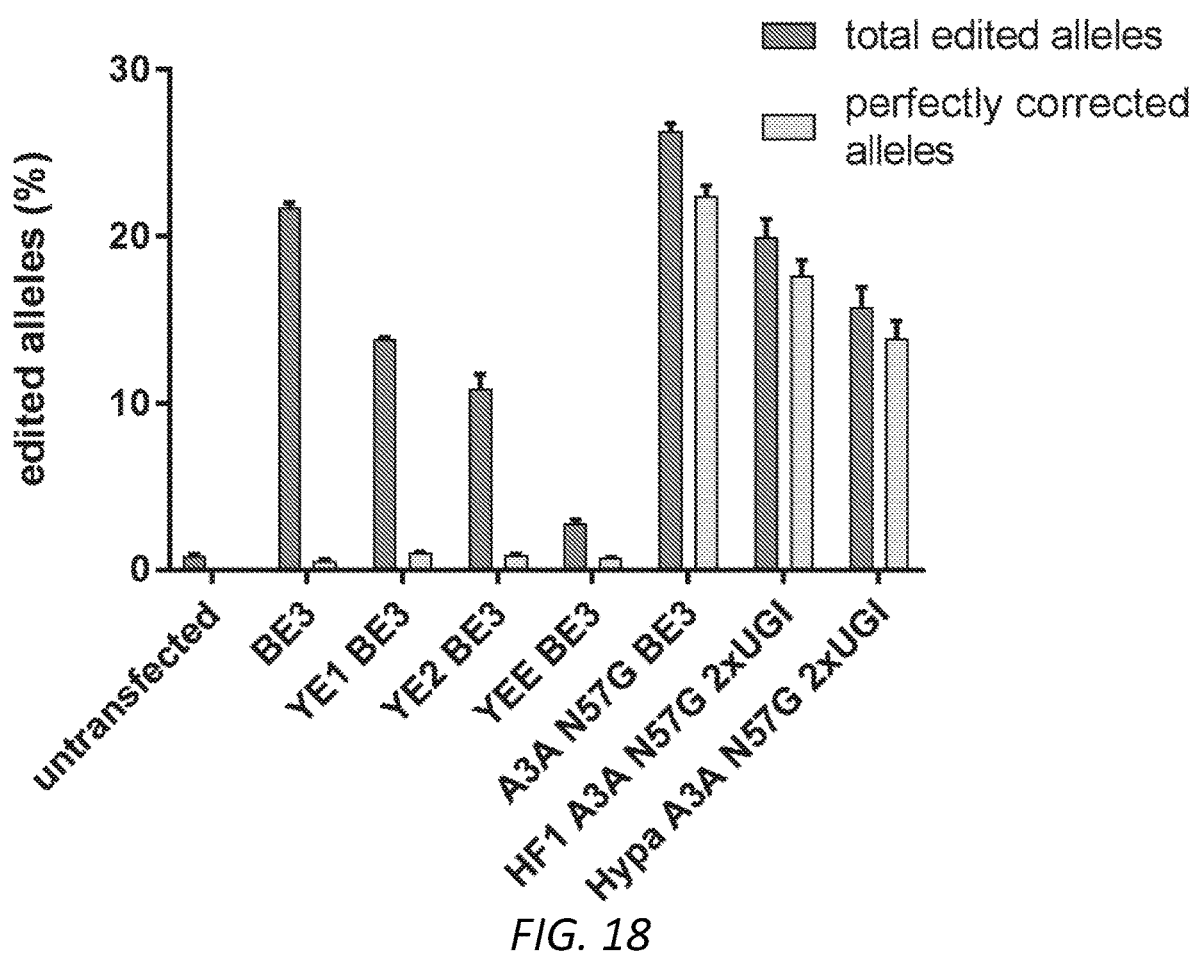
FIG. 18. BE3 and the YE BE3 proteins induce deamination of the disease-causing HBB-28 (A>G) mutation, but this results in a perfectly corrected allele in less than 1% of total alleles sequenced. Conversely, APO3A N57G BE proteins produce perfectly corrected alleles in 15-22% of total alleles sequenced.
Figure 19:
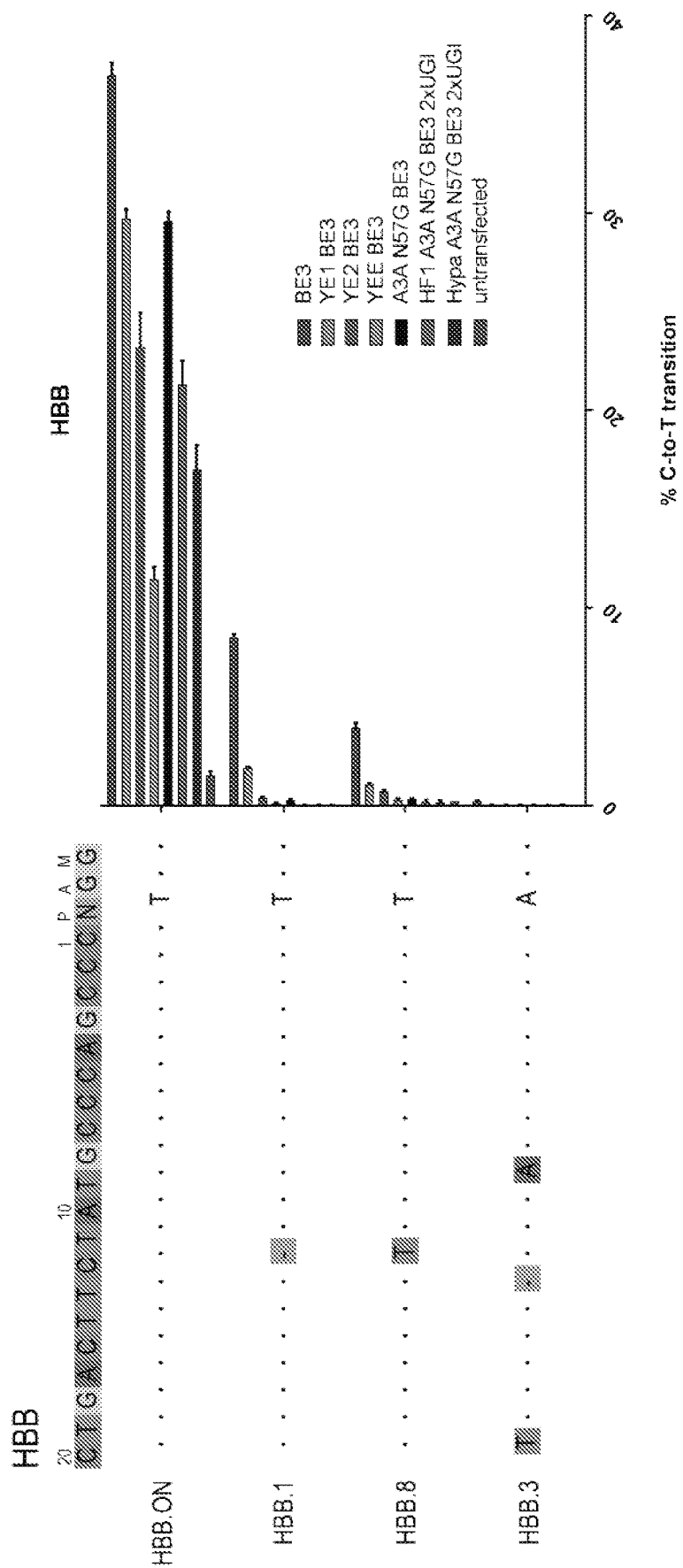
FIG. 19. HEK293T cells bearing a chromosomally-integrated fragment of the HBB-28 (A>G) allele were transiently transfected with plasmids expressing the indicated gRNA and base editor protein. Samples were processed as outlined before. To obtain the deamination frequencies plotted, all C-to-T transition frequencies for the cytidines falling within the editing window were summed. BE3 produced deamination at 3 of 8 off target sites investigated, while APO3A N57 BE3 produced deamination at just one of the 8 sites, and at very low frequency. SEQ ID NO:44 is shown.

We found that, while the BE3 and YE BE3 proteins edited both the target and bystander cytidines at approximately equal rates, APO3A N57G BE3 deaminated the target cytidine approximately 15-fold more than the bystander cytidine (FIG. 17). We then analyzed the frequency with which editing the HBB-28 (A>G) site with BE3 produced perfectly corrected alleles (i.e. alleles in which the −28 position has been edited but not any other position). BE3 produced perfectly edited alleles at a frequency of 0.5% of the total alleles sequenced. Conversely, editing with APO3A N57G BE3 produced perfectly edited alleles at a rate of 22% of total sequenced alleles, 40-fold more than editing with BE3 (FIG. 18). We next investigated whether editing with APO3A N57G BE3 produced fewer off target deamination events than BE3 using the HBB-28 (A>G) gRNA. BE3 induced detectable deamination at 3 of 8 off target sites, while APO3A N57G BE3 induced editing at just 1 of the 8 off target sites (FIG. 19). Thus, the engineered APO3A N57G BE3 variant is able to more efficiently correct the HBB-28 (A>G) disease-causing allele with fewer off-target effects at the eight examined sites as compared to BE3 or the state-of-the-art YE BE3 proteins.

In additional experiments, a human patient's CD34+ HSPCs that have the HBB-28 (A>G) mutation that are harvested from donation are used. Purified A3A N57G BE3 protein is delivered with guide RNA to the cells. After 5 days, gDNA is extracted and disease correction is evaluated by sequencing.

The mutations listed in Table 7 can be used to increase specificity of deaminase proteins or domains on their own or in any possible combinations. The mutations listed in Table 8 are intended to alter the targetable motif sequence, and can be combined with any of the mutations in Table 7 to create engineered deaminase proteins or domains with altered and increased substrate sequence. Further, the mutations listed in Table 9 can be combined with any of the mutations listed in Table 7 or Table 8 to create engineered deaminase proteins with altered specificity for the first or third nucleotide in a trinucleotide motif and with increased specificity for its target motif relative to other possible deamination substrate motifs.

TABLE 7

Mutations that enhance the sequence specificity of cytidine deaminase proteins by affecting the protein:substrate interaction interface

| | Mutation | | | | | |
|---|---|---|---|---|---|---|
| | 1 | 2 | 3 | 4 | 5 | 6 |
| APO3A | R28A, E, or Q | K30A, E, or Q | N57A, G, D, E, K, Q, or S | K60A, D, E, R, N, or Q | W98Y | Y130A or F |
| rAPOBEC1* | — | E22A, K, or Q | S49A, G, D, E, K, or Q | R52A, D, E, K, N, or Q | W90Y | Y120A or F |
| mAPOBEC3* | R39A, E, or Q | D41A, E, or Q | N66A, G, D, E, K, Q, or S | D68A, E, R, N, or Q | W102Y | Y132A or F |
| hAPOBEC3C | R30A, E, or Q | E32A, D, or Q | N57A, G, D, E, K, Q, or S | D60A, E, R, N, or Q | W94Y | Y124A or F |
| hAPOBEC3G | R215A, E, or Q | E217A, D, or Q | N244A, G, D, E, K, Q, or S | — | W285Y | Y315A or F |
| hAPOBEC3H* | — | R21A, E, or Q | N49A, D, E, K, Q, or S | K52A, D, E, R, N, or Q | W82Y | Y112A or F OR Y113A or F |
| hAPOBEC3F | R213A, E, or Q | E215A, K, or Q | N240A, D, E, K, Q, or S | D243A, E, R, N, or Q | W277Y | Y307F |

*indicates which proteins lack sufficient structural information.

Table 7 shows APOBEC orthologs with significant sequence and structural similarity for specificity engineering. In these cases, protein sequence alignment to APO3A was used to determine the residue homologous to the APO3A position. Each of the six residue positions to be mutated are listed with one or more residues that are expected to increase the specificity of that deaminase domain for its canonical or re-engineered substrate sequence by reducing excess binding energy between the deaminase protein and its ssDNA substrate.

TABLE 8

APOBEC orthologs with significant sequence and structural similarity for substrate sequence specificity re-engineering (* indicates which proteins lack sufficient structural information.

| | Substrate motif | 5'-TC | 5'-GC | 5'-AC | 5'-CC |
|---|---|---|---|---|---|
| APO3A | 5'-TCR | D131 | D131R/K | D131N/Q/R | D131E/H/S |
| mAPOBEC3* | 5'-TYC | N133D | N133R/K | N133Q/R | N133E/H/S |
| hAPO3B | 5'-TCR | D314 | D314R/K | D314N/Q/R | D314E/H/S |
| hAPOBEC3C | 5'-YC | Y125D | Y125R/K | Y125N/Q/R | Y125E/H/S |
| hAPOBEC3G | 5'-CCC | D316 | D316R/K | D316N/Q/R | D316 |
| hAPOBEC3H* | 5'-TC | H114 | H114R/K | H114N/Q/R | H114E/S |
| hAPOBEC3F | 5'-TC | Y308 | Y308R/K | Y308N/Q/R | Y308E/H/S |

*indicates which proteins lack sufficient structural information.

In these cases, protein sequence alignment to APO3A was used to determine the residue homologous to APO3A D131. The position and identity of the residue mutations expected to alter each protein's sequence specificity are given for each two-nucleotide motif. All positional information refers to the wild-type protein sequences acquired from uniprot.org.

TABLE 9

APOBEC orthologs with significant sequence and structural similarity for substrate sequence specificity re-engineering

|  | 5'-NCA | 5'-NCG | 5'-NCT | 5'-NCC |
|---|---|---|---|---|
| APO3A | K30N/Q/R | K30R | K30D/E/R | K30D/E/H/S |
| hAPO3B* | Q213N/R | Q213R/K | Q213D/E/R | Q213D/E/H/S |

*indicates which proteins lack sufficient structural information. In these cases, protein sequence alignment to APO3A was used to determine the residue homologous to APO3A K30. The position and identity of the residue mutations expected to alter each protein's sequence specificity are given for each three-nucleotide motif. All positional information refers to the wild-type protein sequences acquired from uniprot.org.

TABLE 10

Mutations that enhance the sequence specificity of cytidine deaminase proteins by affecting the kinetic rate and processivity of the enzyme.

| | Mutation | |
|---|---|---|
| | 1 | 2 |
| APO3A | A71G, V, I, L, S, or T | I96T, S, A, V, L, M, or G |
| rAPOBEC1 | V62G, V, I, L, S, or T | L88T, S, A, V, I, M, or G |
| mAPOBEC3 | A72G, V, I, L, S, or T | M100T, S, A, V, I, L, or G |
| hAPOBEC3C | A67G, V, I, L, S, or T | T92S, A, V, I, L, M, or G |
| hAPOBEC3G | A258G, V, I, L, S, or T | T283S, A, V, I, L, M, or G |
| hAPOBEC3H | A55G, V, I, L, S, or T | L80T, S, A, V, I, M, or G |
| hAPOBEC3F | A250G, V, I, L, S, or T | T275S, A, V, I, L, M, or G |

REFERENCES

1. Komor, Alexis C., Yongjoo B. Kim, Michael S. Packer, John A. Zuris, and David R. Liu. "Programmable Editing of a Target Base in Genomic DNA without Double-stranded DNA Cleavage." *Nature* 533.7603 (2016): 420-24.
2. Yang, Luhan, Adrian W. Briggs, Wei Leong Chew, Prashant Mali, Marc Guell, John Aach, Daniel Bryan Goodman, David Cox, Yinan Kan, Emal Lesha, Venkataramanan Soundararajan, Feng Zhang, and George Church. "Engineering and Optimising Deaminase Fusions for Genome Editing." *Nature Communications* 7 (2016): 13330.
3. Jasin, Maria, and Rodney Rothstein. "Repair of strand breaks by homologous recombination." *Cold Spring Harbor perspectives in biology* 5.11 (2013): a012740.
4. Cone, Richard, Thomas Bonura, and E. C. Friedberg. "Inhibitor of uracil-DNA glycosylase induced by bacteriophage PBS2. Purification and preliminary characterization." *Journal of Biological Chemistry* 255.21 (1980): 10354-10358.
5. Kuscu, Cem, and Mazhar Adli. "CRISPR-Cas9-AID Base Editor Is a Powerful Gain-of-function Screening Tool." *Nature Methods* 13.12 (2016): 983-84.
6. Hess, Gaelen T., Laure Fresard, Kyuho Han, Cameron H. Lee, Amy Li, Karlene A. Cimprich, Stephen B. Montgomery, and Michael C. Bassik. "Directed Evolution Using DCas9-targeted Somatic Hypermutation in Mammalian Cells." *Nature Methods* 13.12 (2016): 1036-042.
7. Nishida, K., T. Arazoe, N. Yachie, S. Banno, M. Kakimoto, M. Tabata, M. Mochizuki, A. Miyabe, M. Araki, K. Y. Hara, Z. Shimatani, and A. Kondo. "Targeted Nucleotide Editing Using Hybrid Prokaryotic and Vertebrate Adaptive Immune Systems." *Science* 353.6305 (2016).
8. Tsai, Shengdar Q., Zongli Zheng, Nhu T. Nguyen, Matthew Liebers, Ved V. Topkar, Vishal Thapar, Nicolas Wyvekens, Cyd Khayter, A. John Iafrate, Long P. Le, Martin J. Aryee, and J. Keith Joung. "GUIDE-seq Enables Genome-wide Profiling of Off-target Cleavage by CRISPR-Cas Nucleases." *Nature Biotechnology* 33.2 (2014): 187-97.
9. Wu, Xuebing, David A. Scott, Andrea J. Kriz, Anthony C. Chiu, Patrick D. Hsu, Daniel B. Dadon, Albert W. Cheng, Alexandro E. Trevino, Silvana Konermann, Sidi Chen, Rudolf Jaenisch, Feng Zhang, and Phillip A. Sharp. "Genome-wide Binding of the CRISPR Endonuclease Cas9 in Mammalian Cells." *Nature Biotechnology* 32.7 (2014): 670-76.
10. Kim, Y. Bill, Alexis C. Komor, Jonathan M. Levy, Michael S. Packer, Kevin T. Zhao, and David R. Liu. "Increasing the Genome-targeting Scope and Precision of Base Editing with Engineered Cas9-cytidine Deaminase Fusions." *Nature Biotechnology* 35.4 (2017): 371-76.
11. Byeon, In-Ja L., Jinwoo Ahn, Mithun Mitra, Chang-Hyeock Byeon, Kamil Hercik, JozefHritz, Lisa M. Charlton, Judith G. Levin, and Angela M. Gronenborn. "NMR Structure of Human Restriction Factor APOBEC3A Reveals Substrate Binding and Enzyme Specificity." *Nature Communications* 4 (2013): 1890.
12. Bransteitter, Ronda, Courtney Prochnow, and Xiaojiang S. Chen. "The Current Structural and Functional Understanding of APOBEC Deaminases." *Cellular and Molecular Life Sciences* 66.19 (2009): 3137-147.
13. Mitra, Mithun, Dustin Singer, Yu Mano, Jozef Hritz, Gabriel Nam, Robert J. Gorelick, In-Ja L. Byeon, Angela M. Gronenborn, Yasumasa Iwatani, and Judith G. Levin. "Sequence and Structural Determinants of Human APOBEC3H Deaminase and Anti-HIV-1 Activities." *Retrovirology* 12.1 (2015): 3.
14. Nair, S., S. Sanchez-Martinez, X. Ji, and A. Rein. "Biochemical and Biological Studies of Mouse APOBEC3." *Journal of Virology* 88.7 (2014): 3850-860.
15. Langlois, Marc-Andre, et al. "Mutational comparison of the single-domained APOBEC3C and double-domained APOBEC3F/G anti-retroviral cytidine deaminases provides insight into their DNA target site specificities." *Nucleic acids research* 33.6 (2005): 1913-1923.
16. Harris, Reuben S., Svend K. Petersen-Mahrt, and Michael S. Neuberger. "RNA Editing Enzyme APOBEC1 and Some of Its Homologs Can Act as DNA Mutators." *Molecular Cell* 10.5 (2002): 1247-253.
17. Chen, Kuan-Ming, Elena Harjes, Phillip J. Gross, Amr Fahmy, Yongjian Lu, Keisuke Shindo, Reuben S. Harris, and Hiroshi Matsuo. "Structure of the DNA Deaminase Domain of the HIV-1 Restriction Factor APOBEC3G." *Nature* 452.7183 (2008): 116-19.
18. Pham, Phuong, Samir A. Afif, Mayuko Shimoda, Kazuhiko Maeda, Nobuo Sakaguchi, Lars C. Pedersen, and Myron F. Goodman. "Structural Analysis of the Activation-induced Deoxycytidine Deaminase Required in Immunoglobulin Diversification." *DNA Repair* 43 (2016): 48-56.
19. Shandilya, Shivender M.d., Madhavi N.l. Nalam, Ellen A. Nalivaika, Phillip J. Gross, Johnathan C. Valesano, Keisuke Shindo, Ming Li, Mary Munson, William E. Royer, Elena Harjes, Takahide Kono, Hiroshi Matsuo, Reuben S. Harris, Mohan Somasundaran, and Celia A. Schiffer. "Crystal Structure of the APOBEC3G Catalytic Domain Reveals Potential Oligomerization Interfaces." *Structure* 18.1 (2010): 28-38.
20. Shi, Ke, Michael A. Carpenter, Kayo Kurahashi, Reuben S. Harris, and Hideki Aihara. "Crystal Structure of the DNA Deaminase APOBEC3B Catalytic Domain." *Journal of Biological Chemistry* 290.47 (2015): 28120-8130.
21. Shi, Ke, Michael A. Carpenter, Surajit Banerjee, Nadine M. Shaban, Kayo Kurahashi, Daniel J. Salamango, Jennifer L. Mccann, Gabriel J. Starrett, Justin V. Duffy, Özlem Demir, Rommie E. Amaro, Daniel A. Harki, Reuben S. Harris, and Hideki Aihara. "Structural Basis for Targeted DNA Cytosine Deamination and Mutagenesis by APOBEC3A and APOBEC3B." *Nature Structural & Molecular Biology* 24.2 (2016): 131-39.
22. Salter, Jason D., Ryan P. Bennett, and Harold C. Smith. "The APOBEC Protein Family: United by Structure, Divergent in Function." *Trends in Biochemical Sciences* 41.7 (2016): 578-94.
23. Holden L G, Prochnow C, Chang P Y, Bransteitter R, Chelico L, Sen U, Stevens R C, Goodman M F, Chen X S (2008) Crystal structure of the anti-viral APOBEC3G catalytic domain and functional implications. Nature 456: 121-124.
24. Logue, Eric C., et al. "A DNA sequence recognition loop on APOBEC3A controls substrate specificity." *PloS one* 9.5 (2014): e97062.
25. *Kohli*, R. M., S. R. Abrams, K. S. Gajula, R. W. Maul, P. J. Gearhart, and J. T. Stivers. "A Portable Hot Spot Recognition Loop Transfers Sequence Preferences from APOBEC Family Members to Activation-induced Cytidine Deaminase." *Journal of Biological Chemistry* 284.34 (2009): 22898-2904.
26. Kim, Daesik, Kayeong Lim, Sang-Tae Kim, Sun-Heui Yoon, Kyoungmi Kim, Seuk-Min Ryu, and Jin-Soo Kim. "Genome-wide Target Specificities of CRISPR RNA-guided Programmable Deaminases." *Nature Biotechnology* (2017).
27. Kleinstiver, Benjamin P., Vikram Pattanayak, Michelle S. Prew, Shengdar Q. Tsai, Nhu T. Nguyen, Zongli Zheng, and J. Keith Joung. "High-fidelity CRISPR-Cas9 Nucleases with No Detectable Genome-wide Off-target Effects." *Nature* 529.7587 (2016): 490-95.
28. Slaymaker, I. M., L. Gao, B. Zetsche, D. A. Scott, W. X. Yan, and F. Zhang. "Rationally Engineered Cas9 Nucleases with Improved Specificity." *Science* 351.6268 (2015): 84-88.
29. Dahlman, James E., Omar O. Abudayyeh, Julia Joung, Jonathan S. Gootenberg, Feng Zhang, and Silvana Konermann. "Orthogonal Gene Knockout and Activation with a Catalytically Active Cas9 Nuclease." *Nature Biotechnology* 33.11 (2015): 1159-161.
30. Fu, Yanfang, et al. "Improving CRISPR-Cas nuclease specificity using truncated guide RNAs." *Nature biotechnology* 32.3 (2014): 279-284.
31. Boissel, S., J. Jarjour, A. Astrakhan, A. Adey, A. Gouble, P. Duchateau, J. Shendure, B. L. Stoddard, M. T. Certo, D. Baker, and A. M. Scharenberg. "MegaTALs: A Rare-cleaving Nuclease Architecture for Therapeutic Genome Engineering." *Nucleic Acids Research* 42.4 (2013): 2591-601.
32. Bolukbasi, Mehmet Fatih, Ankit Gupta, Sarah Oikemus, Alan G. Derr, Manuel Garber, Michael H. Brodsky, Lihua Julie Zhu, and Scot A. Wolfe. "DNA-binding-domain Fusions Enhance the Targeting Range and Precision of Cas9." *Nature Methods* 12.12 (2015): 1150-156.
33. Kleinstiver, Benjamin P., et al. "Broadening the targeting range of *Staphylococcus aureus* CRISPR-Cas9 by modifying PAM recognition." *Nature biotechnology* (2015).
34. Ma, Enbo, et al. "Single-stranded DNA cleavage by divergent CRISPR-Cas9 enzymes." *Molecular cell* 60.3 (2015): 398-407.
35. Santos-Pereira, Jose M., and Andres Aguilera. "R Loops: New Modulators of Genome Dynamics and Function." *Nature Reviews Genetics* 16.10 (2015): 583-97.
36. Rebhandl, Stefan, Michael Huemer, Richard Greil, and Roland Geisberger. "AID/APOBEC Deaminases and Cancer." *Oncoscience* 2 (2015): 320.
37. Suspene, Rodolphe, et al. "Recovery of APOBEC3-edited human immunodeficiency virus G→A hypermutants by differential DNA denaturation PCR." *Journal of general virology* 86.1 (2005): 125-129.
38. Aynaud, Marie-Ming, et al. "Human Tribbles 3 protects nuclear DNA from cytidine deamination by APOBEC3A." *Journal of Biological Chemistry* 287.46 (2012): 39182-39192.
39. Shinohara, Masanobu, et al. "APOBEC3B can impair genomic stability by inducing base substitutions in genomic DNA in human cells." *Scientific reports* 2 (2012): 806.
40. Holtz, Colleen M., Holly A. Sadler, and Louis M. Mansky. "APOBEC3G cytosine deamination hotspots are defined by both sequence context and single-stranded DNA secondary structure." *Nucleic acids research* (2013): gkt246.
41. Rebhandl, Stefan, Michael Huemer, Richard Greil, and Roland Geisberger. "AID/APOBEC Deaminases and Cancer." *Oncoscience* 2 (2015): 320.
42. Ear, Po Hien, and Stephen W. Michnick. "A General Life-death Selection Strategy for Dissecting Protein Functions." *Nature Methods* 6.11 (2009): 813-16.
43. Luscombe, Nicholas M., Roman A. Laskowski, and Janet M. Thornton. "Amino acid-base interactions: a three-dimensional analysis of protein-DNA interactions at an atomic level." *Nucleic acids research* 29.13 (2001): 2860-2874.
44. Kim, Y. Bill, et al. "Increasing the genome-targeting scope and precision of base editing with engineered Cas9-cytidine deaminase fusions." *Nature Biotechnology* 35.4 (2017): 371-376.

45. Rees, Holly A., et al. "Improving the DNA specificity and applicability of base editing through protein engineering and protein delivery." *Nature Communications* 8 (2017): ncomms15790.
46. Kleinstiver, Benjamin P., et al. "Engineered CRISPR-Cas9 nucleases with altered PAM specificities." *Nature* 523.7561 (2015): 481-485.
47. Kleinstiver, Benjamin P., et al. "Broadening the targeting range of *Staphylococcus aureus* CRISPR-Cas9 by modifying PAM recognition." *Nature biotechnology* 33.12 (2015): 1293-1298.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A fusion protein comprising a Cas9-like nickase (nCas9) linked to an engineered variant human apolipoprotein B mRNA editing enzyme catalytic subunit 3A (hAPOBEC3A) deaminase, with an optional intervening linker, wherein the engineered variant hAPOBEC3A deaminase has at least 85% sequence identity to SEQ ID NO:57 and comprises one or more mutations selected from R28 to A, E, or Q; K30 to A, E, Q, N, R, D, H, or S; N57 to A, G, D, E, K, Q, or 8; K60 to A, D, E, N, or Q; W98Y; Y130A; or D131 to R, K, N, Q, H, or S of SEQ ID NO:57.

2. The fusion protein of claim 1, wherein the engineered variant hAPOBEC3A deaminase comprises one or more mutations selected from selected from R28 to A, E, or Q; K30 to A, E, or Q; N57 to A, G, D, E, K, Q, or S; K60 to A, D, E, N, or Q; W98Y; Y130A; or D131 to R, K, N, Q, H, or S.

3. The fusion protein of claim 1, wherein the engineered variant hAPOBEC3A deaminase comprises (i) one or more mutations selected from R28 to A, E, or Q; N57 to A, G, D, E, K, Q, or S; K60 to A, D, E, N, or Q; W98Y; Y130A; or D131 to R, K, N, Q, H, or S and (ii) a mutation at K30 to E, Q, N, R, D, H, or S.

4. The fusion protein of claim 1, wherein the engineered variant hAPOBEC3A deaminase comprises a mutation at N57 and further comprises the mutation at K60 to A, D, E, N or Q.

5. The fusion protein of claim 4, comprising (i) one or both of a N57G or N57Q mutation or a K60A or K60D mutation; and (ii) a Y130F mutation.

6. The fusion protein of claim 4, comprising one or more of a mutation of N57Q or K60D; and optionally also a mutation of Y130 to F.

7. The fusion protein of claim 6, wherein the engineered variant hAPOBEC3A deaminase comprises one or both of a N57Q mutation or a K60D mutation; and also a Y130F mutation.

8. The fusion protein of claim 7, wherein the engineered variant hAPOBEC3A deaminase comprises a N57Q mutation and also a Y130F mutation.

9. The fusion protein of claim 1, wherein the engineered variant hAPOBEC3A deaminase comprises a mutation at N57 and Y130.

10. The fusion protein of claim 1, wherein the engineered variant hAPOBEC3A deaminase further comprises a mutation at A71 and/or I96.

11. A composition comprising the fusion protein of claim 1, and a guide RNA.

12. The composition of claim 11, comprising one or more ribonucleoprotein (RNP) complexes.

13. The fusion protein of claim 1, wherein the engineered variant hAPOBEC3A deaminase has at least 90% identity to SEQ ID NO:57.

14. The fusion protein of claim 1, wherein the engineered variant hAPOBEC3A deaminase has at least 95% identity to SEQ ID NO:57.

15. The fusion protein of claim 1, wherein the fusion protein further comprises a uracil glycosylase inhibitor (UGI).

16. The fusion protein of claim 1, wherein the engineered variant hAPOBEC3A deaminase has at least 95% identity to SEQ ID NO:57.

17. The fusion protein of claim 1, wherein the engineered variant hAPOBEC3A deaminase comprises one or more mutations selected from selected from N57 to A, G, D, E, K, Q, or S.

18. A fusion protein comprising a Cas9-like nickase (nCas9) linked to an engineered variant human apolipoprotein B mRNA editing enzyme catalytic subunit 3A (hAPOBEC3A) deaminase, with an optional intervening linker, wherein the engineered variant hAPOBEC3A deaminase has at least 80% sequence identity to SEQ ID NO:57 and comprises: (i) one or more mutations R28 to A, E, or Q; K30 to A, E, Q, N, R, D, H, or 8; N57 to A, G, D, E, K, Q, or S; K60 to A, D, E, N, or Q; W98Y; or D131 to R, K, N, Q, E, H, or S of SEQ ID NO:57; and (ii) a mutation Y130A or Y130F.

19. The fusion protein of claim 18, wherein the engineered variant hAPOBEC3A deaminase has at least 85% identity to SEQ ID NO:57.

20. The fusion protein of claim 18, wherein the engineered variant hAPOBEC3A deaminase has at least 90% identity to SEQ ID NO:57.

21. The fusion protein of claim 18, wherein the engineered variant hAPOBEC3A deaminase comprises one or more mutations selected from selected from N57 to A, G, D, E, K, Q, or S.

* * * * *

UNITED STATES PATENT AND TRADEMARK OFFICE
CERTIFICATE OF CORRECTION

PATENT NO. : 11,326,157 B2
APPLICATION NO. : 16/615559
DATED : May 10, 2022
INVENTOR(S) : J. Keith Joung and Jason Michael Gehrke It is certified that error appears in the above-identified patent and that said Letters Patent is hereby corrected as shown below:

In the Claims

In Column 105, Line 10 (approx.), Claim 1, delete "8;" and insert -- S; --

In Column 105, Line 15 (approx.), Claim 2, delete "selected from selected from" and insert -- selected from --

In Column 106, Line 3, Claim 10, delete "196" and insert -- I96 --

In Column 106, Line 21, Claim 17, delete "selected from selected from" and insert -- selected from --

In Column 106, Line 30 (approx.), Claim 18, delete "8;" and insert -- S; --

In Column 106, Line 42 (approx.), Claim 21, delete "selected from selected from" and insert -- selected from --

Signed and Sealed this
Eighteenth Day of April, 2023

Katherine Kelly Vidal
*Director of the United States Patent and Trademark Office*